United States Patent
Valerio Santiago et al.

(10) Patent No.: US 12,419,824 B2
(45) Date of Patent: Sep. 23, 2025

(54) COMPOUNDS USEFUL FOR THE TREATMENT AND/OR CARE OF THE SKIN, HAIR, NAILS AND/OR MUCOUS MEMBRANES

(71) Applicant: Lubrizol Advanced Materials, Inc., Cleveland, OH (US)

(72) Inventors: Mauricio Valerio Santiago, Cadiz (ES); Consuelo García Hernández, Murcia (ES); Núria Almiñana Doménech, Barcelona (ES); Albert Soley Astals, Barcelona (ES)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 302 days.

(21) Appl. No.: 17/427,364

(22) PCT Filed: Feb. 10, 2020

(86) PCT No.: PCT/IB2020/051021
§ 371 (c)(1),
(2) Date: Jul. 30, 2021

(87) PCT Pub. No.: WO2020/161683
PCT Pub. Date: Aug. 13, 2020

(65) Prior Publication Data
US 2022/0183950 A1   Jun. 16, 2022

(30) Foreign Application Priority Data
Feb. 8, 2019  (EP) ..................................... 19382092

(51) Int. Cl.
| A61K 38/00 | (2006.01) |
| A61K 8/64 | (2006.01) |
| A61Q 19/06 | (2006.01) |
| A61Q 19/08 | (2006.01) |
| C07K 5/113 | (2006.01) |
| C07K 7/06 | (2006.01) |

(52) U.S. Cl.
CPC ................ *A61K 8/64* (2013.01); *A61Q 19/06* (2013.01); *A61Q 19/08* (2013.01); *C07K 5/1021* (2013.01); *C07K 7/06* (2013.01); *A61K 38/00* (2013.01)

(58) Field of Classification Search
None
See application file for complete search history.

(56) References Cited

U.S. PATENT DOCUMENTS

| 5,370,996 | A | * | 12/1994 | Metz | C12N 9/0008 536/23.6 |
| 7,660,677 | B2 | | 2/2010 | Tanuma et al. | |
| 7,736,639 | B2 | | 6/2010 | Bam et al. | |
| 8,058,016 | B2 | | 11/2011 | Nordstedt et al. | |
| 8,669,089 | B2 | | 3/2014 | Helbert et al. | |
| 8,865,651 | B2 | | 10/2014 | Otte et al. | |
| 9,493,522 | B2 | | 11/2016 | Wells et al. | |
| 9,597,274 | B2 | | 3/2017 | Idkowiak-Baldys et al. | |
| 9,725,483 | B2 | | 8/2017 | García et al. | |
| 9,771,392 | B2 | | 9/2017 | Ferrer Montiel et al. | |
| 10,107,820 | B2 | | 10/2018 | Reilly et al. | |
| 2007/0249528 | A1 | | 10/2007 | Weston | |
| 2010/0008654 | A1 | | 1/2010 | Hsu | |
| 2011/0182905 | A1 | | 7/2011 | Takada et al. | |
| 2012/0276049 | A1 | | 11/2012 | Stern et al. | |
| 2013/0183702 | A1 | | 7/2013 | Bossmann et al. | |
| 2016/0132631 | A1 | | 5/2016 | Bremel et al. | |
| 2018/0369115 | A1 | | 12/2018 | Alminana Domenech et al. | |
| 2022/0096657 | A1 | | 3/2022 | Paul et al. | |

FOREIGN PATENT DOCUMENTS

| EP | 1 992 332 A1 | 11/2008 |
| JP | 2004-081178 | 3/2004 |
| JP | 2008-502311 A | 1/2008 |
| KR | 2018 0108988 A | 10/2018 |
| WO | WO 92/09628 A1 | 6/1992 |
| WO | WO 2004087188 A1 | 10/2004 |

(Continued)

OTHER PUBLICATIONS

Albericio, F., et al., "Preparation and application of the 5-(4-(9-fluorenylmethyloxycarbonyl) aminomethyl-3,5-dimethoxy-phenoxy)valeric-acid (PAL) handle for the solid-phase synthesis of C-terminal peptide amides under mild conditions," J. Org. Chem., 55, 3730-3743(1990).
Atherton, B., et al., "Solid Phase Peptide Synthesis: A practical approach," IRL Oxford University Press, pp. 1-61 (1989).
Barlos, K., et al., "Darstellung geschützter Peptid-Fragmente unter Einsatz substituierter Triphenylmethyl-Harze," Tetrahedron Lett., 30, 3943-3946 (1989), English Abstract only.
Barlos, K., et al., "Veresterung von partiell geschützten Peptid-Fragmenten mit Harzen. Einsatz von 2-Chlorotritylchlorid zur Synthese von Leu1-Gastrin I," Tetrahedron Lett., 30, 3947-3951 (1989), English Abstract only.
Berge, S.M., et al., "Pharmaceutical Salts," J. Pharm. Sci., 66, pp. 1-19 (1977).
Bodanzsky, M., et al., "The practice of Peptide Synthesis," pp. 75-126, Springer Verlag, Berlin (1994).

(Continued)

*Primary Examiner* — Lianko G Garyu
*Assistant Examiner* — Mercy H Sabila
(74) *Attorney, Agent, or Firm* — Lippes Mathias LLP

(57) ABSTRACT

A compound of formula (I) $R_1\text{-}W_m\text{-}X_n\text{-}AA_1\text{-}AA_2\text{-}AA_3\text{-}AA_4\text{-}AA_5\text{-}AA_6\text{-}Y_p\text{-}Z_q\text{-}R_2$, a stereoisomer and/or cosmetically acceptable salt thereof, and a method of treatment using the compound are described. In the compound, $AA_1$ is Asp, Gly, Asn, Gln, Ala or no amino acid; $AA_2$ is Val, Ile, Leu or Ala; $AA_3$ is Tyr, Phe, Trp, Lys, Arg or His; $AA_4$ is Lys, Arg, His, Pro or Val; $AA_5$ is Asn, Asp, Gln or no amino acid; $AA_6$ is Thr, Ala, Ser or no amino acid. The compounds are useful for the treatment of the symptoms of skin aging and, in particular, for the treatment of skin wrinkles, the treatment of a sagging appearance of the skin, and/or the reduction of facial asymmetry.

8 Claims, 4 Drawing Sheets

Specification includes a Sequence Listing.

(56) References Cited

FOREIGN PATENT DOCUMENTS

| WO | WO 2004091517 A2 | 10/2004 | |
|---|---|---|---|
| WO | WO 2009064399 A1 | 5/2009 | |
| WO | WO 2010/021822 A2 | 2/2010 | |
| WO | WO 2011044452 A2 | 4/2011 | |
| WO | WO 2011082376 A1 | 7/2011 | |
| WO | WO 2011/119484 A1 | 9/2011 | |
| WO | WO 2011157966 A1 | 12/2011 | |
| WO | WO 2013/049830 A2 | 4/2013 | |
| WO | WO 2013/156493 A1 | 10/2013 | |
| WO | WO 2014200910 A2 | 12/2014 | |
| WO | WO 2015074048 A1 | 5/2015 | |
| WO | WO-2016025516 A1 * | 2/2016 | ........... C07K 14/415 |
| WO | WO 2016/204841 A1 | 12/2016 | |
| WO | WO 2017/100421 A1 | 6/2017 | |
| WO | WO 2017189963 A1 | 11/2017 | |
| WO | WO 2018/071640 A1 | 4/2018 | |

OTHER PUBLICATIONS

Christensen, T., "A Qualitative Test for Monitoring Coupling Completeness in Solid Phase Peptide Synthesis Using Chloranil," Acta Chem. Scand., 33B, pp. 763-766 (1979).

Davis, J. et al. "MBNL1-mediated regulation of differentiation RNAs promotes myofibroblast transformation and the fibrotic response," Nature Communications, vol. 6: 10084, pp. 1-14 (2015).

Goldberg, A. et al. "Skin Rejuvenation with Non-Invasive Pulsed Electric Fields," Nature Scientific Reports, vol. 5:10187, pp. 1-18 (2015).

Hipler, U.C, et al., "Biofunctional Textiles and the Skin" in Curr. Probl. Dermatol. v.33, pp. 35-41 (Hipler U.C. and Elsner P., eds.) S. Karger AG, Basel, Switzerland (2006).

Jennings, J.A. "Regulation of gene expression in response to continuous low intensity direct current electrical fields," Doctoral Thesis, Birmingham Alabama, pp. 1-208 (2007) (Abstract only).

Kaiser, E., et al., "Color test for detection of free terminal amino groups in the solid-phase synthesis of peptides," Anal. Biochem., 34, pp. 595-598 (1970).

Kern, H., et al. "Electrical stimulation counteracts muscle decline in seniors," Frontiers in Aging Neuroscience, vol. 6 (189), pp. 1-11 (2014).

Kullmann, W., "Proteases as catalysts for enzymic syntheses of opioid peptides," J. Biol. Chem., 255(17), pp. 8234-8238 (1980).

Lionakis, et al., "Development of a Ligand-Directed Approach to Study the Pathogenesis of Invasive Aspergillosis," Infection and Immunity, American Society for Microbiology, vol. 73, No. 11, pp. 7747-7758 (Nov. 2005).

Lloyd-Williams, P., et al., "Chemical Approaches to the Synthesis of Peptides and Proteins," pp. 19-93, CRC, synthesis in solution, enzymatic synthesis, Boca Raton, FL, USA (1997).

Lloyd-Williams, P., et al., "Convergent Solid-Phase Peptide Synthesis," Tetrahedron, 49(48), pp. 11065-11133 (1993).

Malatesta, M. et al., "Muscleblind-like1 undergoes ectopic relocation in the nuclei of skeletal muscles in myotonic dystrophy and sarcopenia," European Journal of Histochemistry, vol. 57:e15, pp. 86-92 (2013).

Malatesta, M. et al. "RNA transcription and maturation in skeletal muscle cells are similarly impaired in myotonic dystrophy and sarcopenia: the ultrastructural evidence", (2014), Frontiers in Aging Neuroscience, vol. 6(196), pp. 1-6.

Malcolm, R.K., et al., "Controlled release of a model antibacterial drug from a novel self-lubricating silicone biomaterial," J. Cont. Release, 97(2), pp. 313-320 (2004).

Matsueda, G.R., et al., "A p-methylbenzhydrylamine resin for improved solid-phase synthesis of peptide amides," Peptides, 2, pp. 45-50 (1981).

Nelson, G., "Application of microencapsulation in textiles," Int. J. Pharm., 242(1-2), pp. 55-62 (2002).

Rink, H., "Solid-phase synthesis of protected peptide fragments using a trialkoxy-diphenyl-methylester resin," Tetrahedron Lett., 28, pp. 3787-3790 (1987).

Roberts, D.C., et al., "Unusual amino acids in peptide synthesis," in The Peptides, vol. 5, Chapter VI, pp. 341-449 (Gross E. and Meienhofer J., Eds.) Academic Press, New York, USA (1983).

Schaab, C.K., "Impregnating Fabrics with Microcapsules," HAPPI, pp. 84-86 (May 1986).

Saniee, F. et al. "Consider of Micro-Current's effect to variation of Facial Wrinkle trend, Randomized Clinical Trial Study," Life Science, vol. 9(3), pp. 1184-1189 (2012).

Stewart, J.M., et al., "Solid Phase Peptide Synthesis," 2nd edition, pp. 1-20, Pierce Chemical Company, Rockford, Illinois (1984).

Wang, S.S., "p-Alkoxybenzyl Alcohol Resin and p-Alkoxybenzyloxycarbonylhydrazide Resin for Solid Phase Synthesis of Protected Peptide Fragments," J. Am. Chem. Soc., 95, pp. 1328-1333 (1973).

Wilkinson, et al., "Harry's Cosmeticology," Seventh edition, pp. 50-73 and 757-799 (Wilkinson J.B., Moore R.J., eds.) Longman House, Essex, GB (1982).

CTFA International Cosmetic Ingredient Dictionary and Handbook, 12th Edition, vol. 3, pp. 3040-3065 (2008).

IUPAC-IUB Joint Commission on Biochemical Nomenclature (JCBN), Nomenclature and Symbolism for Amino Acids and Peptides, Recommendations 1983, Eur J. Biochem., 138, 9-37 (1984).

Varani, J. et al. "Decreased Collagen Production in Chronologically Aged Skin: Roles of Age-Dependent Alteration in Fibroblast Function and Defective Mechanical Stimulation," American Journal of Pathology, vol. 168 (6), pp. 1861-1868 (2006).

Wu, Jing-Tao et al., "Protein Digest Analysis by Pressurized Capillary Electrochromatography Using an Ion Trap Storage / Reflectron Time-of-Flight Mass Detector" Analytical Chemistry, vol. 69, No. 15, pp. 2-7 (1997).

* cited by examiner

COMPOUNDS USEFUL FOR THE TREATMENT AND/OR CARE OF THE SKIN, HAIR, NAILS AND/OR MUCOUS MEMBRANES

This application claims the priority of International Application PCT/IB2020/051021, filed Feb. 10, 2020, and EP 19382092.5, filed Feb. 10, 2019, from which the PCT application claims priority, the disclosures of which are incorporated herein in their entireties by reference.

FIELD OF THE INVENTION

The invention relates to compounds useful for the treatment and/or care of the skin, hair, nails and/or mucous membranes. In particular, the compounds are useful for the prevention of skin aging and, in particular, for the treatment and/or prevention of skin wrinkles, the treatment and/or prevention of a sagging appearance of the skin, and/or the reduction and/or prevention of facial asymmetry. The invention extends to compositions comprising the compounds and methods of treatment using the compounds.

BACKGROUND OF THE INVENTION

The effects of aging play a major role in skin appearance. The most striking signs of facial aging are wrinkles and a sagging appearance of the face. With the passing of time: the epidermis and connective tissue of the skin become weak; facial muscular firmness diminishes; the epidermis begins to loosen and drop; the natural folds in the skin in the cheek, neck, and chin area change; and there is a redistribution and loss of facial fat.

In particular, a loss of facial muscular firmness is associated with muscle aging. Muscle aging is a well-known process which can start in humans when they are around 40 years old and it accelerates in later years. The resultant loss of muscle mass (muscle tone) can give the face a loose, sagging appearance. The jawline loses its contour, and the profile of the face becomes less defined.

Different methods to improve facial muscular firmness have been proposed. One of the most popular methods for reducing facial sagging is the face-lift. The face-lift, also known as rhytidectomy, is a cosmetic surgical procedure to reduce the sagging or folds of skin on the cheeks and jawline as well as other changes in the shape of the face that take place with age. During a face-lift, a flap of skin on each side of the face is pulled back, and tissues below the skin are surgically altered to return the contour of the face to a more youthful shape. Nevertheless, face-lifts can be associated with different complications and risks. Like any other type of surgery, a face-lift poses a risk of bleeding, infection and an adverse reaction to anesthesia. Some other risks include hematoma, scarring, nerve injury, hair loss and skin loss, among others. Moreover, the results of face-lifts are not permanent. With age, the facial skin may begin to droop again. In general, a face-lift can be expected to last 10 years.

Not surprisingly, there is a growing interest in alternative non-invasive methods to reduce face sagging. One of the most promising ones is electrical stimulation. Electronic muscle stimulation (EMS) has been used as an alternative intervention to improve muscle recovery, improvement of muscle structure and function in multiple biomedical fields. [Kern, H. et al "Electrical stimulation counteracts muscle decline in seniors", (2014), Frontiers in Aging Neuroscience, Vol 6(189), pp. 11-11]. There are four main types of treatment, that differ in the type of electric current they use: galvanic treatment, neuromuscular electrical stimulation (NMES) (also known as Faradic treatment), micro-current electrical neuromuscular stimulation (MENS) and high-frequency treatment.

MENS is distinguished by the use of extremely small electrical currents (i.e., millionths of an amp, e.g., 300-500 μA) which are hardly perceptible, but mimic the body's own bio-electric currents. MENS is thus not designed for medical use, but for cosmetic non-therapeutic beauty treatment for improving skin rejuvenation as an effective, non-invasive, and inexpensive technique to fight against skin aging appearance [Goldbert, A. et al. "Skin Rejuvenation with Non-Invasive Pulsed Electric Fields", (2015), Nature Scientific Reports, Vol 5(10187), pp. 1-18; Seniee, F. et al. "Consider of Micro-Current's effect to variation of Facial Wrinkle trend, Randomized Clinical Trial Study", (2012), Life Science Journal Vol 9(3), pp. 1184-1189]. By stimulating the skin cells in a particular way, it is possible to reduce the wrinkles and sagging of the skin.

On a cellular level MENS is also known to stimulate collagen and elastin production. Collagen is the most abundant protein in the connective tissue of the skin and forms a mesh-like structure that helps to support new cells as they grow, while providing needed flexibility. One of well-recognized characteristics of aging is sagging of the skin. Increase of collagen synthesis is considered beneficial to reduce aging signs. Collagen synthesis declines with aging leading to a loss of skin firming and contributing to appearance of wrinkles in older people [Varani, J. et al. "Decreased Collagen Production in Chronologically Aged Skin: Roles of Age-Dependent Alteration in Fibroblast Function and Defective Mechanical Stimulation", (2006), American Journal of Pathology, Vol. 168 (6), pp. 1861-1868]. Therefore, MENS can improve the firmness and toning of facial skin.

Nevertheless, treatment using MENS attracts some disadvantages. For instance, the intensive levels of the electrical currents may depend on individual skin thickness. Generally, if health is deteriorated or the physical state changes, the microcurrent flowing within the human body becomes weak. Skin thickness is subjected to changes of age or external factors, and thus there is high intra- and interindividual variability. In some cases, poor electrical contact between the electrode and the surface being treated results in the user feeling discomfort and pain, and in extreme cases can result in skin irritation. Some MENS devices use electrodes and adhesive gels to improve the conductivity, but this is expensive and inconvenient on, e.g., the face because there is no allowance for movement of the electrodes once they have been positioned. Further, depending on the device, it can be difficult to precisely follow the outline of the surfaces of the body being treated and this is a problem as the stimuli should be able to address to a precise area. For example, some devices require the use of a mirror in order to be able to locate the wands of the device on the appropriate parts of the face and squeeze or lengthen the skin. Finally, some potential users have a negative preconception of MENS treatment, i.e., prejudices against using electricity on their face, for example, as a daily beauty treatment.

There is a need to provide alternative methods for alleviating or preventing the signs of skin aging for example, for improving skin tone and firmness and/or for reducing a sagging appearance of the skin. There is a need to provide such a method that overcomes the problems associated with known methods such as face-lifts or MENS. There is a need to find novel active compounds that can alleviate or prevent the signs of skin aging. In particular, there is a need to find novel active compounds that can prevent or reduce skin wrinkles and/or a sagging appearance of the face.

The present invention sets out to meet some or all of these needs and to solve some or all of the above-identified problems.

SUMMARY OF THE INVENTION

In a first aspect, the invention provides a compound represented by formula (I):

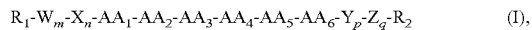

$$R_1\text{-}W_m\text{-}X_n\text{-}AA_1\text{-}AA_2\text{-}AA_3\text{-}AA_4\text{-}AA_5\text{-}AA_6\text{-}Y_p\text{-}Z_q\text{-}R_2 \quad (I),$$

a stereoisomer and/or cosmetically acceptable salt thereof, wherein:
$AA_1$ is Asp, Glu, Asn, Gln, Ala, Gly or no amino acid;
$AA_2$ is Val, Ile, Leu or Ala;
$AA_3$ is Tyr, Phe, Trp, Lys, Arg or His;
$AA_4$ is Lys, Arg, His, Pro or Val;
$AA_5$ is Asn, Asp, Gln or no amino acid;
$AA_6$ is Thr, Ala, Ser or no amino acid;
W, X, Y and Z are each independently any amino acid;
m, n, p and q are each independently 0 or 1;
m+n+p+q is less than or equal to 2;
$R_1$ is selected from the group consisting of H, a polymer derived from polyethylene glycol, a non-cyclic aliphatic group, alicyclyl, heterocyclyl, heteroarylalkyl, aryl, aralkyl and $R_5$—CO—, wherein $R_5$ is selected from the group consisting of H, a non-cyclic aliphatic group, alicyclyl, aryl, aralkyl, heterocyclyl and heteroarylalkyl;
$R_2$ is selected from the group consisting of —$NR_3R_4$, —$OR_3$, —$SR_3$, wherein $R_3$ and $R_4$ are independently selected from a group consisting of H, a polymer derived from polyethylene glycol, a non-cyclic aliphatic group, alicyclyl, heterocyclyl, heteroarylalkyl, aryl and aralkyl; and
$R_1$ and $R_2$ are not amino acids.

In particular, the invention provides compounds represented by formula (I) wherein, when $AA_5$ Asn, Asp or Gln, $AA_1$ is Ala, Gly or no amino acid; $AA_2$ is Val, Ile or Leu; $AA_3$ is Lys, Arg or His; $AA_4$ is Pro or Val; $AA_6$ is Thr, Ala, Ser or no amino acid, with the proviso that $AA_1$ is different from $AA_6$. Optionally, or in addition, the invention provides compounds represented by formula (I) wherein, when $AA_5$ is no amino acid, $AA_1$ is Asp, Glu, Asn or Gln; $AA_2$ is Val, Ile, Leu or Ala; $AA_3$ is Tyr, Phe or Trp; $AA_4$ is Lys, Arg or His; and $AA_6$ is no amino acid.

It has been found that compounds of the invention are effective in upregulating the expression of muscle blind-like 1 (MBNL1). MBNL1 is a highly conserved RNA-binding protein, which plays an important role in the process of muscle differentiation and maintenance. An increase of MBNL1 protein in fibroblast cells activates their transdifferentiation process to myofibroblasts, a cell-type able to release a higher amount of extracellular matrix proteins, like collagen, elastin and fibronectin. This increase in myofibroblasts results in an increase in collagen in the skin, resulting in a firming effect on the skin. Thus, the compounds of the invention are useful for alleviating and/or preventing problems associated with loss of muscle mass (muscle tone) due to muscle aging, such as an appearance of facial sagging. Further, the compounds of the invention can be used for a beauty treatment that exerts a lifting effect of the skin through chemical mechanisms, similar to the effect of physical treatments such as electric stimulation microcurrents, but without the inconveniences of the latter. In addition, compounds of the invention have been found to be effective in inhibiting noradrenaline release in the skin and in increasing the amount of lipids in adipose cells. These further indicate their usefulness as skin antiaging agents.

In another aspect, the invention provides a cosmetic composition comprising a compound of formula (I), its stereoisomers and/or its cosmetically acceptable salts, together with at least one cosmetically acceptable excipient or adjuvant.

In another aspect, the invention provides the use of a compound of formula (I), its stereoisomers and/or its cosmetically acceptable salts, or a composition comprising a compound of formula (I), its stereoisomers and/or its cosmetically acceptable salts, for the treatment and/or care of the skin, hair, nails and/or mucous membranes. In particular, the invention provides the use of a compound of formula (I), its stereoisomers and/or its cosmetically acceptable salts, or a cosmetic composition comprising a compound of formula (I), its stereoisomers and/or its cosmetically acceptable salts, for the cosmetic, non-therapeutic treatment and/or care of the skin, hair, nails and/or mucous membranes. The cosmetic, non-therapeutic treatment and/or care can be: the prevention or the treatment of the symptoms of skin aging; the treatment and/or prevention of skin wrinkles; the stimulation of collagen synthesis and/or prevention of collagen loss; the improvement or maintenance of skin firmness; the treatment and/or prevention of a sagging appearance of the skin; the treatment or prevention of facial asymmetry; the increase of the volume of adipose tissue; and/or the prevention and/or alleviation of effects of adipose tissue loss.

In another aspect, the invention provides a method of treatment and/or care of the skin, hair, nails and/or mucous membranes in a subject comprising administering an effective amount of a compound of formula (I), its stereoisomers and/or its cosmetically or pharmaceutically acceptable salts, or a composition comprising same, to the subject. In particular, the invention provides a method of cosmetic, non-therapeutic treatment and/or care of the skin, hair, nails and/or mucous membranes in a subject comprising administering a cosmetically effective amount of a compound of formula (I), its stereoisomers and/or its cosmetically acceptable salts, or a cosmetic composition comprising same, to the subject. Typically, the compound will be administered topically. The cosmetic, non-therapeutic treatment and/or care can be: the prevention or the treatment of the symptoms of skin aging; the treatment and/or prevention of skin wrinkles; the stimulation of collagen synthesis and/or prevention of collagen loss; the improvement or maintenance of skin firmness; the treatment and/or prevention of a sagging appearance of the skin; and/or the treatment or prevention of facial asymmetry the increase of the volume of adipose tissue; and/or the prevention and/or alleviation of effects of adipose tissue loss.

In another aspect, the invention provides a kit for use in a cosmetic, non-therapeutic method of treatment and/or care of the skin comprising:
(i) a composition comprising Botulinum toxin;
(ii) optionally a composition comprising Ac-Glu-Glu-Met-Gln-Arg-Arg-$NH_2$ (Ac-[SEQ ID NO. 41]-$NH_2$; and
(iii) a cosmetic composition comprising a compound of formula (I).

DETAILED DESCRIPTION OF THE INVENTION

Definitions

Figure 1:
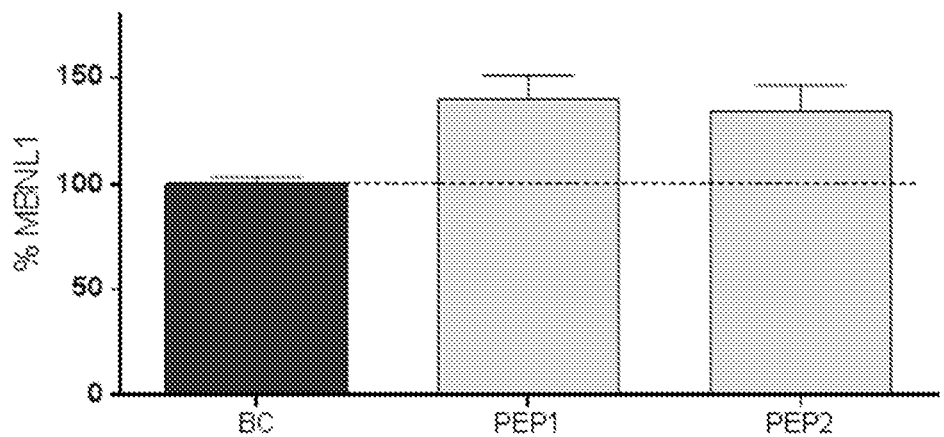
FIG. 1 shows percentages of MBNL1 protein present in human skeletal muscle cells (based on total protein content of the human skeletal muscles cells) measured using a time resolved fluorescence energy transfer assay. The measurements are made on samples of human skeletal muscles cells treated with a compound of the invention and for a control sample of human skeletal muscles cells not treated with a compound of the invention (Example 7). Abbreviations: BC, basal control.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes, mast cells, neurones and/or adipocytes among others. The term "skin" also comprises the scalp. The term "skin" includes the skin of mammals and includes human skin. Likewise, the terms "hair, nails and mucous membranes" include the hair, nails and mucous membranes of mammals, for example humans.

The term "treatment", as used herein and when it is not accompanied by the qualifications "cosmetic, non-therapeutic" refers to therapeutic methods including methods directed to the administration of a compound according to the invention to alleviate or eliminate a disease or disorder, or to reduce or eliminate one or more symptoms associated with said disease or disorder. The term "treatment", when it is not accompanied by the qualifications "cosmetic, non-therapeutic", also covers methods of therapy directed to alleviating or eliminating physiological consequences of the disease or disorder.

When the terms "treatment" and "care" are accompanied by the qualifications "cosmetic, non-therapeutic", it means that the treatment or care has the aim of improving or maintaining the aesthetic appearance of the skin, hair, nails and/or mucous membranes. In particular, the treatment can have the aim of improving cosmetic properties of the skin, hair, nails and/or mucous membranes such as, for example and not restricted to, the level of hydration, elasticity, firmness, shine, tone or texture, which properties affect the aesthetic appearance of the skin, hair, nails and/or mucous membranes. The term "care" in the context of this specification refers to the maintenance of properties of the skin, hair, nails and/or mucous membranes. Said properties are subject to being improved or maintained by cosmetic treatment and/or care of the skin, hair, nails and/or mucous membranes both in healthy subjects as well as in those which present diseases and/or disorders of the skin, hair, nails and/or mucous membranes.

The term "inhibition", as used in this invention, refers to the ability of a compound of the invention to delay or hinder the appearance or development of a disease or disorder, or to delay or hinder the change in a cosmetic property of the skin, mucous membranes and/or hair. The term "inhibition", " " refers to the ability of a compound of the invention to inhibit the appearance or development of a disease or disorder, or to inhibit the change in a cosmetic property of the skin, hair, nails and/or mucous membranes.

In the context of this invention, the term "aging" refers to the changes experienced by the skin as the result of intrinsic aging process (i.e., chronoaging) or extrinsic skin aging process induced by environmental factors (i.e., through exposure to the sun (photoaging) or to environmental agents such as tobacco smoke, extreme climatic conditions of cold or wind, chemical contaminants or pollutants). In the context of the invention, aging includes all the external visible and/or perceptible changes through touch, such as and not restricted to, the development of discontinuities on the skin such as wrinkles, fine lines, expression lines, stretch marks, furrows, irregularities or roughness, increase in the size of pores, loss of hydration, loss of elasticity, loss of firmness, loss of smoothness, loss of the capacity to recover from deformation, loss of resilience, sagging of the skin such as sagging cheeks, the appearance of bags under the eyes or the appearance of a double chin, among others, changes to the color of the skin such as marks, reddening, bags or the appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and it presents the same physical characteristics as aging, such as and not restricted to, flaccidity, sagging, changes to the color or irregularities in the pigmentation, abnormal and/or excessive keratinization. The sum of various environmental factors such as exposure to tobacco smoke, exposure to pollution, and climatic conditions such as cold and/or wind also contribute to the aging of the skin.

In this description, the abbreviations used for amino acids follow the rules of IUPAC-IUB Commission of Biochemical Nomenclature specified in *Eur. J. Biochem.*, (1984), 138, 9-37. Thus, for example, Gly represents $NH_2—CH_2—COOH$, Gly- represents $NH_2—CH_2—CO—$, -Gly represents $—NH—CH_2—COOH$ and -Gly- represents $—NH—CH_2—CO—$. Therefore, the hyphen, which represents the peptide bond, eliminates the OH in the 1-carboxyl group of the amino acid (represented here in the conventional non-ionized form) when situated to the right of the symbol, and eliminates the H of the 2-amino group of the amino acid when situated to the left of the symbol; both modifications can be applied to the same symbol (see Table 1).

TABLE 1

Structures of the amino acid residues, their nomenclature in three-letter code and nomenclature for the amino acids in one letter code

| Name | Residue | Symbol | Residue |
|---|---|---|---|
| Arginyl -Arg- R | | Lysyl -Lys- K | |
| Glutaminyl -Gln- Q | | Tryptophyl -Trp- W | |
| Asparaginyl -Asn- N | | Phenylalanyl -Phe- F | |
| Leucyl -Leu- L | | Aspartyl -Asp- D | |
| Alanyl -Ala- A | | Valyl -Val- V | |

TABLE 1-continued

Structures of the amino acid residues, their nomenclature in three-letter code and nomenclature for the amino acids in one letter code

| Name | Residue | Symbol | Residue |
|---|---|---|---|
| Isoleucyl -Ile- I | | Glycyl -Gly- G | |
| Histidyl -His- H | | Prolyl -Pro- P | |
| Tyrosyl -Tyr- Y | | Seryl -Ser- S | |
| Threonyl -Thr- T | | | |

As used herein, the term "non-cyclic aliphatic group" includes linear (i.e., straight and unbranched) or branched, saturated or unsaturated hydrocarbyl groups such as alkyl, alkenyl and alkynyl. The non-cyclic aliphatic group may be substituted (mono- or poly-) or unsubstituted.

As used herein, the term "alkyl" includes both saturated linear and branched alkyl groups, which may be substituted (mono- or poly-) or unsubstituted. The alkyl group is bound to the rest of the molecule by a single bond. The alkyl group has from 1 to 24, preferably from 1 to 16, more preferably from 1 to 14, even more preferably from 1 to 12, yet more preferably 1, 2, 3, 4, 5 or 6 carbon atoms. The term "alkyl" includes, for example, methyl, ethyl, isopropyl, isobutyl, tert-butyl, 2-methylbutyl, heptyl, 5-methylhexyl, 2-ethylhexyl, octyl, decyl, dodecyl, lauryl, hexadecyl, octadecyl and amyl.

As used herein, the term "alkenyl" refers to a group containing one or more double carbon-carbon bonds and which may be linear or branched and substituted (mono- or poly-) or unsubstituted. Preferably it has 1, 2 or 3 double carbon-carbon bonds. If more than one double carbon-carbon bond is present, the double bonds may be conjugated or not conjugated. Preferably the alkenyl group has from 2 to 24, preferably from 2 to 16, more preferably from 2 to 14, even more preferably from 2 to 12, yet more preferably 2, 3, 4, 5 or 6 carbon atoms. The alkenyl group is bound to the rest of the molecule by a single bond. The term "alkenyl" includes, for example, vinyl (—$CH_2$=$CH_2$), allyl (—$CH_2$—CH=$CH_2$), prenyl, oleyl, linoleyl groups and similar.

The term "alkynyl" refers to a group containing one or more triple carbon-carbon bonds and which may be linear or branched, and substituted (mono- or poly-) or unsubstituted. Preferably the alkynyl group has 1, 2 or 3 triple carbon-carbon bonds. The triple bonds may be conjugated or not conjugated. The alkynyl group has from 2 to 24, preferably from 2 to 16, more preferably from 2 to 14, even more preferably from 2 to 12, yet more preferably 2, 3, 4, 5 or 6 carbon atoms. The alkynyl group is bound to the rest of the molecule by a single bond. The term "alkynyl" includes, for example and not restricted to, ethynyl, 1-propynyl, 2-propynyl, 1-butynyl, 2-butynyl, 3-butynyl, pentynyl, such as 1-pentynyl, and similar. The alkynyl group can also contain one or more double carbon-carbon bonds, and alkynyl groups include, for example and not restricted to, but-1-en-3-ynyl and pent-4-en-1-ynyl groups, and similar.

The term "alicyclyl" is used herein to cover, for example and not restricted to, aliphatic cyclic (alicyclic) groups such as cycloalkyl or cycloalkenyl or cycloalkynyl groups. The term "alicyclyl" refers to a monoradical that contains one or more rings of carbon atoms, the rings may be saturated (e.g., cyclohexyl) or unsaturated (e.g., cyclohexenyl) provided that they are not aromatic. More specifically alicyclic groups contain three or more, from 3 to 24, from 3 to 12, or from 6 to 12, ring carbon atoms. The alicyclic group may be a monocyclic, bicyclic, or tricyclic ring system and the rings may be, for example, fused or linked by a single bond or a linking group such as a methylene or other alkylene group. The alicyclic group may be substituted (mono- or poly-) or unsubstituted. In one embodiment, the alicyclyl group is a 6 to 12 membered ring system which consists of carbon atoms and optionally contains one or two double bonds.

The term "cycloalkyl" refers to a saturated mono- or polycyclic alkyl group which may be substituted (mono- or poly-) or unsubstituted. The cycloalkyl group has from 3 to 24, preferably from 3 to 16, more preferably from 3 to 14, even more preferably from 3 to 12, yet even more preferably 3, 4, 5 or 6 carbon atoms. The cycloalkyl group is bound to the rest of the molecule by a single bond. Cycloalkyl groups include, for example and not restricted to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and similar.

The term "cycloalkenyl" refers to a non-aromatic mono- or polycyclic alkenyl group which may be substituted (mono- or poly-) or unsubstituted. The cycloalkenyl group has from 5 to 24, preferably from 5 to 16, more preferably from 5 to 14, even more preferably from 5 to 12, yet more preferably 5 or 6 carbon atoms. The cycloalkenyl group is bound to the rest of the molecule by a single bond. Preferably the cycloalkenyl group contains 1, 2 or 3 double carbon-carbon bonds. If more than one double carbon-carbon bond is present, the double bonds may be conjugated or not conjugated. Cycloalkenyl groups include, for example and not restricted to, the cyclopent-1-en-1-yl group and similar.

The term "cycloalkynyl" refers to a non-aromatic mono- or polycyclic alkynyl group which may be substituted (mono- or poly-) or unsubstituted. The cycloalkynyl group has from 8 to 24, preferably from 8 to 16, more preferably from 8 to 14, even more preferably from 8 to 12, yet even more preferably 8 or 9 carbon atoms and is bound to the rest of the molecule by a single bond. Preferably the cycloalkynyl group contains 1, 2 or 3 triple carbon-carbon bonds, conjugated or not conjugated. Cycloalkynyl groups include, for example and not restricted to, the cyclooct-2-yn-1-yl group and similar. Cycloalkynyl groups can also contain one or more double carbon-carbon bonds, including, for example and not restricted to, the cyclooct-4-en-2-ynyl group and similar.

As used herein, the term "heterocyclyl" or "heterocyclic" refers to a hydrocarbon ring system of 3 to 10 members, wherein one or more of the atoms in the ring or rings is a heteroatom (i.e., not a carbon atom). Thus "heterocyclyl" or "heterocyclic" refers a cyclic group in which the ring atoms consist of carbon and one or more heteroatoms. To satisfy valence, the heteroatom may be bonded to H or substituent groups. Preferably from 1, 2 or 3 of the ring carbon atoms are heteroatoms. Each heteroatom can be independently selected from the group consisting of O, N, S, P and B, or the group consisting of O, N, and S. The heterocyclyl group may be substituted (mono- or poly-) or unsubstituted. The heterocyclyl group may be a monocyclic, bicyclic, or tricyclic ring system and the rings may be, for example, fused or linked by a single bond or a linking group such as a methylene or other alkylene group. Nitrogen, carbon or sulfur atoms present in the heterocyclyl radical may be optionally oxidized and the nitrogen atom may be optionally quaternized. The heterocyclyl radical may be unsaturated or partially or fully saturated. The heterocyclyl radical may be aliphatic or aromatic. In one embodiment, the heterocyclyl is aliphatic (also known as heteroalicyclyl) and is a 3 to 10 membered ring system where the atoms of the ring or rings consist of carbon atoms and from 1 to 4, or 1, 2 or 3 heteroatoms. In one embodiment, the heterocyclyl group is a 6 to 10 membered ring system where the atoms of the ring or rings consist of carbon atoms and from 1 to 4 heteroatoms and where the ring system optionally contains one or two double bonds. In one embodiment, the heterocyclyl is aromatic (also known as heteroaryl) and is a 6 to 10 membered ring system where the atoms of the ring or rings consist of carbon atoms and from 1 to 4, or 1, 2 or 3 heteroatoms. The greatest preference is for the term heterocyclyl to refer to a ring of 5 or 6 members. Examples of saturated heteroalicyclyl groups are dioxane, piperidine, piperazine, pyrrolidine, morpholine and thiomorpholine. Examples of aromatic heterocyclyl groups are pyridine, pyrrol, furan, thiophene, benzofuran, imidazoline, quinolein, quinoline, pyridazine and naphthyridine.

The term "aryl group" refers to an aromatic group which has from 6 to 30, preferably from 6 to 18, more preferably between 6 and 10, yet even more preferably 6 or 10 carbon atoms. The aryl group can comprise 1, 2, 3 or 4 aromatic rings, which may be linked by a carbon-carbon bond or fused together and includes, for example and not restricted to, phenyl, naphthyl, diphenyl, indenyl, phenanthryl or antranyl among others. The aryl group may be substituted (mono- or poly-) or unsubstituted.

The term "aralkyl group" refers to an alkyl group substituted by an aromatic group, with from 7 to 24 carbon atoms and including, for example and not restricted to, —(CH$_2$)$_{1-6}$-phenyl, —(CH$_2$)$_{1-6}$-(1-naphthyl), —(CH$_2$)$_{1-6}$-(2-naphthyl), —(CH$_2$)$_{1-6}$-CH(phenyl)$_2$ and similar.

The term "heteroarylalkyl" refers to an alkyl group substituted by a heteroaryl (also known as aromatic heterocyclic) group as defined above, the alkyl group having from 1 to 6 carbon atoms and the heteroaryl group having from 2 to 24 carbon atoms and from 1 to 3 heteroatoms. Heteroarylalkyl groups include, for example and not restricted to, —(CH$_2$)$_{1-6}$-imidazolyl, —(CH$_2$)$_{1-6}$-triazolyl, —(CH$_2$)$_{1-6}$-thienyl, —(CH$_2$)$_{1-6}$-furyl, —(CH$_2$)$_{1-6}$-pyrrolidinyl and similar.

As is understood in this technical field, there may be a certain degree of substitution of the aforementioned groups. In particular, there can be substitution in any of the groups identified above where it is explicitly stated. The substituted groups (radicals) referred to above are groups (or radicals) which are substituted in one or more positions available by one or more substituents. Preferably substitution is in the 1, 2 or 3 positions, more preferably in the 1 or 2 positions, yet even more preferably in the 1 position. Suitable substituents include, for example and not restricted to: C$_1$-C$_4$ alkyl; hydroxyl; C$_1$-C$_4$ alkoxyl; amino; amino-C$_1$-C$_4$alkyl; C$_1$-C$_4$ carbonyloxyl; C$_1$-C$_4$ oxycarbonyl; halogen such as fluoride, chlorine, bromine and iodine; cyano; nitro; azide; C$_1$-C$_4$ alkylsulfonyl; thiol; C$_1$-C$_4$ alkylthio; aryloxy such as phenoxyl; —NR$_b$(C═NR$_b$)NR$_b$R$_c$; wherein R$_b$ and R$_c$ are independently selected from the group formed by H, C$_1$-C$_4$ alkyl, C$_2$-C$_4$ alkenyl, alkynyl, C$_3$-C$_{10}$ cycloalkyl, C$_6$-C$_{18}$ aryl, C$_7$-C$_{17}$ aralkyl, heterocyclyl of 3-10 members or protective group of the amino group.

As will be understood and, as indicated above, when it is stated herein that R is alkyl, alkenyl, alkynyl, alicyclyl, cycloalkyl, cycloalkenyl, cycloalkenyl, heterocyclyl, heterocyclic, heteroarylalkyl, aryl or aralkyl, etc, it is meant that R is such a group. For example, when it is stated R is alkyl, it is mean that R is an alkyl group. As used herein, the term "comprising", which is inclusive or open-ended and does not exclude additional unrecited elements or method steps, is intended to encompass as alternative embodiments, the phrases "consisting essentially of" and "consisting of" where "consisting of" excludes any element or step not specified and "consisting essentially of" permits the inclusion of additional unrecited elements or steps that do not materially affect the essential or basic and novel characteristics of the composition or method under consideration.

Compounds of the Invention

A first aspect of the invention relates to a compound of formula (I)

$$R_1\text{-}W_m\text{-}X_n\text{-}AA_1\text{-}AA_2\text{-}AA_3\text{-}AA_4\text{-}AA_5\text{-}AA_6\text{-}Y_p\text{-}Z_q\text{-}R_2 \qquad (I),$$

or a stereoisomer and/or cosmetically acceptable salt thereof, wherein:

$AA_1$ is Asp, Glu, Asn, Gln, Ala, Gly or no amino acid;
$AA_2$ is Val, Ile, Leu or Ala;
$AA_3$ is Tyr, Phe, Trp, Lys, Arg or His;
$AA_4$ is Lys, Arg, His, Pro or Val;
$AA_5$ is Asn, Asp, Gln or no amino acid;
$AA_6$ is Thr, Ala, Ser or no amino acid;
W, X, Y and Z are each independently any amino acid;
m, n, p and q are each independently 0 or 1;
m+n+p+q is less than or equal to 2;
$R_1$ is selected from the group consisting of H, a polymer derived from polyethylene glycol, a non-cyclic aliphatic group, alicyclyl, heterocyclyl, heteroarylalkyl, aryl, aralkyl and $R_5$—CO—, wherein $R_5$ is selected from the group consisting of H, a non-cyclic aliphatic group, alicyclyl, aryl, aralkyl, heterocyclyl and heteroarylalkyl;
$R_2$ is selected from the group consisting of —$NR_3R_4$, —$OR_3$, —$SR_3$, wherein $R_3$ and $R_4$ are independently selected from a group consisting of H, a polymer derived from polyethylene glycol, a non-cyclic aliphatic group, alicyclyl, heterocyclyl, heteroarylalkyl, aryl and aralkyl; and
$R_1$ and $R_2$ are not amino acids.

Advantageously, compounds of formula (I) have been found to upregulate MBNL1 protein in skin and skin muscle cells.

The compound of formula (I) is a peptide which comprises 3, 4, 5, 6, 7 or 8 amino acids linked in a chain. $R_1$ is bound to the amino terminal end (N-terminal) of the peptide and $R_2$ is bound to the carboxy-terminal end (C-terminal) of the peptide.

$R_1$ can be selected from the group consisting of H, a polymer derived from polyethylene glycol with a molecular weight comprised between 200 and 35000 Daltons and $R_5$—CO—, wherein $R_5$ is selected from the group consisting of $C_1$-$C_{24}$ alkyl, $C_2$-$C_{24}$ alkenyl, $C_2$-$C_{24}$ alkynyl, $C_3$-$C_{24}$ cycloalkyl, $C_5$-$C_{24}$ cycloalkenyl, $C_8$-$C_{24}$ cycloalkynyl, $C_8$-$C_{30}$ aryl, $C_7$-$C_{24}$ aralkyl, 3-10 membered heterocyclyl ring, and a heteroarylalkyl containing from 2 to 24 carbon atoms and from 1 to 3 heteroatoms, wherein the alkyl group has 1 to 6 carbon atoms.

$R_1$ can be selected from the group consisting of H and $R_5$—CO—, wherein $R_5$ is selected from the group consisting of $C_1$-$C_{18}$ alkyl, $C_2$-$C_{24}$ alkenyl, $C_3$-$C_{24}$ cycloalkyl or the group consisting of $C_1$-$C_{16}$ alkyl, $C_2$-$C_{18}$ alkenyl, $C_3$-$C_7$ cycloalkyl. The $R_5$—CO— group includes alkanoyl groups such as acetyl ($CH_3$—CO—, which is abbreviated herein as "Ac-"), myristoyl ($CH_3$—$(CH_2)_{12}$—CO—, which is abbreviated herein as "Myr-") and palmitoyl ($CH_3$—$(CH_2)_{14}$—CO—, which is abbreviated herein as "Palm-").

$R_1$ can be selected from the group consisting of H and acetyl, tert-butanoyl, prenyl, hexanoyl, 2-methylhexanoyl, cyclohexanecarboxyl, octanoyl, decanoyl, lauroyl, myristoyl, palmitoyl, stearoyl, oleoyl and linoleoyl.

$R_1$ can be selected from the group consisting of H and $R_5$—CO—, wherein $R_5$ is selected from the group consisting of $C_1$-$C_{16}$ alkyl or $C_2$-$C_{18}$ alkenyl.

$R_1$ can be selected from the group consisting of H and $R_5$—CO—, wherein $R_5$ is $C_1$-$C_{15}$ alkyl.

$R_1$ can be selected from the group consisting of H, acetyl and palmitoyl. Particularly, $R_1$ is H or acetyl.

$R_2$ can be selected from the group consisting of —$NR_3R_4$, —$OR_3$, —$SR_3$, wherein $R_3$ and $R_4$ are independently selected from the group formed by H, a polymer derived from polyethylene glycol, $C_1$-$C_{24}$ alkyl, $C_2$-$C_{24}$ alkenyl, $C_2$-$C_{24}$ alkynyl, $C_3$-$C_{24}$ cycloalkyl, $C_5$-$C_{24}$ cycloalkenyl, $C_8$-$C_{24}$ cycloalkynyl, $C_6$-$C_{30}$ aryl, $C_7$-$C_{24}$ aralkyl, 3-10 membered heterocyclyl ring, and heteroarylalkyl containing from 2 to 24 carbon atoms and from 1 to 3 heteroatoms, wherein the alkyl group has 1 to 6 carbon atoms. Optionally, $R_3$ and $R_4$ can be joined by a saturated or unsaturated carbon-carbon bond, forming a ring with the nitrogen atom.

$R_2$ can be —$NR_3R_4$ or —$OR_3$. $R_3$ and $R_4$ can be independently selected from the group consisting of H, a polymer derived from polyethylene glycol with a molecular weight comprised between 200 and 35000 Daltons, methyl, ethyl, hexyl, dodecyl and hexadecyl. Alternatively, $R_3$ and $R_4$ can be independently selected from the group consisting of H and $C_1$-$C_{16}$ alkyl. In one embodiment, $R_2$ is not $OR_3$ where $R_3$ is a methyl group, i.e., $R_2$ is not $OCH_3$. In one embodiment $R_3$ is H and $R_4$ is selected from the group formed by H and $C_1$-$C_{16}$ alkyl, including methyl, ethyl, hexyl, dodecyl and hexadecyl.

$R_2$ can be selected from the group consisting of —OH, —$NH_2$ and —$NHR_4$ where $R_4$ is $C_1$-$C_{16}$ alkyl or $C_1$-$C_3$ alkyl or $C_1$-$C_2$ alkyl.

$R_2$ can be —OH or —$NH_2$. Particularly, $R_2$ is $NH_2$.

$R_1$ can be selected from the group consisting of H and $R_5$—CO—, wherein $R_5$ is selected from the group consisting of $C_1$-$C_{18}$ alkyl, $C_2$-$C_{24}$ alkenyl, $C_3$-$C_{24}$ cycloalkyl; and $R_2$ can be —$NR_3R_4$ or —$OR_3$, wherein $R_3$ and $R_4$ are independently selected from the group consisting of H and $C_1$-$C_{16}$ alkyl. In this embodiment, $R_3$ can be H and $R_4$ can be selected from the group formed by H, $C_1$-$C_{16}$ alkyl, $C_1$-$C_3$ alkyl and $C_1$-$C_2$ alkyl; for example, $R_2$ can be selected from the group consisting of —OH and —$NH_2$.

$R_1$ can be selected from the group consisting of H and acetyl, tert-butanoyl, prenyl, hexanoyl, 2-methylhexanoyl, cyclohexanecarboxyl, octanoyl, decanoyl, lauroyl, myristoyl, palmitoyl, stearoyl, oleoyl and linoleoyl; and $R_2$ can be —$NR_3R_4$ or —$OR_3$ wherein $R_3$ and $R_4$ are independently selected from the group consisting of H and $C_1$-$C_{16}$ alkyl. In this embodiment, $R_3$ can be H and $R_4$ can selected from the group formed by H, $C_1$-$C_{16}$ alkyl, $C_1$-$C_3$ alkyl and $C_1$-$C_2$ alkyl; for example, $R_2$ can be selected from the group consisting of —OH and —$NH_2$.

$R_1$ can be selected from the group consisting of H and $R_5$—CO—, wherein $R_5$ is selected from the group consisting of $C_1$-$C_{16}$ alkyl or $C_2$-$C_{18}$ alkenyl; and $R_2$ can be —$NR_3R_4$ or —$OR_3$, wherein $R_3$ and $R_4$ are independently selected from the group consisting of H and $C_1$-$C_{16}$ alkyl. In this embodiment $R_3$ can be H and $R_4$ can be selected from the group formed by H, $C_1$-$C_{16}$ alkyl, $C_1$-$C_3$ alkyl and $C_1$-$C_2$ alkyl; for example, $R_2$ can be selected from the group consisting of —OH and —$NH_2$.

$R_1$ can be selected from the group consisting of H, acetyl, myristoyl or palmitoyl; and $R_2$ can be —$NR_3R_4$ or —$OR_3$, wherein $R_3$ and $R_4$ are independently selected from the group consisting of H and $C_1$-$C_{16}$ alkyl. In this embodiment $R_3$ can be H and $R_4$ can be selected from the group formed by H, $C_1$-$C_{16}$ alkyl, $C_1$-$C_3$ alkyl and $C_1$-$C_2$ alkyl; for example, $R_2$ can be selected from the group consisting of —OH and —$NH_2$.

$R_1$ can be selected from the group consisting of H and $R_5$—CO—, wherein $R_5$ is $C_1$-$C_{15}$ alkyl and $R_2$ can be —$NR_3R_4$ or —$OR_3$, wherein $R_3$ and $R_4$ are independently selected from the group consisting of H and $C_1$-$C_{16}$ alkyl. In this embodiment $R_3$ can be H and $R_4$ can be selected from the group formed by H, $C_1$-$C_{16}$ alkyl, $C_1$-$C_3$ alkyl and $C_1$-$C_2$ alkyl; for example, $R_2$ can be selected from the group consisting of —OH and —$NH_2$.

$R_1$ can be selected from the group consisting of H, acetyl and palmitoyl, and $R_2$ can be —$NR_3R_4$ or —$OR_3$, wherein $R_3$ and $R_4$ are independently selected from the group consisting of H and $C_1$-$C_{16}$ alkyl. In this embodiment $R_3$ can be H and $R_4$ can be selected from the group formed by H, $C_1$-$C_{16}$ alkyl, $C_1$-$C_3$ alkyl and $C_1$-$C_2$ alkyl; for example, $R_2$ can be selected from the group consisting of —OH and —$NH_2$.

$R_1$ can be selected from the group consisting of H and acetyl, and $R_2$ can be —$NR_3R_4$ or —$OR_3$, wherein $R_3$ and $R_4$ are independently selected from the group consisting of H and $C_1$-$C_{16}$ alkyl. In this embodiment $R_3$ can be H and $R_4$ can be selected from the group formed by H, $C_1$-$C_{16}$ alkyl, $C_1$-$C_3$ alkyl and $C_1$-$C_2$ alkyl; for example, $R_2$ can be selected from the group consisting of —OH and —$NH_2$.

$R_1$ can be selected from the group consisting of H and acetyl, and $R_2$ can be —$NR_3R_4$ wherein $R_3$ and $R_4$ are independently selected from the group consisting of H and $C_1$-$C_{16}$ alkyl. In this embodiment $R_3$ can be H and $R_4$ can be selected from the group formed by H, $C_1$-$C_{16}$ alkyl, $C_1$-$C_3$ alkyl and $C_1$-$C_2$ alkyl; for example, $R_2$ can be selected from the group consisting of —$NH_2$ and —$NHR_4$ where $R_4$ is $C_1$-$C_3$ alkyl. $R_2$ can be —$NH_2$.

$R_1$ can be H and $R_2$ can be —$NH_2$.

$R_1$ can be selected from the group consisting of a substituted non-cyclic aliphatic group, substituted alicyclyl, substituted heterocyclyl, substituted heteroarylalkyl, substituted aryl, substituted aralkyl and $R_5$—CO—, wherein $R_5$ is selected from the group consisting of a substituted non-cyclic aliphatic group, substituted alicyclyl, substituted aryl, substituted aralkyl, substituted heterocyclyl and substituted heteroarylalkyl; and/or $R_2$ is —$NR_3R_4$, wherein at least one of $R_3$ and $R_4$ is selected from the group consisting of a substituted non-cyclic aliphatic group, substituted alicyclyl, substituted heterocyclyl, substituted heteroarylalkyl, substituted aryl and substituted aralkyl, or $R_2$ is —$OR_3$, or —$SR_3$, wherein $R_3$ is selected from the group consisting of a substituted non-cyclic aliphatic group, substituted alicyclyl, substituted heterocyclyl, substituted heteroarylalkyl, substituted aryl and substituted aralkyl.

In accordance with another particular embodiment the most preferred structures of the polymer derived from polyethylene glycol are the group (—$CH_2$—$CH_2$—O)$_r$—H in which r is a number comprised between 4 and 795 and the group

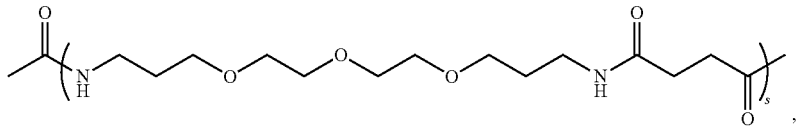

where s is a number comprised between 1 and 125.

The invention provides for a compound of formula (I), wherein at least one of: $R_1$ is not H; and $R_2$ is not OH. That is, the invention provides for a compound of formula (I) where $R_1$ is not H and/or $R_2$ is not OH.

In the compound of formula (I): $AA_1$ is selected from the group consisting of Asp, Glu, Asn, Gln, Ala, Gly and no amino acid; $AA_2$ is selected from the group consisting of Val, Ile, Leu or Ala; $AA_3$ is selected from the group consisting of Tyr, Phe, Trp, Lys, Arg and His; $AA_4$ is selected from the group consisting of Lys, Arg, His, Pro and Val; $AA_5$ is selected from the group consisting of Asn, Asp, Gln and no amino acid; and $AA_6$ is selected from the group consisting of Thr, Ala, Ser and no amino acid. When $AA_1$, for example, is no amino acid, it means that an amino acid $AA_1$ is not present in the compound.

The invention provides for a compound of formula (I) which carries the proviso that when there is an amino acid in the $AA_5$ position, i.e., when $AA_5$ is Asn, Asp or Gln, $AA_1$ is Ala, Gly or no amino acid; $AA_2$ is Val, Ile or Leu; $AA_3$ is Lys, Arg or His; $AA_4$ is Pro or Val; $AA_6$ is Thr, Ala, Ser or no amino acid; and $AA_1$ is different from $AA_6$.

The invention provides for a compound of formula (I) which carries the proviso that when there is no amino acid in the $AA_5$ position, i.e., $AA_5$ is no amino acid, $AA_1$ is Asp, Glu, Asn or Gln; $AA_2$ is Val, Ile, Leu or Ala; $AA_3$ is Tyr, Phe or Trp; $AA_4$ is Lys, Arg or His; and $AA_6$ is no amino acid.

The invention provides for a compound of formula (I) whereby when $AA_5$ is no amino acid, $AA_1$ is Asp, Glu, Asn or Gln; $AA_2$ is Val, Ile, Leu or Ala; $AA_3$ is Tyr, Phe or Trp; $AA_4$ is Lys, Arg or His; and $AA_6$ is no amino acid. In this embodiment, $AA_1$ is selected from the group consisting of Asp, Glu, Asn and Gln; $AA_2$ is selected from the group consisting of Val, Ile, Leu and Ala; $AA_3$ is selected from the group consisting of Tyr, Phe and Trp; $AA_4$ is selected from the group consisting of Lys, Arg and His; $AA_5$ is no amino acid; and $AA_6$ is no amino acid. In other words, the invention provides for a compound of formula (II):

$$R_1\text{-}W_m\text{-}X_n\text{-}AA_1\text{-}AA_2\text{-}AA_3\text{-}AA_4\text{-}Y_p\text{-}Z_q\text{-}R_2 \quad (II),$$

or a stereoisomer and/or cosmetically acceptable salt thereof, wherein:

$AA_1$ is Asp, Glu, Asn or Gln;
$AA_2$ is Val, Ile, Leu or Ala;
$AA_3$ is Tyr, Phe or Trp;
$AA_4$ is Lys, Arg or His;
W, X, Y and Z are each independently any amino acid;
m, n, p and q are each independently 0 or 1;
m+n+p+q is less than or equal to 2;
$R_1$ is selected from the group consisting of H, a polymer derived from polyethylene glycol, a non-cyclic aliphatic group, alicyclyl, heterocyclyl, heteroarylalkyl, aryl, aralkyl and $R_5$—CO—, wherein $R_5$ is selected from the group consisting of H, a non-cyclic aliphatic group, alicyclyl, aryl, aralkyl, heterocyclyl and heteroarylalkyl;
$R_2$ is selected from the group consisting of —$NR_3R_4$, —$OR_3$, —$SR_3$, wherein $R_3$ and $R_4$ are independently selected from a group consisting of H, a polymer derived from polyethylene glycol, a non-cyclic aliphatic group, alicyclyl, heterocyclyl, heteroarylalkyl, aryl and aralkyl; and $R_1$ and $R_2$ are not amino acids.

The compound of formula (II) is a peptide which comprises 4, 5 or 6 amino acids linked in a chain. $R_1$ is bound to the amino terminal end (N-terminal) of the peptide and $R_2$ is bound to the carboxy-terminal end (C-terminal) of the peptide. $R_1$ and $R_2$ are as defined above for the compound of formula (I).

The invention provides for a compound of formula (II), wherein: $AA_1$ is selected from the group consisting of Asp, Glu and Asn; $AA_2$ is selected from the group consisting of Val, Ile, Leu and Ala; $AA_3$ is selected from the group consisting of Tyr, Phe and Trp; and $AA_4$ is selected from the group consisting of Lys, Arg and His. In this embodiment, $AA_1$ can be selected from Asp and Glu.

The invention provides for a compound of formula (II), wherein: $AA_1$ is selected from the group consisting of Asp, Glu, Asn and Gln; $AA_2$ is selected from the group consisting of Val and Ile; $AA_3$ is selected from the group consisting of Tyr, Phe and Trp; and $AA_4$ is selected from the group consisting of Lys, Arg and His. In this embodiment, $AA_1$ can be selected from Asp, Glu and Asn, or selected from Asp and Glu.

The invention provides for a compound of formula (II), wherein: $AA_1$ is selected from the group consisting of Asp, Glu, Asn and Gln; $AA_2$ is selected from the group consisting of Val, Ile, Leu and Ala or the group consisting of Val and Ile; $AA_3$ is selected from the group consisting of Tyr and Phe; and $AA_4$ is selected from the group consisting of Lys, Arg and His. In this embodiment, $AA_1$ can be selected from Asp, Glu and Asn, or selected from Asp and Glu.

The invention provides for a compound of formula (II), wherein: $AA_1$ is selected from the group consisting of Asp, Glu, Asn and Gln; $AA_2$ is selected from the group consisting of Val, Ile, Leu and Ala or the group consisting of Val and Ile; $AA_3$ is selected from the group consisting of Tyr, Phe and Trp or the group consisting of Tyr and Phe; and $AA_4$ is selected from the group consisting of Lys and Arg. In this embodiment, $AA_1$ can be selected from Asp, Glu and Asn, or selected from Asp and Glu.

The invention provides for a compound of formula (II), wherein: $AA_1$ is Asp; $AA_2$ is Val; $AA_3$ is Tyr; and $AA_4$ is Lys.

The invention provides for a compound of formula (I) whereby when $AA_5$ is Asn, Asp or Gln; $AA_1$ is Ala, Gly or no amino acid; $AA_2$ is Val, Ile or Leu; $AA_3$ is Lys, Arg or His; $AA_4$ is Pro or Val; $AA_6$ is Thr, Ala, Ser or no amino acid; and $AA_1$ is different from $AA_6$. In this embodiment, $AA_1$ is selected from the group consisting of Ala, Gly and no amino acid; $AA_2$ is selected from the group consisting of Val, Ile and Leu; $AA_3$ is selected from the group consisting of Lys, Arg and His; $AA_4$ is selected from the group consisting of Pro and Val; $AA_5$ is selected from the group consisting of Asn, Asp and Gln; and $AA_6$ is selected from the group consisting of Thr, Ala, Ser and no amino acid; and $AA_1$ is different from $AA_6$. Thus, when $AA_1$ is Ala, $AA_6$ is selected from the group consisting of Thr, Ser and no amino acid. Also, when $AA_1$ is no amino acid, i.e., when an amino acid $AA_1$ is not present, amino acid $AA_6$ must be present, i.e., $AA_6$ is selected from the group consisting of Thr, Ala and Ser. Similarly, when $AA_6$ is Ala, $AA_1$ is selected from the group consisting of Gly and no amino acid. Similarly, when $AA_6$ is no amino acid, i.e., when an amino acid $AA_6$ is not present, $AA_1$ is selected from the group consisting of Ala and Gly.

Thus, the invention provides for a compound of formula (III):

$R_1$-$W_m$-$X_n$-$AA_1$-$AA_2$-$AA_3$-$AA_4$-$AA_5$-$AA_6$-$Y_p$-$Z_q$-$R_2$    (III), or a stereoisomer and/or cosmetically acceptable salt thereof, wherein:
$AA_1$ is Ala, Gly or no amino acid;
$AA_2$ is Val, Ile or Leu;
$AA_3$ is Lys, Arg or His;
$AA_4$ is Pro or Val;
$AA_5$ is Asn, Asp or Gln;
$AA_6$ is Thr, Ala, Ser or no amino acid;
$AA_1$ is different from $AA_6$;
W, X, Y and Z are each independently any amino acid;
m, n, p and q are each independently 0 or 1;
m+n+p+q is less than or equal to 2;
$R_1$ is selected from the group consisting of H, a polymer derived from polyethylene glycol, a non-cyclic aliphatic group, alicyclyl, heterocyclyl, heteroarylalkyl, aryl, aralkyl and $R_5$—CO—, wherein $R_5$ is selected from the group consisting of H, a non-cyclic aliphatic group, alicyclyl, aryl, aralkyl, heterocyclyl and heteroarylalkyl;
$R_2$ is selected from the group consisting of —$NR_3R_4$, —$OR_3$, —$SR_3$, wherein $R_3$ and $R_4$ are independently selected from a group consisting of H, a polymer derived from polyethylene glycol, a non-cyclic aliphatic group, alicyclyl, heterocyclyl, heteroarylalkyl, aryl and aralkyl; and
$R_1$ and $R_2$ are not amino acids.

The compound of formula (III) is a peptide which comprises 5, 6 or 7 amino acids linked in a chain. $R_1$ is bound to the amino terminal end (N-terminal) of the peptide and $R_2$ is bound to the carboxy-terminal end (C-terminal) of the peptide. $R_1$ and $R_2$ are as defined above for the compound of formula (I).

The invention provides for a compound of formula (III), wherein: $AA_1$ is selected from the group consisting of Ala and Gly; $AA_2$ is selected from the group consisting of Val, Ile and Leu; $AA_3$ is selected from the group consisting of Lys, Arg and His; $AA_4$ is selected from the group consisting of Pro and Val; $AA_5$ is selected from the group consisting of Asn, Asp and Gln; and $AA_6$ is selected from the group consisting of Thr, Ala, Ser and no amino acid; and $AA_1$ is different from $AA_6$.

The invention provides for a compound of formula (III), wherein: $AA_1$ is selected from the group consisting of Ala, Gly and no amino acid, or the group consisting of Ala and Gly; $AA_2$ is selected from the group consisting of Ile and Leu; $AA_3$ is selected from the group consisting of Lys, Arg and His; $AA_4$ is selected from the group consisting of Pro and Val; $AA_5$ is selected from the group consisting of Asn, Asp and Gln; and $AA_6$ is selected from the group consisting of Thr, Ala, Ser and no amino acid; and $AA_1$ is different from $AA_6$.

The invention provides for a compound of formula (III), wherein: $AA_1$ is selected from the group consisting of Ala, Gly and no amino acid, or the group consisting of Ala and Gly; $AA_2$ is selected from the group consisting of Val, Ile and Leu; $AA_3$ is selected from the group consisting of Lys and Arg; $AA_4$ is selected from the group consisting of Pro and Val; $AA_5$ is selected from the group consisting of Asn, Asp and Gln; and $AA_6$ is selected from the group consisting of Thr, Ala, Ser and no amino acid; and $AA_1$ is different from $AA_6$. In this embodiment, $AA_2$ can be Leu or Ile.

The invention provides for a compound of formula (III), wherein: $AA_1$ is selected from the group consisting of Ala, Gly and no amino acid, or the group consisting of Ala and Gly; $AA_2$ is selected from the group consisting of Val, Ile and Leu; $AA_3$ is selected from the group consisting of Lys, Arg and His; $AA_4$ is selected from the group consisting of Pro and Val; $AA_5$ is selected from the group consisting of Asn and Asp; and $AA_6$ is selected from the group consisting of Thr, Ala, Ser and no amino acid; and $AA_1$ is different from $AA_6$. In this embodiment, $AA_2$ can be selected from the group consisting of Leu and Ile; and/or $AA_3$ can be selected from the group consisting of Lys and Arg.

The invention provides for a compound of formula (III), wherein: $AA_1$ is selected from the group consisting of Ala, Gly and no amino acid, or the group consisting of Ala and Gly; $AA_2$ is selected from the group consisting of Val, Ile and Leu; $AA_3$ is selected from the group consisting of Lys, Arg and His; $AA_4$ is selected from the group consisting of Pro and Val; $AA_5$ is selected from the group consisting of Asn and Gln; and $AA_6$ is selected from the group consisting of Thr, Ala, Ser and no amino acid; and $AA_1$ is different from $AA_6$. In this embodiment, $AA_2$ can be selected from the group consisting of Leu and Ile; and/or $AA_3$ can be selected from the group consisting of Lys and Arg.

The invention provides for a compound of formula (III), wherein: $AA_1$ is selected from the group consisting of Ala, Gly and no amino acid, or the group consisting of Ala and Gly; $AA_2$ is selected from the group consisting of Val, Ile and Leu; $AA_3$ is selected from the group consisting of Lys, Arg and His; $AA_4$ is selected from the group consisting of Pro and Val; $AA_5$ is selected from the group consisting of Asn, Asp and Gln; and $AA_6$ is selected from the group consisting of Thr, Ala and Ser; and $AA_1$ is different from $AA_6$. In this embodiment, $AA_2$ can be selected from the group consisting of Leu and Ile; $AA_3$ can be selected from the group consisting of Lys and Arg; and/or $AA_5$ can be selected from the group consisting of Asn and Asp.

The invention provides for a compound of formula (III), wherein: $AA_1$ is Ala; $AA_2$ is Leu; $AA_3$ is Lys; $AA_4$ is Pro; $AA_5$ is Asn; and $AA_6$ is Thr.

The compounds of the invention can exclude Pro-Leu-Asp-Val-Tyr-Lys, i.e., the invention provides for a compound of formula (I), (II) or (III) as described above, wherein the compound is not Pro-Leu-Asp-Val-Tyr-Lys.

The compounds of the invention, i.e., the compound of formula (I), (II) or (III), can exclude Tyr-Lys-Asp-Val-Tyr-Lys, or the embodiment where m is 1 and W is Tyr; n is 1 and X is Lys; $AA_1$ is Asp; $AA_2$ is Val; $AA_3$ is Tyr; $AA_4$ is Lys; $AA_5$ is no amino acid; $AA_6$ is no amino acid; p is 0; q is 0; $R_1$ is H and $R_2$ is OH.

The compounds of the invention, i.e., the compound of formula (I), (II) or (III), can exclude Arg-Lys-Asp-Val-Tyr-Lys, or the embodiment where m is 1 and W is Arg; n is 1 and X is Lys; $AA_1$ is Asp; $AA_2$ is Val; $AA_3$ is Tyr; $AA_4$ is Lys; $AA_5$ is no amino acid; $AA_6$ is no amino acid; p is 0; q is 0; $R_1$ is H and $R_2$ is OH.

The compounds of the invention, i.e., the compound of formula (I), (II) or (III), can exclude Arg-Asn-Asp-Val-Tyr-Lys, or the embodiment where m is 1 and W is Arg; n is 1 and X is Asn; $AA_1$ is Asp; $AA_2$ is Val; $AA_3$ is Tyr; $AA_4$ is Lys $AA_5$ is no amino acid; $AA_6$ is no amino acid; p is 0; q is 0; $R_1$ is H and $R_2$ is OH.

The compounds of the invention, i.e., the compound of formula (I), (II) or (III), can exclude Arg-Asp-Val-Tyr-Lys-Gln-Asn, or the embodiment where m is 0; n is 1 and X is Arg; $AA_1$ is Asp; $AA_2$ is Val; $AA_3$ is Tyr; $AA_4$ is Lys; $AA_5$ is Gln; $AA_6$ is no amino acid; p is 1 and Y is Asn; q is 0; $R_1$ is H and $R_2$ is OH.

The compounds of the invention, i.e., the compound of formula (I), (II) or (III), can exclude Asp-Ala-Tyr-Lys, or the embodiment where m is 0; n is 0; $AA_1$ is Asp; $AA_2$ is Val; $AA_3$ is Tyr; $AA_4$ is Lys; $AA_5$ is no amino acid; $AA_6$ is no amino acid; p is 0 q is 0; $R_1$ is H and $R_2$ is OH.

The compounds of the invention, i.e., the compound of formula (I), (II) or (III), can exclude Asp-Ala-Tyr-Lys, or the embodiment where m is 0; n is 0; $AA_1$ is Asp; $AA_2$ is Val; $AA_3$ is Tyr; $AA_4$ is Lys; $AA_5$ is no amino acid; $AA_6$ is no amino acid; p is 0 q is 0; $R_1$ is H and $R_2$ is OH 0.

The compounds of the invention, i.e., the compound of formula (I), (II) or (III), can exclude Asp-Leu-Lys-Lys, or the embodiment where m is 0; n is 0; $AA_1$ is Asp; $AA_2$ is Leu; $AA_3$ is Lys; $AA_4$ is Lys; $AA_5$ is no amino acid; $AA_6$ is no amino acid; p is 0 q is 0; $R_1$ is H and $R_2$ is OH.

The compounds of the invention, i.e., the compound of formula (I), (II) or (III), can exclude His-Asp-Leu-Lys-Lys-Tyr, or the embodiment where m is 0; n is 1; X is His; $AA_1$ is Asp; $AA_2$ is Leu; $AA_3$ is Lys; $AA_4$ is Lys; $AA_5$ is no amino acid; $AA_6$ is no amino acid; p is 1; Y is Tyr; q is 0; $R_1$ is H and $R_2$ is OH.

Compounds of the invention include those selected from the group of amino acid sequences listed in Table 2, in which their sequence identifier is detailed, their stereoisomers, and/or their cosmetically or pharmaceutically acceptable salts.

TABLE 2

| Sequence | Identifier |
| --- | --- |
| Asp-Val-Tyr-Lys | SEQ ID NO. 1 |
| Ala-Leu-Lys-Pro-Asn-Thr | SEQ ID NO. 2 |
| Glu-Val-Tyr-Lys | SEQ ID NO. 3 |
| Asp-Ile-Tyr-Lys | SEQ ID NO. 4 |
| Asp-Val-Phe-Lys | SEQ ID NO. 5 |
| Asp-Val-Tyr-Arg | SEQ ID NO. 6 |
| Asn-Val-Tyr-Lys | SEQ ID NO. 7 |
| Asp-Leu-Tyr-Lys | SEQ ID NO. 8 |
| Ala-Asp-Val-Tyr-Lys | SEQ ID NO. 9 |
| Asp-Val-Tyr-Lys-Ala | SEQ ID NO. 10 |
| Ala-Glu-Val-Tyr-Lys | SEQ ID NO. 11 |
| Ala-Asp-Val-Tyr-Lys-Ala | SEQ ID NO. 12 |
| Ala-Ala-Asp-Val-Tyr-Lys | SEQ ID NO. 13 |
| Ala-Glu-Val-Tyr-Lys-Ala | SEQ ID NO. 14 |
| Glu-Ile-Tyr-Lys | SEQ ID NO. 15 |
| Ala-Glu-Ile-Tyr-Lys-Ala | SEQ ID NO. 16 |
| Glu-Ile-Phe-Lys | SEQ ID NO. 17 |
| Glu-Ile-Tyr-Arg | SEQ ID NO. 18 |
| Glu-Ile-Phe-Arg | SEQ ID NO. 19 |
| Gly-Leu-Lys-Pro-Asn-Thr | SEQ ID NO. 20 |
| Ala-Ile-Lys-Pro-Asn-Thr | SEQ ID NO. 21 |
| Ala-Leu-Arg-Pro-Asn-Thr | SEQ ID NO. 22 |
| Ala-Leu-Lys-Val-Asn-Thr | SEQ ID NO. 23 |
| Ala-Leu-Lys-Pro-Asp-Thr | SEQ ID NO. 24 |
| Ala-Leu-Lys-Pro-Asn-Ala | SEQ ID NO. 25 |

TABLE 2-continued

| Sequence | Identifier |
| --- | --- |
| Ala-Leu-Lys-Pro-Asn-Ser | SEQ ID NO. 26 |
| Ala-Ala-Leu-Lys-Pro-Asn-Thr | SEQ ID NO. 27 |
| Ala-Leu-Lys-Pro-Asn-Thr-Ala | SEQ ID NO. 28 |
| Ala-Ala-Leu-Lys-Pro-Asn-Thr-Ala | SEQ ID NO. 29 |
| Leu-Lys-Pro-Asn-Thr | SEQ ID NO. 30 |
| Ala-Leu-Lys-Pro-Asn | SEQ ID NO. 31 |
| Gly-Ile-Lys-Pro-Asn-Thr | SEQ ID NO. 32 |
| Gly-Val-Lys-Pro-Asn-Thr | SEQ ID NO. 33 |
| Ala-Ile-Arg-Pro-Asn-Thr | SEQ ID NO. 34 |
| Ala-Ile-Lys-Pro-Asp-Thr | SEQ ID NO. 35 |
| Gly-Val-Arg-Pro-Asn-Thr | SEQ ID NO. 36 |
| Ala-Ile-Arg-Pro-Asp-Thr | SEQ ID NO. 37 |
| Gly-Val-Arg-Pro-Asp-Thr | SEQ ID NO. 38 |
| Gly-Leu-Lys-Pro-Asn-Thr-Ala | SEQ ID NO. 39 |
| Ala-Leu-Lys-Pro-Gln-Thr | SEQ ID NO. 40 |

Compounds of the invention include each of the sequences of Tables 2 in which one of amino acids $AA_1$ to $AA_6$ is replaced by a replacement amino acid, wherein the replacement amino acid is selected from the alternative amino acids listed for the amino acid being replaced in formula (I), formula (II) or formula (III) above. The replacement amino acid is different from the amino acid that is being replaced. The replacement amino acid can be no amino acid. Thus the invention provides for a compound of formula (II) corresponding to SEQ ID NO. 1 in which one of amino acids $AA_1$ to $AA_4$ is replaced by an amino acid, wherein: when Asp ($AA_1$) is replaced it is replaced by Gly, Asn or Gln; when Val ($AA_2$) is replaced it is replaced by Ile, Leu or Ala; when Tyr ($AA_3$) is replaced it is replaced by Phe or Trp; and when Lys ($AA_4$) is replaced, it is replaced by Arg or Lys. Further, the invention provides for a compound of formula (III) corresponding to SEQ ID NO. 2 in which one of amino acids $AA_1$ to $AA_6$ is replaced by an amino acid, wherein: when Ala ($AA_1$) is replaced it is replaced by Gly or no amino acid; when Leu ($AA_2$) is replaced it is replaced by Ile or Val; when Lys ($AA_3$) is replaced it is replaced by Arg or His; when Pro ($AA_4$) is replaced, it is replaced by Val; when Asn ($AA_5$) is replaced it is replaced by Asp or Gln; and when Thr ($AA_6$) is replaced it is replaced by Ala, Ser or no amino acid; provided $AA_1$ is not the same as $AA_6$.

In the amino acid sequences of Table 2 according to formula (I), formula (II) or formula (III), $R_1$ and $R_2$ are H and OH, respectively. Compounds of the invention include each of the sequences of Table 2 with their N- and C-terminals modified by the other $R_1$ and $R_2$ groups, respectively, as defined herein for formula (I), formula (II) or formula (III). For example, compounds of the invention include each of the sequences of Table 2 in which the N-terminal amino acid residue terminates with $R_1$ as defined above for formula (I) where $R_1$ is not H, and, alternatively or additionally, where the C-terminal amino acid residue optionally terminates with $R_2$ as defined above for formula (I), formula (II) or formula (III), where $R_2$ is not OH.

Thus, in particular, the invention provides for a compound according to formula (I), (II) or (III), wherein the compound is any of the amino acid sequences SEQ ID NO. 1 to 39 or 40 and its stereoisomers, and/or its cosmetically acceptable salts, wherein optionally, said sequence has its N-terminal amino acid modified by $R_1$ as defined above for formula (I), (II) or (III), where $R_1$ is not H, and, alternatively or additionally, said sequence has its C-terminal amino acid modified by $R_2$ as defined above for formula (I), where $R_2$ is not OH. The amino acid sequence can be chosen from SEQ ID NO. 1 and SEQ ID NO. 3 to SEQ ID NO. 19. The amino acid sequence can be chosen from SEQ ID NO. 2 and SEQ ID NO. 20 to SEQ ID NO. 39, or from SEQ ID NO. 2 and SEQ ID NO. 20 to 40. The amino acid sequence can be SEQ ID NO. 1 or SEQ ID NO. 2.

The compounds of this invention can exist as stereoisomers or mixtures of stereoisomers; for example, the amino acids which comprise them can have the configuration L-, D-, or be racemic independently of each other. Therefore, it is possible to obtain isomeric mixtures as well as racemic mixtures or diastereomeric mixtures, or pure diastereomers or enantiomers, depending on the number of asymmetric carbons and on which isomers or isomeric mixtures are present. The preferred structures of the compounds of the invention are pure isomers, i.e., enantiomers or diastereomers. For example, when it is stated that $AA_2$ can be Arg, it is understood that, unless otherwise specified, $AA_2$ is selected from L-Arg, D-Arg or mixtures of both, racemic or non-racemic. The preparation procedures described in this document enable the person skilled in the art to obtain each of the stereoisomers of the compound of the invention by choosing the amino acid with the right configuration.

In the context of this invention, the term "amino acids" includes the amino acids encoded by the genetic code as well as non-encoded amino acids, whether they are natural or not. Examples of non-encoded amino acids are, without restriction, citrulline, ornithine, sarcosine, desmosine, norvaline, 4-aminobutyric acid, 2-aminobutyric acid, 2-aminoisobutyric acid, 6-aminohexanoyc acid, 1-naphthylalanine, 2-naphthylalanine, 2-aminobenzoic acid, 4-aminobenzoic acid, 4-chlorophenylalanine, 2,3-diaminopropionic acid, 2,4-diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, statin, β-alanine, norleucine, N-methyl amino acids, α-amino acids and β-amino acids, among others, as well as their derivatives. A list of non-natural amino acids can be found in the article "*Unusual amino acids in peptide synthesis*" by D. C. Roberts and F. Vellaccio, in *The Peptides*, Vol. 5 (1983), Chapter VI, Gross E. and Meienhofer J., Eds., Academic Press, New York, USA or in the commercial catalogues of the companies specialized in the field.

In the context of this invention, when W, X, Y and/or Z are present, i.e., at least one of n, m, p or q is not 0, it is understood that the nature of W, X, Y and/or Z does not hinder the activity of the compound of the invention, and, instead, contributes to it or has no effect on it. W, X, Y and Z can each be independently selected from the group consisting of Ala, Gly, Val and Ile. W, X, Y and Z can each be independently selected from the group consisting of Ala, Gly and Val. W, X, Y and Z can each be independently Ala or Gly. W, X, Y and Z can each be Ala.

Each of m, n, p and q can be 0, i.e., the compound of formula (I) is a peptide which comprises 3, 4, 5 or 6 amino acids (e.g., $AA_2$-$AA_3$-$AA_4$, $AA_1$-$AA_2$-$AA_3$-$AA_4$, $AA_2$-$AA_3$-$AA_4$-$AA_5$-$AA_6$ and $AA_1$-$AA_2$-$AA_3$-$AA_4$-$AA_5$-$AA_6$), linked in a chain. Alternatively, the sum of m, n, p and q can be 1, i.e., the compound of formula (I) is a peptide which comprises 4, 5, 6 or 7 amino acids linked in a chain. Alternatively, the sum of m, n, p and q can be 2, i.e., the compound of formula (I) is a peptide which comprises 5, 6, 7 or 8 amino acids linked in a chain.

Each of m, n, p and q can be 0, i.e., the compound of formula (II) is a peptide which comprises 4 amino acids, $AA_1$ to $AA_4$, linked in a chain. Alternatively, the sum of m, n, p and q can be 1, i.e., the compound of formula (I) is a peptide which comprises 5 amino acids linked in a chain. Alternatively, the sum of m, n, p and q can be 2, i.e., the compound of formula (II) is a peptide which comprises 6 amino acids linked in a chain.

Each of m, n, p and q can be 0, i.e., the compound of formula (III) is a peptide which comprises 5 or 6 amino acids, $AA_1$ to $AA_5$, $AA_2$ to $AA_6$ or $AA_1$ to $AA_6$, linked in a chain. Alternatively, the sum of m, n, p and q can be 1, i.e., the compound of formula (III) is a peptide which comprises 6 or 7 amino acids linked in a chain. Alternatively, the sum of m, n, p and q can be 2, i.e., the compound of formula (III) is a peptide which comprises 7 or 8 amino acids linked in a chain.

In particular, the compound of the invention can be selected from the group of compounds listed in Table 3, their stereoisomers, and/or their cosmetically acceptable salts.

TABLE 3

| Compound | Identifier |
|---|---|
| Ac-Asp-Val-Tyr-Lys-NH$_2$ | PEP1 |
| H-Ala-Leu-Lys-Pro-Asn-Thr-NH$_2$ | PEP2 |
| Palm-Asp-Val-Tyr-Lys-NH$_2$ | PEP3 |
| Ac-Asp-Val-Tyr-Lys-OH | PEP4 |
| H-Asp-Val-Tyr-Lys-NH$_2$ | PEP5 |
| Palm-Asp-Val-Tyr-Lys-OH | PEP6 |
| Ac-Glu-Val-Tyr-Lys-NH$_2$ | PEP7 |
| Ac-Asp-Ile-Tyr-Lys-NH$_2$ | PEP8 |
| Ac-Asp-Val-Phe-Lys-NH$_2$ | PEP9 |
| Ac-Asp-Val-Tyr-Arg-NH$_2$ | PEP10 |
| Ac-Asn-Val-Tyr-Lys-NH$_2$ | PEP11 |
| Ac-Asp-Leu-Tyr-Lys-NH$_2$ | PEP12 |
| Palm-Glu-Val-Tyr-Lys-NH$_2$ | PEP13 |
| Ac-Ala-Asp-Val-Tyr-Lys-NH$_2$ | PEP14 |
| Ac-Asp-Val-Tyr-Lys-Ala-NH$_2$ | PEP15 |
| Ac-Ala-Glu-Val-Tyr-Lys-NH$_2$ | PEP16 |
| Ac-Ala-Asp-Val-Tyr-Lys-Ala-NH$_2$ | PEP17 |
| Ac-Ala-Ala-Asp-Val-Tyr-Lys-NH$_2$ | PEP18 |
| Ac-Ala-Glu-Val-Tyr-Lys-Ala-NH$_2$ | PEP19 |
| Ac-Glu-Ile-Tyr-Lys-NH$_2$ | PEP20 |
| Ac-Ala-Glu-Ile-Tyr-Lys-Ala-NH$_2$ | PEP21 |
| Ac-Glu-Ile-Phe-Lys-NH$_2$ | PEP22 |
| Ac-Glu-Ile-Tyr-Arg-NH$_2$ | PEP23 |
| Ac-Glu-Ile-Phe-Arg-NH$_2$ | PEP24 |
| Palm-Ala-Leu-Lys-Pro-Asn-Thr-NH$_2$ | PEP25 |
| Ac-Ala-Leu-Lys-Pro-Asn-Thr-NH$_2$ | PEP26 |
| Ac-Ala-Leu-Lys-Pro-Asn-Thr-OH | PEP27 |
| H-Gly-Leu-Lys-Pro-Asn-Thr-NH$_2$ | PEP28 |
| H-Ala-Ile-Lys-Pro-Asn-Thr-NH$_2$ | PEP29 |
| H-Ala-Leu-Arg-Pro-Asn-Thr-NH$_2$ | PEP30 |
| H-Ala-Leu-Lys-Val-Asn-Thr-NH$_2$ | PEP31 |
| H-Ala-Leu-Lys-Pro-Asp-Thr-NH$_2$ | PEP32 |
| H-Ala-Leu-Lys-Pro-Asn-Ala-NH$_2$ | PEP33 |
| H-Ala-Leu-Lys-Pro-Asn-ser-NH$_2$ | PEP34 |
| H-Ala-Ala-Leu-Lys-Pro-Asn-Thr-NH$_2$ | PEP35 |
| H-Ala-Leu-Lys-Pro-Asn-Thr-Ala-NH$_2$ | PEP36 |
| H-Ala-Ala-Leu-Lys-Pro-Asn-Thr-Ala-NH$_2$ | PEP37 |
| Ac-Ala-Ala-Leu-Lys-Pro-Asn-Thr-NH$_2$ | PEP38 |
| Pal-Ala-Leu-Lys-Pro-Asn-Thr-Ala-NH$_2$ | PEP39 |
| H-Leu-Lys-Pro-Asn-Thr-NH$_2$ | PEP40 |
| H-Ala-Leu-Lys-Pro-Asn-NH$_2$ | PEP41 |
| H-Gly-Ile-Lys-Pro-Asn-Thr-NH$_2$ | PEP42 |
| H-Gly-Val-Lys-Pro-Asn-Thr-NH$_2$ | PEP43 |
| H-Ala-Ile-Arg-Pro-Asn-Thr-NH$_2$ | PEP44 |

TABLE 3-continued

| Compound | Identifier |
|---|---|
| H-Ala-Ile-Lys-Pro-Asp-Thr-NH$_2$ | PEP45 |
| H-Gly-Val-Arg-Pro-Asn-Thr-NH$_2$ | PEP46 |
| H-Ala-Ile-Arg-Pro-Asp-Thr-NH$_2$ | PEP47 |
| H-Gly-Val-Arg-Pro-Asp-Thr-NH$_2$ | PEP48 |
| H-Gly-Leu-Lys-Pro-Asn-Thr-Ala-NH$_2$ | PEP49 |
| H-Ala-Leu-Lys-Pro-Gln-Thr-NH$_2$ | PEP50 |

Compounds of the invention include each of the compounds of Table 3 in which one of amino acids $AA_1$ to $AA_6$ is replaced by a replacement amino acid, wherein the replacement amino acid is selected from the alternative amino acids listed for the amino acid being replaced in formula (I), formula (II) or formula (III) above. The replacement amino acid is different from the amino acid that is being replaced. The replacement amino acid can be no amino acid. Thus the invention provides for a compound of formula (II) corresponding to SEQ ID NO. 1 in which one of amino acids $AA_1$ to $AA_4$ is replaced by an amino acid, wherein: when Asp ($AA_1$) is replaced it is replaced by Gly, Asn or Gln; when Val ($AA_2$) is replaced it is replaced by Ile, Leu or Ala; when Tyr ($AA_3$) is replaced it is replaced by Phe or Trp; and when Lys ($AA_4$) is replaced, it is replaced by Arg or Lys. Further, the invention provides for a compound of formula (III) corresponding to SEQ ID NO. 2 in which one of amino acids $AA_1$ to $AA_6$ is replaced by an amino acid, wherein: when Ala ($AA_1$) is replaced it is replaced by Gly or no amino acid; when Leu ($AA_2$) is replaced it is replaced by Ile or Val; when Lys ($AA_3$) is replaced it is replaced by Arg or His; when Pro ($AA_4$) is replaced, it is replaced by Val; when Asn ($AA_5$) is replaced it is replaced by Asp or Gln; and when Thr ($AA_6$) is replaced it is replaced by Ala, Ser or no amino acid; provided $AA_1$ is not the same as $AA_6$.

The invention provides for a compound according to formula (I), wherein the compound is selected from any of PEP1 to PEP49 or from any of PEP 1 to PEP50, and its stereoisomers, and/or its cosmetically or pharmaceutically acceptable salts. The compound of the invention can be selected from PEP1 and PEP3 to PEP24. The compound of the invention can be selected from PEP2 and PEP25 to PEP49 or from PEP2 and PEP25 to PEP50. Particularly, the compound can be selected from PEP1 and PEP2.

The cosmetically or pharmaceutically acceptable salts of the compounds provided by the present invention are also found within the field of this invention. The term "cosmetically or pharmaceutically acceptable salt" means a salt recognized for its use in animals, for example, in mammals, and more specifically in human beings, and includes salts used to form base addition salts, either they are inorganic, for example and not restricted to, lithium, sodium, potassium, calcium, magnesium, manganese, copper, zinc or aluminium among others, or they are organic, for example and not restricted to, ethylamine, diethylamine, ethylenediamine, ethanolamine, diethanolamine, arginine, lysine, histidine or piperazine among others, or acid addition salts, either they are organic, for example and not restricted to, acetate, citrate, lactate, malonate, maleate, tartrate, fumarate, benzoate, aspartate, glutamate, succinate, oleate, trifluoroacetate, oxalate, pamoate or gluconate among others, or inorganic, for example and not restricted to, chloride, sulfate, borate or carbonate, among others. The nature of the salt is not critical, provided that it is cosmetically or pharmaceutically acceptable. The cosmetically or pharmaceutically acceptable salts of the compounds of the invention can be obtained by the conventional methods, well known in the prior art [Berge S. M. et al., *"Pharmaceutical Salts"*, (1977), *J. Pharm. Sci.*, 66, 1-19].

The invention also provides for a combination of the compound of the invention, its stereoisomers, and/or its cosmetically acceptable salts, in any of the embodiments described above, with: a Botulinum toxin; Ac-Glu-Glu-Met-Gln-Arg-Arg-$NH_2$ (Ac-[SEQ ID NO. 41]-$NH_2$; or H-Tyr-D-Ala-Gly-Phe-Leu-OH; or combinations thereof.

Preparation Procedures of the Compounds of the Invention

Synthesis of the compounds of the invention, their stereoisomers, mixtures thereof and/or their cosmetically or pharmaceutically acceptable salts can be carried out according to conventional methods, known in the prior art, such as solid phase peptide synthesis methods [Stewart J. M. and Young J. D., *"Solid Phase Peptide Synthesis, 2nd edition"*, (1984), Pierce Chemical Company, Rockford, Illinois; Bodanzsky M. and Bodanzsky A., *"The practice of Peptide Synthesis"*, (1994), Springer Verlag, Berlin; Lloyd-Williams P. et al., *"Chemical Approaches to the Synthesis of Peptides and Proteins"*, (1997), CRC, Boca Raton, FL, USA], synthesis in solution, enzymatic synthesis [Kullmann W. *"Proteases as catalysts for enzymic syntheses of opioid peptides"*, (1980), *J. Biol. Chem.*, 255(17), 8234-8238] or any combination thereof. The compounds can also be obtained by fermentation of a bacterial strain, modified or unmodified by genetic engineering with the objective of producing the desired sequences, or by controlled hydrolysis of proteins with animal or plant origins, preferably plant, which results in free peptide fragments that contain the desired sequence.

For example, a method of obtaining the compounds of formula (I), their stereoisomers and mixtures thereof comprises the stages of:

coupling of an amino acid, with the N-terminal end protected and the C-terminal end free, with an amino acid with the N-terminal end free and the C-terminal end protected or bound to a solid support;

elimination of the protective group of the N-terminal end;

repetition of the coupling sequence and elimination of the protective group of the N-terminal end until the desired peptide sequence is obtained;

elimination of the protective group of the C-terminal end or cleavage of the solid support.

Preferably, the C-terminal end is bound to a solid support and the process is carried out in solid phase and, therefore, comprises the coupling of an amino acid with the N-terminal end protected and the C-terminal end free, with an amino acid with the N-terminal end free and the C-terminal end bound to a polymeric support; elimination of the protective group of the N-terminal end; and repetition of this sequence as many times as is necessary to thus obtain the compound of desired length, finally followed by the cleavage of the synthesized compound from the original polymeric support.

The functional groups of the side chains of the amino acids are maintained conveniently protected with temporary or permanent protective groups throughout synthesis, and can be unprotected simultaneously or orthogonally to the process of cleavage of the peptide from the polymeric support.

Alternatively, solid phase synthesis can be carried out using a convergent strategy coupling a peptide with the polymeric support or with a peptide or an amino acid previously bound to the polymeric support. Convergent synthesis strategies are widely known by persons skilled in the art and are described in Lloyd-Williams P. et al., *"Convergent Solid-Phase Peptide Synthesis"*, (1993), *Tetrahedron*, 49(48), 11065-11133.

The process can comprise the additional stages of deprotection of the N-terminal and C-terminal ends and/or cleavage of the peptide from the polymeric support in an indiscriminate order, using standard procedures and conditions known in the prior art, after which the functional groups of these ends can be modified. The optional modification of the N-terminal and C-terminal ends can be carried out with the peptide of formula (I) anchored to the polymeric support or once the peptide has been separated from the polymeric support.

Optionally, $R_1$ can be introduced by the reaction of the N-terminal end of the compound of the invention with a $R_1$—X compound through a nucleophilic substitution reaction, in the presence of an adequate base and solvent, wherein the fragments that have the functional groups not involved in the N—C bond formation are suitably protected with temporary or permanent protective groups. $R_1$ is as defined above and X is a leaving group, for example and not restricted to, the tosyl group, the mesyl group and halogen groups among others.

Optionally and/or additionally, the $R_2$ radicals can be introduced by the reaction of a compound $HR_2$ with a complementary fragment which corresponds to the peptide of formula (I) in which $R_2$ is —OH in the presence of an adequate solvent and a base such as N,N-diisopropylethylamine (DIEA) or trimethylamine, or an additive such as 1-hydroxybenzotriazole (HOBt) or 1-hydroxyazabenzotriazole (HOAt), and a dehydrating agent such as a carbodiimide, a uronium salt, a phosphonium salt or amidinium salt, among others, or by prior formation of an acyl halide with, for example, thionyl chloride, and thereby obtaining a peptide according to the invention of formula (I), wherein the fragments that have the functional groups not involved in the N—C bond formation are suitably protected with temporary or permanent protective groups. Alternatively other $R_2$ radicals may be introduced by simultaneous incorporation to the peptide cleavage process from the polymeric carrier. $R_2$ is —$OR_3$, —$NR_3R_4$ or —$SR_3$, where $R_3$ and $R_4$ are as defined above.

A person skilled in the art would easily understand that the deprotection/cleavage steps of the C-terminal and N-terminal ends and their subsequent derivatization can be performed in a different order, according to the processes known in the prior art.

The term "protective group" relates to a group which blocks an organic functional group and which can be removed in controlled conditions. The protective groups, their relative reactivities and the conditions in which they remain inert are known to the person skilled in the art.

Examples of representative protective groups for the amino group are amides, such as amide acetate, amide benzoate, amide pivalate; carbamates such as benzyloxycarbonyl (Cbz or Z), 2-chlorobenzyl (ClZ), para-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), 9-fluorenylmethyloxycarbonyl (Fmoc) or allyloxycarbonyl (Alloc), trityl (Trt), methoxytrityl (Mtt), 2,4-dinitrophenyl (Dnp), N-[1-(4,4-dimethyl-2,6-dioxocyclohex-1-ylidene)ethyl (Dde), 1-(4,4-dimethyl-2,6-dioxo-cyclohexylidene)-3-methylbutyl (ivDde), 1-(1-adamantyl)-1-methylethoxycarbonyl (Adpoc), among others, preferably Boc or Fmoc.

Examples of representative protective groups for the carboxyl group are esters, such as the tert-butyl ester (tBu), allyl ester (All), triphenylmethyl ester (Trt tester), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-(N-[1-(4,4-dimethyl-2,6-dioxocyclohexylidene)-3-methylbutyl]amino) benzyl ester (Dmab), among others; preferred protective groups of the invention are the All, tBu, cHex, Bzl and Trt esters.

The side chains of trifunctional amino acids can be protected during the synthetic process with temporary or permanent protective groups orthogonal to the protective groups of the N-terminal and C-terminal ends.

The hydroxyl group of the tyrosine side chain can be protected with the 2-bromobenzyloxycarbonyl group (2-BrZ), tBu, All, Bzl or 2,6-dichlorobenzyl (2,6-diClZ) among others. In a preferred embodiment, the protective group strategy used is the strategy wherein the amino groups are protected by Boc, the carboxyl groups are protected by Bzl, cHx or All esters and the tyrosine side chain is protected with 2-BrZ or Bzl. In another preferred embodiment, the protective group strategy used is the strategy wherein the amino groups are protected by Fmoc, the carboxyl groups are protected by tBu, All or Trt esters, the tyrosine side chain is protected by tBu.

The amino group of the tryptophan side chain can be protected, for example, by the formyl group (For) or Boc. In one embodiment, when the amino group is protected by Fmoc, and the tryptophan side chain can be: unprotected, i.e., the amino acid is incorporated as Fmoc-Trp-OH; protected by Boc, i.e., the amino acid is incorporated as Fmoc-Trp(Boc)-OH; or protected by For, i.e., the amino acid is incorporated as Fmoc-Trp(For)-OH. In one embodiment, the amino group is protected by Boc, and the tryptophan side chain can be protected by For, i.e., the amino acid is incorporated as Boc-Trp(For)-OH.

Examples of these and other protective groups, their introduction and removal, can be found in the literature [Atherton B. and Sheppard R. C., "*Solid Phase Peptide Synthesis: A practical approach*", (1989), IRL Oxford University Press]. The term "protective groups" also includes the polymeric supports used in solid phase synthesis.

When synthesis takes place totally or partially in solid phase, the possible solid supports used in the process of the invention involve polystyrene support, polyethylene glycol grafted to polystyrene and similar, for example and not restricted to, p-methylbenzhydrylamine resins (MBHA) [Matsueda G. R. et al., "A p-methylbenzhydrylamine resin for improved solid-phase synthesis of peptide amides", (1981), *Peptides*, 2, 45-50], 2-chlorotrityl resins [Barlos K. et al., "Darstellung geschützter Peptid-Fragmente unter Einsatz substituierter Triphenylmethyl-Harze", (1989), *Tetrahedron Lett.*, 30, 3943-3946; Barlos K. et al., "Veresterung von partiell geschützten Peptid-Fragmenten mit Harzen. Einsatz von 2-Chlorotritylchlorid zur Synthese von Leu1-Gastrin I", (1989), *Tetrahedron Lett.*, 30, 3947-3951], TentaGel® resins (Rapp Polymere GmbH), ChemMatrix® resins (Matrix Innovation, Inc) and similar, which may or may not include a labile linker, such as 5-(4-aminomethyl-3,5-dimethoxyphenoxy) valeric acid (PAL) [Albericio F. et al., "Preparation and application of the 5-(4-(9-fluorenylmethyloxycarbonyl) aminomethyl-3,5-dimethoxy-phenoxy)valeric acid (PAL) handle for the solid-phase synthesis of C-terminal peptide amides under mild conditions", (1990), *J. Org. Chem.*, 55, 3730-3743], 2-[4-aminomethyl-(2,4-dimethoxyphenyl)] phenoxyacetic acid (AM) [Rink H., "Solid-phase synthesis of protected peptide fragments using a trialkoxy-diphenyl-methylester resin", (1987), *Tetrahedron Lett.*, 28, 3787-3790], [Wang S. S., "p-Alkoxybenzyl Alcohol Resin and p-Alkoxybenzyloxycarbonylhydrazide Resin for Solid Phase Synthesis of Protected Peptide Fragments", (1973), *J. Am. Chem. Soc.*, 95, 1328-1333] and similar, which enable simultaneous deprotection and cleavage of the compound from the polymeric support.

Applications

The present invention is based on the finding that compounds of formula (I) (the compounds of the invention) are useful in the treatment of the skin, hair, nails and/or mucous membranes. In particular, it has been found that compounds of the invention can inhibit upregulated the expression of muscle bind-like1 (MBNL-1) protein in the skin/skeletal muscle and thus are useful in the prevention or treatment of the symptoms of skin aging including skin wrinkles, a sagging appearance of the skin and a loss of firmness and for treating or preventing facial asymetry. It has been found that compounds of the invention can inhibit noradrenaline release and increase collagen synthesis in skin. It has been found that compounds of the invention can increase the lipid content of adipose cells and thus can cause an increase in the volume of adipose tissue. These effects further indicate the usefulness of the compounds of the invention in the prevention or treatment of the symptoms of skin aging. Thus, the compounds of formula (I) are useful in the cosmetic, non-therapeutic treatment of the skin, hair, nails and/or mucous membranes.

MBNL1 is a RNA-binding protein which is implicated in the differentiation and maintenance of the splicing pattern required for a healthy muscle function. Several observations have linked MBNL1 loss of function as a cause of muscle mass loss during the natural muscle aging process in healthy people [Malatesta, M. et al. "Muscle blind-like1 undergoes ectopic relocation in the nuclei of skeletal muscles in myotonic dystrophy and sarcopenia", (2013), European Journal of Histochemistry, vol. 57(e15), pp. 86-92; Malatesta, M. et al. "RNA transcription and maturation in skeletal muscle cells are similarly impaired in myotonic dystrophy and sarcopenia: the ultrastructural evidence", (2014), Frontiers in Aging Neuroscience, vol. 6(196), pp. 1-6]. It has also been demonstrated that an increase of MBNL1 protein in fibroblast cells activate their trans-differentiation process to myofibroblast, a cell-type able to release a higher amount of extracellular matrix proteins, like collagen, elastin and fibronectin. In fact, electrical stimulation is demonstrated to induce myofibroblast appearance and function [Davis, J. et al. "MBNL1-mediated regulation of differentiation RNAs promotes myofibroblast transformation and the fibrotic response", (2015), Nature communications, vol. 6(10084), pp. 1-14; Jennings, J. A., et al. "Regulation of gene expression in response to continuous low intensity direct current electrical fields", (2007), Doctoral Thesis, pp-1-208].

It is believed that an increase of MBNL1 protein in the skin/facial muscles contributes to the slowing down of and/or avoidance of muscle mass loss due to the activation of atrophic processes due to muscle aging. Compounds of the invention are particularly effective at upregulating the expression of muscle blind-like1 (MBNL-1), and are thus useful for preventing or alleviating the effects on cosmetic properties of the skin associated with loss of muscle mass due to muscle aging. Thus compounds of the invention are especially useful in maintaining or improving skin firmness, preventing sagging appearance of the skin, and/or reducing facial asymmetry.

Collagen is the most abundant protein in skin connective tissue; it forms a mesh-like structure that helps to support new cells as they grow while providing needed flexibility. Type I collagen (Collagen I) is the principal collagen of skin and is responsible for the strength and resiliency of this tissue. One of well-recognized characteristics of aging is sagging of the skin. This is due to a number of factors including loss of elasticity and firmness of the skin, the effect of gravity, the loss of skeletal support of the face, as well as loss of subcutaneous adipose tissue support in the face. An increase in collagen synthesis associated with the increase in MBLN1 protein is considered to be beneficial to the reduction of the above-mentioned symptoms of skin aging.

The inhibition of noradrenaline release is an indication of inhibition of neuronal exocytosis, similar to that of the Botulinum toxins. In the neuromuscular junctions, the release of neurotransmitters from peripheral neurons to skeletal muscle allows muscle contraction. Facial muscles are also subjected to these contractions. These contractions are more frequent around the eyes and mouth and in the forehead. With age, continuous release of neurotransmitters into neuromuscular junctions and decrease of elasticity, contributes to the increase of facial wrinkles and permanent expression lines. Therefore, inhibiting noradrenaline release is considered to be beneficial to the reduction these symptoms of aging.

Adipose tissue or body fat is a connective tissue comprising cells called adipocytes which accumulate lipids. Advantageously, compounds of the invention have been found to be effective increasing the lipid content in adipose cell and thus are useful in treatments to increase of the volume of adipose tissue, prevent and/or alleviate of effects of adipose tissue loss.

In one aspect, the invention provides the use of the compound of the invention, a stereoisomer and/or cosmetically acceptable salt thereof, or a cosmetic composition comprising the compound of the invention, a stereoisomer and/or a cosmetically acceptable salt thereof, in the cosmetic, non-therapeutic treatment and/or care of the skin, hair, nails and/or mucous membranes. In particular, the cosmetic, non-therapeutic treatment and/or care is that of the skin. In the context of this invention, skin includes the skin of the whole body including the skin of the face (including skin around the eyes), neckline, neck, décolletage, arms, hands, legs, feet, thighs, hips, buttocks, stomach and torso.

The compounds of the invention are useful in the cosmetic, non-therapeutic treatment and/or care of the skin, including: the treatment and/or prevention of the aging of the skin, the treatment and/or prevention of skin wrinkles; maintaining and improving skin firmness; the stimulation of collagen synthesis and/or prevention of collagen loss; the treatment and/or prevention of a sagging appearance of the skin; the reduction and/or prevention of facial asymmetry; the increase of the volume of adipose tissue; and/or the prevention and/or alleviation of effects of adipose tissue loss.

The compounds of the invention are useful in the cosmetic, non-therapeutic treatment and/or care of the skin, including: the treatment and/or prevention of the aging of the skin, the treatment and/or prevention of skin wrinkles; maintaining and improving skin firmness; the stimulation of collagen synthesis and/or prevention of collagen loss; the treatment and/or prevention of a sagging appearance of the skin; the reduction and/or prevention of facial asymmetry; the increase of the volume of adipose tissue; the prevention and/or alleviation of effects of adipose tissue loss; and/or the reduction of skin roughness and/or the improvement of skin smoothness.

The cosmetic, non-therapeutic treatment and/or care of the skin can be: the treatment and/or prevention of skin wrinkles; maintaining and improving skin firmness; the stimulation of collagen synthesis and/or prevention of collagen loss.

The cosmetic, non-therapeutic treatment and/or care can involve the stimulation of the synthesis of collagen and/or the upregulation of MBNL-1 and/or the inhibition of noradrenaline. Thus, the cosmetic, non-therapeutic treatment and/or care of the skin, hair, nails and/or mucous membranes can be associated with increasing collagen synthesis and/or upregulating expression of muscle blind-like1 (MBNL-1) and/or the presence of noradrenaline.

In one embodiment, there is provided the use of the compound of the invention, a stereoisomer and/or cosmetically acceptable salt thereof, or a cosmetic composition comprising the compound of the invention, a stereoisomer and/or cosmetically acceptable salt thereof, for the treatment and/or prevention of the aging of the skin. The treatment and/or prevention is skin aging includes the alleviation and/or the prevention of symptoms of skin aging. The symptoms of skin aging include the appearance of wrinkles and the loss of skin biomechanical properties such as firmness. The loss of firmness can be due to the reduction in collagen production in the skin or the loss of muscle tone (muscle mass) with age. Particularly, the loss of muscle tone refers to cutaneous muscles, more particularly to cutaneous facial muscles.

In one embodiment, there is provided the use of the compound of the invention, a stereoisomer and/or cosmetically acceptable salt thereof, or a cosmetic composition comprising the compound of the invention, a stereoisomer and/or cosmetically acceptable salt thereof, for the treatment and/or prevention of skin wrinkles. Skin wrinkles include expression wrinkles, also commonly referred as expression lines.

In one embodiment, there is provided the use of the compound of the invention, a stereoisomer and/or cosmetically acceptable salt thereof or a cosmetic composition comprising the compound of the invention, a stereoisomer and/or cosmetically acceptable salt thereof, for maintaining and/or improving skin firmness.

In one embodiment, there is provided the use of the compound of the invention, a stereoisomer and/or cosmetically acceptable salt thereof, or a cosmetic composition comprising the compound of the invention, a stereoisomer and/or cosmetically acceptable salt thereof, for the stimulation of collagen synthesis and/or prevention of collagen loss.

In one embodiment, there is provided the use of the compound of the invention, a stereoisomer and/or cosmetically acceptable salt thereof, or a cosmetic composition comprising the compound of the invention, a stereoisomer and/or cosmetically acceptable salt thereof, for the treatment and/or prevention of a sagging appearance of the skin. Sagging appearance can be caused by loss of muscle tone (muscle mass), particularly cutaneous muscle tone, more particularly facial muscles.

In one embodiment, there is provided the use of the compound of the invention, a stereoisomer and/or cosmetically acceptable salt thereof, or a cosmetic composition comprising the compound of the invention, a stereoisomer and/or cosmetically acceptable salt thereof, for the reduction and/or prevention of facial assymmetry.

In one embodiment, there is provided the use of the compound of the invention, a stereoisomer and/or cosmetically acceptable salt thereof, or a cosmetic composition comprising the compound of the invention, a stereoisomer and/or cosmetically acceptable salt thereof, for increasing the volume of adipose tissue; and/or prevention and/or alleviation of adipose tissue loss. Particularly, the adipose tissue is subcutaneous adipose tissue, more particularly of the subcutaneous adipose tissue of the face, hands and lower part of the neck. The compound of the invention, a stereoisomer and/or cosmetically acceptable salt thereof, or a cosmetic composition comprising the compound of the invention, a stereoisomer and/or cosmetically acceptable salt thereof, can reduce the adquisition of a senescence-associated secretory phenotype (SASP).

In one embodiment, there is provided the use of the compound of the invention, a stereoisomer and/or cosmetically acceptable salt thereof, or a cosmetic composition comprising the compound of the invention, a stereoisomer and/or cosmetically acceptable salt thereof, for the reduction of skin roughness and/or improvement of skin smoothness.

The invention extends to the use of a combination of the compound of the invention with micro-current electrical neuromuscular stimulation (MENS) treatment in the treatment and/or care of the skin, hair, nails and/or mucous membranes as described above in relation to the applications (uses) of the compounds of the invention. The MENS treatment is a cosmetic, non-therapeutic treatment of the skin, hair, nails and/or mucous membrane. For example, MENS treatment typically employs direct current (as opposed to alternating) in the range of less of 1 mA, e.g., 300-500 µA, which current may be, optionally, pulsed at a frequency of 0.1 to 680 Hz.

The invention also extends to the use of a combination of the compound of the invention with a Botulinum toxin and/or Ac-Glu-Glu-Met-Gln-Arg-Arg-NH$_2$, in the treatment and/or care of the skin, hair, nails and/or mucous membranes as described above in relation to the applications (uses) of the compounds of the invention. Ac-Glu-Glu-Met-Gln-Arg-Arg-NH$_2$ is commercialized as Argireline® peptide by Lipotec SAU (Lubrizol) and is known to imitate the cosmetic effects of Botulinum toxins on the skin in that it inhibits neuronal exocytosis.

In another aspect, the invention provides a method of treatment and/or care of the skin, hair, nails and/or mucous membranes of a subject comprising administering a compound of the invention, a stereoisomer and/or cosmetically or pharmaceutically acceptable salt thereof or a composition comprising the compound of the invention, a stereoisomer and/or a cosmetically or pharmaceutically acceptable salt thereof, to the subject. In particular, the invention provides a cosmetic, non-therapeutic method of treatment and/or care of the skin, hair, nails and/or mucous membranes in a subject comprising administering a cosmetically effective amount of a compound of the invention, a stereoisomer and/or cosmetically acceptable salt thereof or a cosmetic composition comprising a cosmetically effective amount of the compound of the invention, a stereoisomer and/or a cosmetically acceptable salt thereof, to the subject. The method can be for the treatment and/or care of the skin, hair, nails and/or mucous membranes as described above in relation to the applications (uses) of the compounds and compositions of the invention. In particular, the cosmetic, non-therapeutic method of treatment and/or care is that of the skin. The administration can be topical or, for example, transdermal. In this aspect of the invention, the compound of the invention may be present in a cosmetic composition such as the cosmetic composition as described herein. In one embodiment, the method involves administering the compound or administering the composition using microneedles.

The invention extends to a method of treatment and/or care of the skin, hair, nails and/or mucous membranes of a subject comprising administering a combination of the compound of the invention, a stereoisomer and/or cosmetically or pharmaceutically acceptable salt thereof and administering cosmetic micro-current electrical neuromuscular stimulation (MENS) treatment to the subject. The method can be for the treatment and/or care of the skin, hair, nails and/or mucous membranes as described above in relation to the applications (uses) of the compounds of the invention. The MENS treatment is a cosmetic, non-therapeutic treatment of the skin, hair, nails and/or mucous membrane and, for example, typically employs direct current (as opposed to alternating) in the range of 300-500 µA. The current may be pulsed at a frequency of 0.1 to 680 Hz. Preferably, this method of treatment is a skin antiaging treatment. The compound of the invention can be administered simultaneously (at the same time) with the MENS treatment or sequentially with the MENS treatment. The compound of the invention can be administered before or after the MENS treatment. In a non-limiting example, the method of treatment can involve a cosmetic treatment with MENS followed by administration of the compounds at least once a day for a period of time.

The invention also extends to a method of treatment and/or care of the skin, hair, nails and/or mucous membranes of a subject comprising administering a combination of the compound of the invention, a stereoisomer and/or cosmetically or pharmaceutically acceptable salt thereof with a Botulinum toxin and/or Ac-Glu-Glu-Met-Gln-Arg-Arg-NH$_2$, to the subject. The method can be for the treatment and/or care of the skin, hair, nails and/or mucous membranes as described above in relation to the applications (uses) of the compounds of the invention. For example, the method of treatment can comprise administering a Botulinum toxin and a compound of the invention, a stereoisomer and/or cosmetically or pharmaceutically acceptable salt thereof to the subject. For example, the method of treatment can comprise administering: Ac-Glu-Glu-Met-Gln-Arg-Arg-NH$_2$ and a compound of the invention, a stereoisomer and/or cosmetically or pharmaceutically acceptable salt thereof, to the subject. Preferably, this method of treatment is a skin antiaging treatment.

The Botulinum toxin and/or Ac-Glu-Glu-Met-Gln-Arg-Arg-NH$_2$, and the compound of the invention can be administered simultaneously (at the same time) or administered one after the other. When the Botulinum toxin and/or Ac-Glu-Glu-Met-Gln-Arg-Arg-NH$_2$, and the compound of composition of the invention are administered at the same time, they can be administered as a separate dosage forms or as a part of a single composition. When the products are administered in separate dosage forms, the dosage forms can be in the same or different containers.

The above methods of treatment include the cosmetic, non-therapeutic treatment and/or care of the skin, including: the treatment and/or prevention of the aging of the skin, the treatment and/or prevention of skin wrinkles; maintaining and improving skin firmness; the stimulation of collagen synthesis and/or prevention of collagen loss; the treatment and/or prevention of a sagging appearance of the skin; the reduction and/or prevention of facial assymmetry; increasing the volume of adipose tissue; and/or prevention and/or alleviation of adipose tissue loss. In one embodiment, the cosmetic, non-therapeutic method of treatment and/or care of the skin is a skin antiaging treatment.

The above methods of treatment include the cosmetic, non-therapeutic treatment and/or care of the skin, including: the treatment and/or prevention of the aging of the skin, the treatment and/or prevention of skin wrinkles; maintaining and improving skin firmness; the stimulation of collagen synthesis and/or prevention of collagen loss; the treatment and/or prevention of a sagging appearance of the skin; the reduction and/or prevention of facial assymmetry; increasing the volume of adipose tissue; prevention and/or alleviation of adipose tissue loss; and/or the reduction of skin roughness and/or improvement of skin smoothness. In one embodiment, the cosmetic, non-therapeutic method of treatment and/or care of the skin is a skin antiaging treatment.

In another aspect, the invention provides a compound of formula (I), a stereoisomer and/or a pharmaceutically acceptable salt thereof, or a pharmaceutical composition comprising same, for use as a medicament. In particular, the invention provides a compound of formula (I), a stereoisomer and/or a pharmaceutically acceptable salt thereof, or a pharmaceutical composition comprising same, for use in the treatment or prevention of a disease or disorder. In another aspect, the invention provides for the use of the compound of formula (I), a stereoisomer and/or a pharmaceutically acceptable salt thereof for the manufacture of a medicament for the treatment or prevention of a disease or disorder. In another aspect, the invention provides a method of treating or preventing a disease or disorder in a subject comprising administering a therapeutically effective amount of a compound of formula (I) or a pharmaceutical composition comprising same, to the subject.

For the above-described methods of the invention, topical or transdermal application can be carried out by iontophoresis, sonophoresis, electroporation, mechanical pressure, osmotic pressure gradient, occlusive cure, microinjections, by needle-free injections by means of pressure, by microelectric patches, face masks or any combination thereof.

For the above-described methods of the invention, the frequency of application or administration can vary greatly, depending on the needs of each subject, with a recommendation of an application from once a month to ten times a day, preferably from once a week to four times a day, more preferably from three times a week to twice a day, even more preferably once a day. For example, the frequency of the administration according to the method of treatment and/or care of the skin, hair, nails and/or mucous membranes of a subject comprising administering a combination of the compound of the invention, a stereoisomer and/or cosmetically or pharmaceutically acceptable salt thereof with a Botulinum toxin and/or Ac-Glu-Met-Gln-Arg-Arg-NH$_2$ to the subject, can vary widely, depending on the need of each subject. In one embodiment, method of the invention comprises the administration of Botulinum toxin, followed by the administration of the compound or compositions of the invention. In a particular embodiment, after the administration of the Botulinum toxin, the compound or compositions of the invention are administered at least once a day for at least one week. More particularly, the compound or compositions of the invention are administered at least once a day until the next administration of Botulinum toxin.

Compositions of the Invention

The compounds of the invention can be administered for their application by any means that causes contact between the compounds and the site of action in a subject's body, preferably that of a mammal, preferably a human, and in the form of a composition which contains them.

In another aspect, the invention provides a composition comprising a compound according to formula (I), a stereoisomer and/or a cosmetically or pharmaceutically acceptable salt thereof.

In particular, the invention provides a cosmetic composition comprising a compound according to formula (I), a stereoisomer and/or a cosmetically acceptable salt thereof, together with at least one cosmetically acceptable excipient or adjuvant. These compositions can be prepared by conventional means known to persons skilled in the art ["*Harry's Cosmeticology*", Seventh edition, (1982), Wilkinson J. B., Moore R. J., ed. Longman House, Essex, GB].

The compounds of this invention have variable solubility in water, according to the nature of their amino acid sequence or any possible modifications in the N-terminal and/or C-terminal ends. Therefore, the compounds of this invention can be incorporated into the compositions by aqueous solution, and those which are not soluble in water can be solubilized in cosmetically or pharmaceutically acceptable conventional solvents such as and not restricted to, ethanol, propanol, isopropanol, propylene glycol, glycerin, butylene glycol or polyethylene glycol or any combination thereof.

The cosmetically effective amount of the compounds of the invention which should be administered, as well as their dosage, will depend on numerous factors, including age, state of the patient, the nature or severity of the condition, disorder or disease to be treated and/or cared for, the route and frequency of administration and of the particular nature of the compounds to be used.

The terms "cosmetically effective amount" and "pharmaceutically effective amount" are understood to mean a non-toxic but sufficient amount of the compound or compounds of the invention to provide the desired effect. The terms "pharmaceutically effective" and "therapeutically effective" are used interchangeably herein. The compounds of the invention are used in the cosmetic or pharmaceutical compositions of this invention at cosmetically or pharmaceutically effective concentrations to achieve the desired effect; for example, in amounts with respect to the total weight of the composition of: from 0.00000001% (in weight) to 20% (in weight); from 0.000001% (in weight) to 15% (in weight), from 0.00001% (in weight) to 10% (in weight); or from 0.0001% (in weight) to 5% (in weight).

The compounds of formula (I), their stereoisomers, mixtures thereof and/or their cosmetic or pharmaceutically acceptable salts, can also be incorporated into cosmetic or pharmaceutical delivery systems and/or sustained release systems.

The term "delivery system" relates to a diluent, adjuvant, excipient or carrier with which the compound of the invention is administered. These cosmetic or pharmaceutical carriers can be liquids, such as water, oils or surfactants, including those of petroleum, animal, plant or synthetic origin, for example and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants or excipients which can be used in the different delivery systems in which the compound of the invention can be administered.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems include, without restriction, liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, liposheres, millicapsules, microcapsules and nanocapsules, as well as in microemulsions and nanoemulsions, which can be added to achieve a greater penetration of the active principle and/or improve its pharmacokinetic and pharmacodynamic properties. Preferred delivery or sustained release systems are liposomes, surfactant-phospholipid mixed micelles, microemulsions, more preferably water-in-oil microemulsions with an internal structure of reverse micelle and nanocapsules containing microemulsions.

In one embodiment, the invention provides a cosmetic or pharmaceutical composition comprising a compound of formula (I) and a cosmetically or pharmaceutically acceptable carrier selected from the group consisting of creams, emulsions, gels, liposomes, nanoparticles and ointments.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal or subcutaneous implantation or injection, or direct implantation or injection into a specific body part, and preferably should release a relatively constant quantity of the compounds of the invention. The amount of compound contained in the sustained release system will depend, for example, on where the composition is to be administered, the kinetics and duration of the release of the compound of the invention, as well as the nature of the condition, disorder and/or disease to be treated and/or cared for.

The compounds of this invention can also be adsorbed on solid organic polymers or solid mineral supports such as and not restricted to, talc, bentonite, silica, starch or maltodextrin among others.

The compositions which contain the compounds of formula (I), their stereoisomers, mixtures thereof and/or their cosmetically or pharmaceutically acceptable salts can also be incorporated into fabrics, non-woven fabrics and medical devices which are in direct contact with the skin, thus releasing the compounds of the invention whether by biodegradation of the binding system to the fabric, non-woven fabric or medical device, or by friction between them and the body, due to bodily moisture, the skin's pH or body temperature. Furthermore, the compounds of the invention can be incorporated into the fabrics and non-woven fabrics used to make garments that are in direct contact with the body.

Examples of fabrics, non-woven fabrics, garments, medical devices and means for immobilizing the compounds to them, among which are the delivery systems and/or the sustained release systems described above, can be found in literature and are known in the prior art [Schaab C. K. (1986) *HAPPI* May 1986; Nelson G., "*Application of microencapsulation in textiles*", (2002), *Int. J. Pharm.*, 242(1-2), 55-62; "*Biofunctional Textiles and the Skin*" (2006) *Curr. Probl. Dermatol.* v. 33, Hipler U. C. and Elsner P., eds. S. Karger A G, Basel, Switzerland; Malcolm R. K. et al., "*Controlled release of a model antibacterial drug from a novel self-lubricating silicone biomaterial*", (2004), *J. Cont. Release*, 97(2), 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or pharmaceutical compositions which contain the compounds of the invention, their stereoisomers, mixtures thereof and/or their cosmetically or pharmaceutically acceptable salts, can be used in different types of compositions for topical or transdermal application which optionally include cosmetically or pharmaceutically acceptable excipients necessary for formulating the desired administration form.

The compositions for topical or transdermal application can be produced in any solid, liquid or semisolid formulation, such as and not restricted to, creams, multiple emulsions such as and not restricted to, oil and/or silicone in water emulsions, water-in-oil and/or silicone emulsions, water/oil/water or water/silicone/water type emulsions and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated using techniques known by the person skilled in the art into different types of solid accessories for example and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders among others.

The cosmetic or pharmaceutical compositions of the invention may include agents which increase the percutaneous absorption of the compounds of the invention, for example and not restricted to, dimethylsulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the peptide of the invention. The application area will be determined by the nature of the condition, disorder and/or disease to be treated and/or cared for.

Furthermore, the compositions containing the compounds of formula (I), their stereoisomers, mixtures thereof and/or their cosmetically or pharmaceutically acceptable salts can be used in different types of formulations for oral administration, preferably in the form of oral cosmetics or drugs, such as and not restricted to, capsules, including gelatin capsules, soft capsules, hard capsules, tablets, including sugar coated tablets, tablets, pills, powders, granules, chewing gum, solutions, suspensions, emulsions, syrups, elixirs, polysaccharide films, jellies or gelatins, and any other form known by the person skilled in the art. In a particular embodiment, the compounds of the invention can be incorporated into any form of functional food or fortified food, such as and not restricted to, dietary bars or compact or non-compact powders. These powders can be dissolved in water, soda, dairy products, soy derivatives or can be incorporated into dietary bars. The compounds of this invention can be formulated with common excipients and adjuvants for oral compositions or food supplements, for example and not restricted to, fat components, aqueous components, humectants, preservatives, texturizing agents, flavors, aromas, antioxidants and colorants common in the food industry.

Cosmetic or pharmaceutical compositions containing the compounds of formula (I), their stereoisomers, mixtures thereof and/or their cosmetically or pharmaceutically acceptable salts can also be administered, as well as by topical or transdermal route, by any other appropriate route, such as oral or parenteral route, for which they will include the pharmaceutically acceptable excipients necessary for the formulation of the desired administration form. In the context of this invention, the term "parenteral" includes nasal, auricular, ophthalmic, rectal, urethral, vaginal, subcutaneous, intradermal route, intravascular injections, such as intravenous, intramuscular, intraocular, intravitreous, intracorneal, intraspinal, intramedullary, intracranial, intracervical, intracerebral, intrameningeal, intraarticular, intrahepatic, intrathoracic, intratracheal, intrathecal and intraperitoneal, and any another similar injection or infusion technique. A person skilled in the art knows the different means by which the cosmetic or pharmaceutical compositions which contain the compounds of the invention can be administered.

Among the cosmetically or pharmaceutically acceptable adjuvants contained in the cosmetic or pharmaceutical compositions described in this invention are additional ingredients commonly used in cosmetic or pharmaceutical compositions, for example and not restricted to anti-wrinkle agents, botox-like agents and/or anti-aging agents; (ii) firming agents, skin elasticity agents and/or restructuring agents; moisturizing agents; (iv) anti-photoaging agents, and/or blue-light protector agents; DNA protecting agents, DNA repair agents, and/or stem cell protecting agents; free radical scavengers and/or anti-glycation agents, detoxifying agents, antioxidant and/or anti-pollution agents; anti-perspirant agents; melanin synthesis stimulating or inhibiting agents; whitening or depigmenting agents; propigmenting agents; self-tanning agents; lipolytic agents or agents stimulating lipolysis, adipogenic agents, etc. Additional examples can be found in *CTFA International Cosmetic Ingredient Dictionary & Handbook,* 12th Edition (2008).

In one embodiment, the invention provides a cosmetic or pharmaceutical composition comprising a compound of formula (I) and a pharmaceutically or cosmetically effective amount of an adjuvant selected from the group consisting of: (i) anti-wrinkle-agent, botox-like agent and/or anti-aging agent; (ii) firming agent, skin elasticity agent and/or restructuring agent; (iii) moisturizing agent; (iv) anti-photoaging agent, and/or blue-light protector agent; (v) DNA protecting agent, DNA repair agent, and/or stem cell protecting agent; (vi) free radical scavengers and/or anti-glycation agent, detoxifying agent, antioxidant and/or anti-pollution agents; and/or combinations thereof.

In a particular embodiment, the anti-wrinkle agent, botox-like agent and/or anti-aging agent is selected from thee group consisting of Matrixyl® [INCI: Palmitoyl Pentapeptide-4], Matrixyl® 3000® [INCI: Palmitoyl Tetrapeptide-7, Palmitoyl Oligopeptide], Matrixyl® Synthe'6 [INCI: Glycerin, Water, Hydroxypropyl Cyclodextrin, Palmitoyl Tripeptide-38], Matrixyl® Morphomics™ [INCI: Pentylene Glycol, Caprylyl Glycol], Essenskin™ [INCI: calcium hydroxymethionine], Renovage [INCI: Teprenone], Dermaxyl® [INCI: Palmitoyl Oligopeptide], Calmosensine™ [INCI: Butylene Glycol, Acetyl Dipeptide-1 Cetyl Ester], Volulip™ [INCI: Cetearyl Ethylhexanoate, Sorbitan Isostearate, Portulaca Pilosa Extract, Sucrose Cocoate, Palmitoyl Tripeptide-38], Subliskin™ [INCI: Sinorhizobium Meliloti Ferment, Cetyl Hydroxyethyl Cellulose, Lecithin], Biopeptide™ CL [INCI: Palmitoyl Oligopeptide], Biopeptide EL [INCI: Palmitoyl Oligopeptide], Rigin™ [INCI: Palmitoyl Tetrapeptide-3], Biobustyl [INCI: Glyceryl Polymethacrylate, Rahnella/Soy Protein Ferment, Palmitoyl Oligopeptide], Dynalift™ [INCI: Sodium Polystyrene Sulfonate, Sorghum Bicolor Stalk Juice, Glycerin], Idealift™ [INCI: Acetyl Dipeptide-1 Cetyl Ester], Siegesbeckia [INCI: Siegesbeckia Orientales Extract], Ovaliss™ [INCI: Coco-glucoside, Caprylyl Glycol, Alcohol, Glaucine], Juvinity™ [INCI: Geranylgeranyisopropanol], Prolevis™ [INCI: Hydrolyzed Vegetable Protein], Idealift™ [INCI: Hydroxyethylcellulose, Acetyl Dipeptide-1 cetyl ester], Beautifeye™ [INCI: Albizia Julibrissin Bark Extract, Darutoside], Chromocare™ [INCI: Sigesbeckia Orientalis Extract, Rabdosia Rubescens Extract] or Resistem™ [INCI proposed: Globularia Cordifolia Ferment] marketed by Sederma/Croda. Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate™ [INCI: Ceratonia Siliqua (Carob) Gum], Preregen® [INCI: Glycine soja (Soybean) Protein, Oxido Reductases], Pepha-Nutrix™ [INCI: Natural Nutrition Factors], Pepha-Tight™ [INCI: Algae Extract, Pullulan], Pentacare-NA™ [INCI: Hydrolyzed Wheat Gluten, Ceratonia Siliqua Gum], Syn®-Tacks [INCI: Glycerin, Palmitoyl Dipeptide-5 Diaminobutyloyl Hydroxythreonine, Palmitoyl Dipeptide-6 Diaminohydroxybutyrate], BeauActive MTP™ [INCI: Hydrolyzed milk protein], Syn®-TC [INCI: Tetradecyl Aminobutyroylvalylaminobutyric Urea Trifluoroacetate, Palmitoyl Tripeptide-5, Palmitoyl Dipeptide-5 Diaminobutyroyl Hydroxythreonine], Syn®-Hycan [INCI: Tetradecyl Aminobutyroylvalylaminobutyric Urea Trifluoroacetate], Syn®-Glycan [INCI: Tetradecyl Aminobutyroylvalyl-aminobutyric Urea Trifluoroacetate], Regu-Age™ [INCI: Hydrolyzed Rice Bran Protein, Oxido Reductases, Glycine Soja Protein], Pepha-Timp™ [INCI: Human oligopeptide-20], Pepha-Age™ [INCI: Dunaliella Salina Extract], Colhibin™ [INCI: Hydrolyzed Rice Protein], Elhibin [INCI: Glycine Soja Protein, Disodium cocoamphodiacetate] or All-Q™ Plus [INCI: Ubiquinone, Tocopheryl Acetate] marketed by Pentapharm/DSM; Myoxinol™ [INCI: Hydrolyzed Hibiscus esculentus Extract], Myoxinol™ LS 9736 [INCI: Hydrolyzed Hibiscus esculentus Extract, Dextrin], Synior-age™ [INCI: Acetyl Tetrapeptide-11], Dermican™ [INCI: Acetyl Tetrapeptide-9], DN-AGE® LS [INCI: Cassia alata leaf Extract], Hyalufix GL™ [INCI: Alpinia Galanga Leaf Extract], Neurobiox™ [INCI: Achillea Millefolium Extract,], Deliner™ [INCI: *Zea Mays* (Corn) Kernel Extract], Lys'lastine V™ [INCI: Peucedanum Graveolens (Dill) Extract], Extracellium [INCI: Hydrolyzed Potato Protein], Proteasyl TP LS 8657™ [INCI: Pisum Sativum Extract], Flavagrum PEG™ [INCI: PEG-6 Isostearate, Hesperetin Laurate], Micromerol™ [INCI: Pyrus Malus Fruit Extract], Extracellium™ [INCI: Hydrolyzed Potato Protein], Marine Filling Spheres [INCI: Pentaerythrityl Tetraisostearate, Silica Dimethyl Silylate, Sodium Chondroitin Sulfate, Atelocollagen], Triactigen™ [INCI: Mannitol, Cyclodextrin, Yeast Extract, Disodium Succinate], Eterniskin™ [INCI: Grifola Frondosa Fruiting Body Extract, Maltodextrin], Ascotide™ [INCI: Ascorbyl Phosphate Succinoyl Pentapeptide-12], Hyalurosmooth™ [INCI: Cassia Angustifolia Seed Polysaccharide], Indinyl CA™ [INCI: Cassia Angustifolia Seed Polysaccharide], Arganyl [INCI: Argania Spinosa Leaf Extract], Sphingoceryl Veg™ [INCI: Phyto-ceramides], Vit-A-Like [INCI: Vigna Acontifolia Seed Extract], Peptiskin™ [INCI: Arginine/Lysine polypeptide], Prodejine™ [INCI: Mannitol, Cyclodextrin, Yeast Extract, Disodium Succinate], Aqu'Activ™ [INCI: Behenyl Alcohol, Glyceryl Oleate, Cocamide MIPA, Calcium Citrate], Elestan™ [INCI: Glycerin, Manilkara Leaf Extract], Hibiscin HP™ [INCI: Hibiscus Esculentus Seed Extract], Collalift®18 [INCI: Khaya Senegalensis Bark], Collrepair™ DG [INCI: Hexylene Glycol, Niacin] or Litchiderm™ [INCI: Litchi Chinensis Pericarp Extract] marketed by Laboratoires Sérobiologiques/Cognis/BASF; Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline® [INCI: Acetyl Hexapeptide-30], Aldenine® [INCI: Hydrolized Wheat Protein, Hydrolized Soy Protein, Tripeptide-1], Preventhelia® [INCI: Diaminopropionoyl Tripeptide-33], Decorinyl® [INCI: Tripeptide-10 Citrulline], Decorinol® [INCI: Tripeptide-9 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase® [INCI: Acetylarginyltriptophyl Diphenylglycine], Thermostressine® [INCI: Acetyl Tetrapeptide-22], Lipochroman™ [INCI: Dimethylmethoxy Chromanol], Chromabright® [INCI: Dimethylmethoxy Chromanyl Palmitate], Antarcticine® [INCI: Pseudoalteromonas Ferment Extract], dGlyage® [INCI: Lysine HCl, Lecithin, Tripeptide-9 Citrulline], Vilastene™ [INCI: Lysine HCl, Lecithin, Tripeptide-10 Citrulline], Hyadisine® [INCI: Pseudoalteromonas Ferment Extract], Hyanify™ [INCI: Saccharide Isomerate], Diffuporine® [INCI: Acetyl Hexapeptide-37], Silusyne® [INCI: Soybean (Glycine Soja) Oil, Sorbitan Sesquioleate, Isohexadecane, Sodium Hyaluronate, Lauryldimonium Hydroxypropyl Hydrolized Soy Protein, Acetyl Hexapeptide-39], Adifyline® [INCI: Acetyl Hexapeptide-38], Delisens™ [INCI: Acetyl Hexapeptide-46], Telangyn™ [INCI: Acetyl Tetrapeptide-40], Reproage™ peptide [INCI: Acetyl Hexapeptide-8], Cellynkage™ marine ingredient [INCI: Saccharide Isomerate], Eyedeline™ marine ingredient [INCI: Plankton Extract], Uplevity™ [INCI: Acetyl Tetrapeptide-2], Seacode™ marine ingredient [INCI: Pseudoalteromonas Ferment Extract] or Serilesine® peptide solution [INCI: Hexapeptide-10] marketed by Lipotec/Lubrizol; Sirtalice™ [INCI: Bacillus Ferment], Epitensive™ [INCI: Nicotiana Benthamiana Hexapeptide-40 SH-Oligopeptide-1], Scelleye™ [INCI: Nicotiana Benthamiana SH-Oligopeptide-2], Seadermium™ [INCI: Aqua, Glycerin, Bacillus Ferment], Pauseile [INCI: Aqua, Glycerin, Bacillus Ferment] or Neoclair Pro™ [INCI: Aqua, Glycerin, Caprylyl Glycol, Acetyl Tetrapeptide-2] marketed by Lipotrue; Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: Phoenix dactylifera (Date) Seed Extract], Phytoquintescine™ [INCI: Einkorn (*Triticum monococcum*) Extract], Quintescine™ IS [INCI: Dipeptide-4], Peptide Vinci 01™ [INCI: Penta-decapeptide-1], Peptide Vinci 02™ [INCI: Hexapeptide-3], Aquarize IS™ [INCI: Hydrolyzed Rice Extract], Lanablue [INCI: Algae extract], Ederline™ [INCI: Pyrus Malus (Apple) Seed Extract], Dynachondrine™ ISR [INCI:Hydrolized Soy Protein], Prolixir S20™ [INCI: Dimer Tripeptide-43], Phytocohesine™ PSP [INCI: Sodium Beta-Sitosteryl Sulfate, Beta-Sitosterol], Perenityl™ IS [INCI: Pyrus Communis (Pear) Seed Extract], Caspaline 14™ [INCI:Hexapeptide-42], Peptide Q10™ [INCI: Pentapeptide-34 Trifluoroacetate], Survixyl IS™ [INCI: Pentapeptide-31], ChroNOgen™ [INCI: Tetrapeptide-26], Elixiance™ [INCI: Schinus Molle Extract], Harmoniance™ [INCI: Nelumbo Nucifera Flower Extract], Serenityl™ [INCI: Marsdenia Condurango Bark Extract], Natriance Wrinkle-less™ [INCI: Hydrolyzed Corn Protein], Phytoneomatrix™ [INCI: Hydrolyzed Soybean Extract], Prolixir ICE™ [INCI: Hydrolyzed Rice Protein], PhytoRNx Baobab™ [INCI: Hydrolyzed Adansonia Digitata Extract], Natriance™ Renovate Extract [INCI: Hydrolyzed Linseed Extract], Natriance™ Self-Hydrate Extract [INCI: Pisum Sativum Extract], Actopontine YST™ [INCI: Hydrolyzed Yeast Protein] or Telosense™ [proposed INCI: Hydrolyzed Soy Protein, Hydrolyzed Yeast Protein] marketed by Vincience/ISP/Ashland; BONT-L-Peptide [INCI: Palmitoyl Hexapeptide-19], TIMP Peptide [INCI: Acetylhexapeptide-20], ECM Moduline™ [INCI: Palmitoyl Tripeptide-28], Renaissance™ [INCI: Hydrolyzed Wheat Protein, Palmitoyl Decapeptide-21, Decapeptide-22, Oligopeptide-78, Zinc Palmitoyl Nonapeptide-14] or X50 Antiaging™ [INCI: Lactic Acid/glycolic Acid Copolymer, Polyvinyl Alcohol, Copper Palmitoyl Heptapeptide-14, Heptapeptide-15 Palmitate] marketed by Infinitec Activos; EquiStat™ [INCI: *Pyrus malus* Fruit Extract, Glycine soja Seed Extract], Juvenesce™ [INCI: Ethoxydiglicol and Caprylic Triglyceride, Retinol, Ursolic Acid, Phytonadione, Ilomastat], Ursolisome™ [INCI: Lecithin, Ursolic Acid, Atelocollagen, Xanthan Gum, Sodium chondroitin sulfate], Basaline™ [INCI: Hydrolyzed Malt Extract], Phytokine™ [INCI: Hydrolyzed Soy Protein], marketed by Coletica/Engelhard/BASF; Ameliox™ [INCI: Carnosine, Tocopherol, *Silybum marianum* Fruit Extract] or PhytoCellTec™ Malus Domestica [INCI: *Malus domestica* Fruit Cell Culture], Lipobelle Soyaglicane™ [INCI: Soy Isoflavones], RoyalEpigen™ P5 [INCI: Butyrospermum Parkii BUtter, Hydrogenated Lecithin, Maltodextrin, Pentapeptide-48, Phenethyl Alcohol, Ethylhexylglycerin, Glycerin, Water] or DermCom™ [INCI: Crocus Chrysanthus Bulb Extract, Acacia Senegal Gum, Water] marketed by Mibelle Biochemistry; ActiMatrix™ [INCI: Peptide based mushroom Extract], Peptamide 6 [INCI: Hexapeptide-11] marketed by Active Organics/Arch; and combinations thereof.

In another embodiment, the firming agent, skin elasticity agent and/or restructuring agent is selected, from the group consisting of Argassential™ [INCI: C10-16 Alkyl Glucoside, Dicaprylyl Ether, Glycerin] or Replexium™ BC [INCI: Dimethyl Isosorbide, Polysorbate 20, Water, Acetyl Tetrapeptide-11, Acetyl Tetrapeptide-9] marketed by BASF; Prolevis™ [INCI: Hydrolyzed Vegetable Protein] or Poretect [INCI: Caprylic/capric Triglyceride, Sorbitan Trioleate, Apium Graveolens Seed Extract, Linum Usitatissimum Seed Extract] marketed by Sederma/Croda; Actifirm™ Ultra Advanced botanical ingredient [INCI: Centella Asiatica Extract, Rosmarinus Officinalis Leaf Extract, Dipropylene Glycol, Alcohol, Echinacea Angustifolia Leaf Extract] or Actifcol™ Advanced botanical ingredient [INCI: Water, Glycerin, Sodium Citrate, Lentinus Edodes Extract, Potassium Sorbate, Sodium Benzoate, Phytic Acid] marketed by Lipotec/Lubrizol; Densorphin™ [INCI: Vitex Agnus Castus Extract, Aqua, Maltodextrin] or PhytoCellTec™ Nunatak® [INCI: Isomalt, Aqua, Saponaria Pumila Callus Culture Extract, Lecithin] marketed by Mibelle; and combinations thereof.

In another embodiment, the moisturizing agent is selected from the group consisting of Aqua Shuttle™ [INCI: Sorbitol, Laminaria Digitata Extract, Diatomaceous Earth] marketed by Infinitec; Aqua-Osmoline™ [INCI: Ceratonia Siliqua (Carob) Seed Extract] marketed by Vincience/ISP/Ashland; Hydralphatine™ Asia [INCI: Hydrogenated Starch Hydrolysate, Panthenol, Bambusa Vulgaris Shoot Extract, Nelumbo Nucifera Flower Extract, Nymphaea Alba Root Extract] or Hydraporine™ [INCI: Betaine, Hydrogenated Lecithin, Honey, Pectin] marketed by Lucas Meyer Cosmetics/Unipex; PatcH2O™ [INCI: Trehalose, Urea, Serine, Glyceryl Polyacrylate, Algin, Sodium Hyaluronate, Pullulan], Aqu'Activ™ [INCI: Behenyl Alcohol, Glyceryl Oleate, Cocamide MIPA], Irwinol® [INCI: Octyldodecanol, Irvingia Gabonensis Kernel Butter, Hydrogenated Coco-Glycerides], Lipodermol®) [INCI: Octyldodecanol, Arachidyl Propionate, Tocopheryl Acetate, Retinyl Palmitate, Ethyl Linoleate, Ethyl Linolenate] or Seanamin® SU [INCI: Sorbitol, Algae Extract, Chrondrus Crispus (Carrageenan), Fucus Vesiculosus Extract, Algin] marketed by L. Serobiologiques/Cognis/BASF; Snow Algae Powder [INCI: Coenochloris Signiensis Extract] marketed by Mibelle; Hyasol BT™ [INCI: Sodium Hyaluronate], Syn-Up™ [INCI: Benzylsulfonyl D-Seryl Homophenylalanine Amidinobenzamide Acetate] or Pentavitin® [INCI: Saccharide Isomerate] marketed by Pentapharm/DSM; Aqualance™ [INCI: Erythritol, Homarine HCl], Hydraprotectol™ [INCI: Glyceryl Polymethacrylate, Aleuritic Acid, Yeast Extract (Faex), Glycoprotein], Moist 24™ [INCI: Imperata Cylindrica Root Extract], Optim Hyal™ [INCI: Hydrolyzed Yeast Extract, Cetyl Hydroxyethylcellulose, Polyglucuronic Acid], Osmocide® 4 [INCI: Glycerin, Acrylates/C10-30 Alkyl Acrylate Crosspolymer] or Revidrate™ [INCI: Ethylhexyl Palmitate, Sorbitan Oleate, Sorbitan Laureate, Myristyl Malate Phosphonic Acid] marketed by Sederma/Croda; Xpertmoist® molecular film [INCI: Glycerin, Pseudoalteromonas Ferment Extract, Xanthan Gum, Proline, Alanine, Serine, Ethylhexylglycerin, Caprylyl Glycol] or Actizyme® GL advanced botanical ingredient [INCI: Glycerin, Mucor miehei extract, Aqua, Sodium Citrate, Potassium Sorbate, Sodium Benzoate, Phytic Acid] marketed by Lipotec/Lubrizol; and combinations thereof.

In another embodiment, the anti-photoaging agent, and/or blue-light protector agent is selected from the group consisting of Algaktiv Genofix™ CPD [INCI: Plankton Extract, Aqua, Lecithin] marketed by Greenaltech; Blumilight™ Biofunctional [INCI proposed: Water/Aqua (and) Butylene Glycol (and) Theobroma Cacao (Cocoa) Seed Extract] marketed by Ashland; Lys'Sun™ [INCI: Hamamelis Virginiana Leaf Extract, Aqua, Pentylene Glycol, Caprylyl Glycol, Xanthan Gum] marketed by BASF; Vitachelox™ [INCI: Vitis Vinifera Seed Extract, Camellia Sinensis Leaf Extract, Quercus Robur Wood Extract] marketed by Indena; L-VCG™ [INCI: Ascorbyl Glucoside]marketed by Freshine Bio-technology; Lumicease™ blue ingredient [INCI: Glycerin, Aqua, Hydrolyzed Pea Protein, Glucose, Sodium Chloride] marketed by Lipotec/Lubrizol; Lightwaves Defense [JS+M]™ [INCI: Jasminum Sambac Leaf Cell Extract] marketed by Naolys; Blue Oleoactif™ [INCI: Glycine Soja Oil, Polyglyceryl-3 Diisostearate, Oryza Sativa Germ Extract, Oryza Sativa Extract] marketed by Oleos-Hallstar; Majestem™ [INCI: Glycerin, Leontopodium Alpinum Callus Culture Extract, Xanthan Gum] or Senestem™ [INCI: Glycerin, Plantago Lanceolata Leaf Extract, Xanthan Gum] marketed by Sederma; Blueshield™ [INCI: Glycerin, Capsicum Annuum Fruit Extract, Xanthan Gum] marketed by Solabia; and combinations thereof.

In another embodiment, a DNA protecting agent, DNA repair agent, and/or stem cell protecting agent is selected from the group consisting of: GP4G SP™ [INCI: Aqua, Glycerin, Aretmia Extract], Heliostatine™ [INCI: Aqua, Glycerin, Pisum Sativum Extract], Orsirtine™ [INCI: Aqua, Glycerin, Oryza Sativa Extract], Chronogen™ [INCI: Water, Butylene Glycol, Tetrapeptide (INCI proposed)], Survixyl IS™ [INCI: Water, Butylene Glycol, Pentapeptide-31] and Chrondricare™ [INCI: Aqua, Butylene Glycol Pentapeptide-28] marketed by Vincience/ISP/Ashland; Lanacityn® [INCI: Glycerin, Aqua, Alteromonas ferment extract, *Chysanthellum indicum* extract] or Melinoil™ [INCI: Isopropyl Palmitate, Lecithin, Aqua, Acetyl Hexapeptide-1] marketed by Atrium Innovations/Lucas Meyer Cosmetics; Repair Complex™ [INCI: Bifida Ferment Lysate] marketed by CLR; Phycojuvenine™ [INCI: Laminaria Digitata] marketed by Codif; Unirepair T-43™ [INCI: Butylene Glycol, Acetyl Tyrosine, Proline, Hydrolyzed Vegetable Protein, Adenosine Triphosphate] marketed by Induchem; Dragosine™ [INCI: Carnosine] marketed by Symrise; DN-Age™ [INCI: Cassia Alata Leaf Extract] marketed by Laboratories Serobiologiques/Cognis/BASF; Helioguard™ [INCI: Porphyra Umbilicalis encapsulated into liposomes], PhytoCellTec™ Malus Domestica [INCI: PhytoCellTec Malus Domestica] or PhytoCellTec™ Argan [INCI: Argania Spinosa Sprout Cell Extract, Isomalt, Lecithin, Sodium Benzoate, Aqua] marketed by Mibelle Biochemistry; Pepha-Protect™ [INCI: Water Melon Extract] marketed by Pentapharm/DSM; Celligent™ [INCI: Helianthus Annuus Seed Oil, Ethyl Ferulate, Polyglyceryl-5 Trioleate, Rosmarinus Officinalis Leaf Extract, Aqua, Disodium Uridine Phosphate] or Defensil™ [INCI: Octyl Dodecanol, Echium Plantagineum Seed Oil, Cardiospermum Halicacabum Extract, Helianthus Annuus Seed Oil Unsaponifiables] marketed by Rahn; Venuceane™ [INCI: Thermus Thermophilus Ferment, Glycerin], UV-Soft [INCI: Yeast Extract], Renovage™ [INCI: Caprylic/Capric Triglyceride, Teprenone], Juvinity™ [INCI: Caprylic/Capric Triglyceride, Geranylgeranylpropanol (proposed)], Phytessence™ Holyherb [INCI: Butylene Glycol, Eriodictyon Californicum (Holyherb) Flower/Leaf/Stem Extract] or Resistem™ [INCI: Glycerin, Globularia Cordifolia Ferment] marketed by Sederma/Croda; Infraguard™ [INCI: Caesalpinia Spinosa Fruit Pod Extract, Propylene Glycol, Aqua, Helianthus Annuus Sprout Extract, Sodium Benzoate, Phenoxyethanol] marketed by Mibelle; Heliomoduline™ [INCI: Low molecular weight peptides from cottonseed] or Stem-C-Guard™ [Hydrolyzed Pea] marketed by Silab; and combinations thereof.

In another embodiment, the reactive carbonyl species scavenger, free radical scavengers and/or anti-glycation agent, detoxifying agent, antioxidant and/or anti-pollution agent is selected, for example and not restricted to, from the group formed by carnosine and its derivatives; GHK™ [INCI: Tripeptide-1] and its salts and/or derivatives or Quintescine™ IS [INCI: Dipeptide-4] marketed by Vincience/ISP/Ashland; Preregen™ [INCI: Glycine Soja (Soybean) Protein, Oxido Reductases], Edelweiss™ GC [INCI: Leontopodium Alpinum Extract], Lipogard™ [INCI: Squalane, Ubiquinone], Nectapure™ [INCI: Buddleja Davidii Extract, Thymus Vulgaris Extract], Alpaflor™ Nectapure [INCI: Buddleja Davidii Extract, Thymus Vulgaris Extract, Glycerin, Water] or Dismutin-BTT™ [INCI: Highly purified SOD from a natural yeast strain of *Saccharomyces cerevisiae*] marketed by Pentapharm/DSM; Preventhelia® [INCI: Diaminopropionoyl Tripeptide-33], Aldenine® [INCI: Hydrolized Wheat Protein, Hydrolized Soy Protein, Tripeptide 1], Lipochroman™ [INCI: Dimethylmethoxy Chromanol], Thermostressine® [INCI: Acetyl Tetrapeptide-22] Pollushield™ functional ingredient [INCI: Diisopropyl Adipate, Lecithin, Acrylic Acid/Acrylamidomethyl Propane Sulfonic Acid Copolymer, Dimethylmethoxy Chromanol, Xanthan Gum] or Bodyfensine® [INCI: Acetyl Dipeptide-3 Aminohexanoate] marketed by Lipotec/Lubrizol; Sunactyl™ [INCI: Mannitol, Pisum Sativum Extract, Histidine HCl, Arginine, Cyclodextrin, Dextrin, Yeast Extract, Acetyl Tyrosine, Pyridoxine HCl, Khaya Senegalensis Bark Extract, Nicotinamide, Adenine Dinucleotide, Disodium Succinate, Aspartic Acid], Imidinyl™ [INCI: Tamarindus Indica Seed Polysaccharide], Phystrogene™ [INCI: Butylene Glycol, Malva Sylvestris (Mallow) Extract, Xanthan Gum] or Purisoft™ [INCI: Moringa Pterogysperma Seed Extract] marketed by Laboratoires Sérobiologiques/Cognis/BASF; AquaCacteen™ [INCI: Glycerin, Opuntia Ficus Indica Stem Extract, Phenoxyethanol, Aqua], Trimoist™ (KM F) [INCI: Sodium Stearoyl Lactylate, Cetyl alcohol, Olus Vegetable oil, Tocopheryl acetate, Glycerin, Glycine soja sterol, Sodium lactate, Sodium barboxymethyl betaglucan, Carnosine, Lactic Acid], MelanoBronze™ [INCI: Vitex Agnus Castus Extract (Monk's pepper berries extract (phyto-endorphins)), Acetyl Tyrosine], CM-Glucan™ [INCI: Sodium Carobxymethyl Betaglucan, Phenoxyethanol, SunActin™ [INCI: Helianthus Annuus (Sunflower) Sprout Extract, Tocopherols, Glycerin, Lecithin, Phenoxyethanol, Aqua], GSP-T Skin™ [INCI: Glycerin, Alcohol, Aqua, PEG-40 Hydrogenated Castor Oil, Vitis Vinifera (Grape) Seed Extract] or Detoxophane™ [INCI: Lepidium Sativum Sprout Extract, Lecithin, Phenoxyethanol, Glycerin, Water] marketed by Mibelle Biochemistry; Bacocalmine™ [INCI: PEG-8, Bacopa Monniera Extract, Water (Aqua), Hydroxyethylcellulose], Kombuchka™ [INCI: Saccharomyces/Xylinum Black Tea Ferment, Glycerin, Hydroxyethyl cellulose], Citystem™ [INCI: Glycerin, Marrubium Vulgare Extract] or Prodizia™ [INCI: Albizia Julibrissin Extract, Glycerin] marketed by Sederma/Croda; Extramel™ C [INCI: Hydroxypropyltrimonium Maltodextrin Crosspolymer, Cucumis Melo (Melon) Fruit Extract] marketed by Seppic; Defensine™ [INCI: Triticum Vulgare Germ Extract], Apolluskin® [INCI: *Taraxacum officinale* (Dandelion) Extract], Detoxyl® [INCI: Water, Butylene Glycol, *Butyrospermum parkii* (Shea Butter) Seedcake Extract] or Antiglyskin™ [INCI: Aqua, Helianthus Annuus Seed Extract] marketed by Silab; and combinations thereof.

The compositions of the invention may be for use in any of the applications or uses discussed above under the heading "Applications".

In another aspect, the invention provides kit for use in a cosmetic, non-therapeutic method of treatment and/or care of the skin comprising:
 (i) a composition comprising Botulinum toxin;
 (ii) optionally, a composition comprising Ac-Glu-Glu-Met-Gln-Arg-Arg-NH$_2$; and
 (iii) a cosmetic composition comprising a compound of formula (I), (II) or (III).

The (i) composition comprising Botulinum toxin, (ii) composition comprising Ac-Glu-Glu-Met-Gln-Arg-Arg-$NH_2$, if present, and the (iii) composition comprising the compound of the invention according to the first aspect, can be in the same or separate containers. In one embodiment, the kit can further comprise means to apply the compositions to the skin. For instance, the kit can comprise means suchs a syringes or microneedles.

The invention is illustrated by the following non-limiting examples.

EXAMPLES

General Methods

Abbreviations

The abbreviations used for amino acids follow the 1983 IUPAC-IUB Joint Commission on Biochemical Nomenclature recommendations outlined in *Eur. J. Biochem.* (1984) 138:9-37.

(R), resin; 2-CITrt-(R), 2-chlorotrityl resin; Ac, acetyl; AcOH, acetic acid; Ala, alanine; AM, 2-[4-aminomethyl-(2, 4-dimethoxyphenyl)] phenoxyacetic acid; Arg, arginine; Asn, asparagine; Asp, aspartic acid; Boc, tert-butyloxycarbonyl; DCM, dichloromethane; DIEA, N,N'-diisopropylethylamine; DIPCDI, N,N'-diisopropylcarbodiimide; DMF, N,N-dimethylformamide; ESI-MS, electrospray ionization mass spectrometry; Fmoc, 9-flluorenylmethyloxycarbonyl; Gln, glutamine; Glu, glutamic acid; Gly, Glycine; His, histidine; HOBt, 1-hydroxybenzotriazole; HPLC, high performance liquid chromatography; Ile, isoleucine; KOH, potassium hydroxide; Leu, leucine; Lys, lysine; MBHA, p-methylbenzhydrylamine; MeCN, acetonitrile; MeOH, methanol; Met, Methionine; Myr, myristoyl; Palm, palmitoyl; Pbf, 2,2,4,6,7-pentamethyldihydrobenzofuran-5-sulfonyl; Pro, proline; Ser, serine; tBu, tert-butyl; TFA, trifluoroacetic acid; Thr threonine; Trt, trithyl; Val, valine.

Chemical Synthesis

All synthetic processes are carried out in polypropylene syringes fitted with porous polyethylene discs. The coupling protocol is carried out following the standard protocols founded in bibliography and the solvents and soluble reagents are removed by suction. The Fmoc group is removed with piperidine-DMF (2:8, v/v) (1×1 min, 1×5 min, 5 ml/g resin) [Lloyd-Williams P. et al. (1997) "*Chemical Approaches to the Synthesis of Peptides and Proteins*" CRC, Boca Raton (Fla., USA)]. Washes between stages of deprotection, coupling and, again, deprotection, are carried out with DMF (3×1 min) each time using 10 ml solvent/g resin. Coupling reactions are performed with 3 ml solvent/g resin. The control of the couplings is performed by carrying out the ninhydrin test [Kaiser E. et al., *Anal. Biochem.* (1970), 34: 595-598] or chloranil test [Christensen T., *Acta Chem. Scand.*, (1979), 33B, 763-766]. The coupling reactions are repeated as the desired peptide is synthesized. All synthetic reactions and washes are carried out at 25° C.

It is known by the skilled person that some amino acids are used with their functional groups in side chains protected. For instance, non-limiting examples of protecting groups are:

tBu, tert-butyl for amino acid Glu; and

Pbf, 2,2,4,6,7-pentamethyldihydrobenzofuran-5-sulfonyl for aminoacid Arg; and

Trt, trithyl for amino acids Gln.

HPLC chromatographic analysis is carried out with Shimadzu equipment (Kyoto, Japan) using a reversed-phase column thermostatized at 30° C. (50×4.6 mm, Kromasil C18, 3.5 μm, Akzo Nobel, Sweden). The elution is carried out using a gradient of acetonitrile (+0.07% TFA) in water (+0.1% TFA) at a flow rate of 1.6 mL/min and detection is carried out at 220 nm. The electrospray ionization mass spectrometry is carried out in a WATERS Alliance ZQ 2000 detector using a mixture of MeCN:$H_2O$ 4:1 (+0.1% TFA) as the mobile phase and a flow rate of 0.3 ml/min.

Example 1

Obtaining Fmoc-$W_m$-$X_n$-$AA_1$-$AA_2$-$AA_3$-$AA_4$-$Y_p$-$Z_q$-AM-MBHA-(R), Wherein $AA_1$ is L-Asp; $AA_2$ is L-Val; $AA_3$ is L-Tyr; $AA_4$ is L-Lys and n, m, p and q are Each 0.

Weights have been normalized. Fmoc-AM-pMBHA resin is treated with piperidine:DMF according to the described general protocol in order to remove the Fmoc group. 5 equiv of Fmoc-L-Lys(Boc)-OH is incorporated onto the deprotected resin in the presence of 5.5 equiv of DIPCDI and 5 equiv of HOBt using DMF as a solvent for 1 hour.

The resin is then washed as described in general methods and the deprotection treatment of the Fmoc group is repeated to couple the next amino acid: 5 equiv of Fmoc-L-Tyr(tBu)-OH; and subsequently 5 equiv of Fmoc-L-Val-OH; 5 equiv of Fmoc-L-Asp(tBu)-OH); are sequentially coupled in the presence of 5 equiv of HOBt and 5.5 equiv of DIPCDI in each coupling step.

After the synthesis, the peptidyl resin is washed with DCM (3×1 min).

By following the described method, it is possible to obtain different sequences changing the desired amino acids to be coupled.

Example 2

Obtaining Fmoc-$W_m$-$X_n$-$AA_1$-$AA_2$-$AA_3$-$AA_4$-$AA_5$-$AA_6$-$Y_p$-$Z_q$-AM-MBHA-(R), Wherein $AA_1$ is L-Ala; $AA_2$ is L-Leu; $AA_3$ is L-Lys; $AA_4$ is L-Pro; $AA_5$ is L-Asn; $AA_6$ is L-Thr; and n, m, p and q are Each 0.

Weights have been normalized. Fmoc-AM-pMBHA resin is treated with piperidine:DMF according to the described general protocol in order to remove the Fmoc group. 5 equiv of Fmoc-L-Thr(tBu)-OH is incorporated onto the deprotected resin in the presence of 5.5 equiv of DIPCDI and 5 equiv of HOBt using DMF as a solvent for 1 hour.

The resin is then washed as described in the general methods and the deprotection treatment of the Fmoc group is repeated to couple the next amino acid: 5 equiv of Fmoc-L-Asn(Trt)-OH; and subsequently 5 equiv of Fmoc-L-Pro-OH; 5 equiv of Fmoc-L-Lys(Boc)-OH; 5 equiv of Fmoc-L-Leu-OH; and finally, 5 equiv of Fmoc-L-Ala-OH are sequentially coupled in the presence of 5 equiv of HOBt and 5.5 equiv of DIPCDI in each coupling step.

After the synthesis, the peptidyl resin is washed with DCM (3×1 min).

By following the described method is possible to obtain different sequences changing the desired amino acids to be coupled.

Example 3

General Process for Removal of Fmoc N-Terminal Protective Group.

The N-terminal Fmoc group of the peptidyl resins obtained in Examples 1 or 2 is deprotected as described in the general methods (20% piperidine in DMF, 1×1 min+1×5 min). The peptidyl resins are washed with DMF (5×1 min), DCM (3×1 min), diethyl ether (3×1 min) and dried under vacuum.

Example 4

Process for Introducing the $R_1$ Palmitoyl Group onto the Peptidyl Resins Obtained in Example 3.

5 equiv of palmitic acid pre-dissolved in DMF (1 ml) is added respectively of each of the peptidyl resins obtained in Example 3, in the presence of HOBt and DIPCDI. The mixture is allowed to react for 3 hours, after which the resin is washed with DMF (3×1 min), DCM (3×1 min), diethyl ether (3×1 min) and is dried under vacuum.

Example 5

Process for Introducing the $R_1$ Acetyl Group onto the Peptidyl Resins Obtained in Example 3.

Each of the peptidyl resins obtained in Example 3 are treated with acetic anhydride in the presence of DIEA using DMF as a solvent. The mixture is allowed to react for 30 min, after which the resin is washed with DMF (3×1 min), DCM (3×1 min), diethyl ether (3×1 min) and is dried under vacuum.

Example 6

Cleavage Process from the Polymeric Support of the Peptidyl Resins Obtained in Examples 3, 4 and 5.

Each of the dried peptidyl resins obtained in Examples 3, 4 and 5 are treated with 3 ml of TFA:$H_2O$ (95:5, v/v) for 2 hours at room temperature under stirring. Then they are filtered through a polypropylene syringe fitted with porous polyethylene discs. The filtrate is collected onto cold diethyl ether, and washed 5 times with diethyl ether. The final precipitate is dried under vacuum.

Peptides of general formulas $R_1$-$W_m$-$X_n$-$AA_1$-$AA_2$-$AA_3$-$AA_4$-$Y_p$-$Z_q$-OH, $R_1$-$W_m$-$X_n$-$AA_1$-$AA_2$-$AA_3$-$AA_4$-$NH_2$, $R_1$-$W_m$-$X_n$-$AA_1$-$AA_2$-$AA_3$-$AA_4$-$AA_5$-$AA_6$-$Y_p$-$Z_q$-OH or $R_1$-$W_m$-$X_n$-$AA_1$-$AA_2$-$AA_3$-$AA_4$-$AA_5$-$AA_6$-$Y_p$-$Z_q$-$NH_2$, wherein $R_1$ is H, acetyl or palmitoyl are obtained following this method.

HPLC analyses of the obtained peptides in gradients of MeCN (+0.07% TFA) in $H_2O$ (+0.1% TFA) show a purity exceeding 80% in all cases. The identity of the peptides obtained is confirmed by ESI-MS.

Example 7

In Vitro Quantification of Muscle Bind Like Protein 1 (MBNL1) in Human Skeletal Muscle Cells by Time Resolved Fluorescence Resonance Energy Transfer.

Aging is linked with a muscle mass loss. A loss of function of Muscle bind like protein 1 (MBNL1) is associated with muscle mass loss involved in the ageing process of facial muscles.

MBNL1 induction by the peptides of the invention is evaluated by a Time resolved fluorescence resonance energy transfer (TR-FRET) assay. The aim of this study is to investigate the capacity of peptide candidates to increase MBNL1 in human skeletal muscle cells (hSkMc).

hSkMc (Innoprot) are seeded in 12-well plates at a density of 1.5×10⁴ cells/well in Skeletal Muscle Cell Growth Medium (Promocell). After 72 hours incubation, medium is removed and replaced with Skeletal Muscle Cell Differentiation Medium (Promocell). 48 hours after beginning cell differentiation, fresh differentiation medium with 0.5 mg/ml of test items is added. Treatment is continued for 48 hours and non-treated cells are used as basal control. After 48 hours of treatment, cell medium is removed and added cell lysis buffer to wells. Immediately, plates are kept at −80° C. in order to improve protein extraction during the defrosting process. After 72 hours, cells are lysated by shaking the plates in an orbital rotor at room temperature for 45 minutes. Next, cell lysates are collected and assayed to quantify the level of MBNL1 protein and total protein concentration.

MBNL1 protein levels measurement is performed with Human MBNL1 Assay Kit (Cisbio) according to the manufacturer's protocol. Briefly, the kit is used to perform a TR-FRET for MBNL1 quantification. The protein is detected with the antibodies provided in the kit and quantified by a fluorescence measurement. The quantification is carried out by using a microplate reader (ClarioStar, BMG) set to 665 nm and 620 nm.

Total protein concentration of cell lysate is determined by using Pierce BCA Protein Assay Kit™ (Thermo Scientific) according to manufacturer's protocol. In brief, after adding Working Reagent to the samples and the standards, the samples are incubated. Afterwards, color change is measured with an absorbance microplate reader (Clariostar™, BMG) at 562 nm. The total protein amount is used to normalize the level of MBNL1 protein concentration obtained by the TR-FRET test in the samples.

The results demonstrate that peptides PEP1 (Ac-Asp-Val-Tyr-Lys-NH$_2$) and PEP2 (H-Ala-Leu-Lys-Pro-Asn-Thr-NH$_2$) of the invention increase MBNL1 levels when compared to the basal control (FIG. 1). It is believed that the enhancement of MBNL1 protein slows the muscle mass loss during aging, thus avoiding the appearance of sagging face skin in older people.

Example 8

In Vitro Quantification of Muscle Bind Like Protein 1 (MBNL1) in Human Dermal Fibroblasts by Immunofluorescence.

An increase of collagen synthesis is considered beneficial to reduce aging signs. Muscle bind like protein 1 (MBNL1) in fibroblast activates its transdifferentiation to myofibroblast. These cells can release a higher amount of extracellular matrix proteins such as collagen, elastin or fibronectin preventing wrinkle appearance.

MBNL1 induction by the peptides of the invention is evaluated by an Immunofluorescence assay. The aim of this study is to investigate the capacity of peptide candidates to increase MBNL1 in human dermal fibroblasts (HDF).

Figure 2:
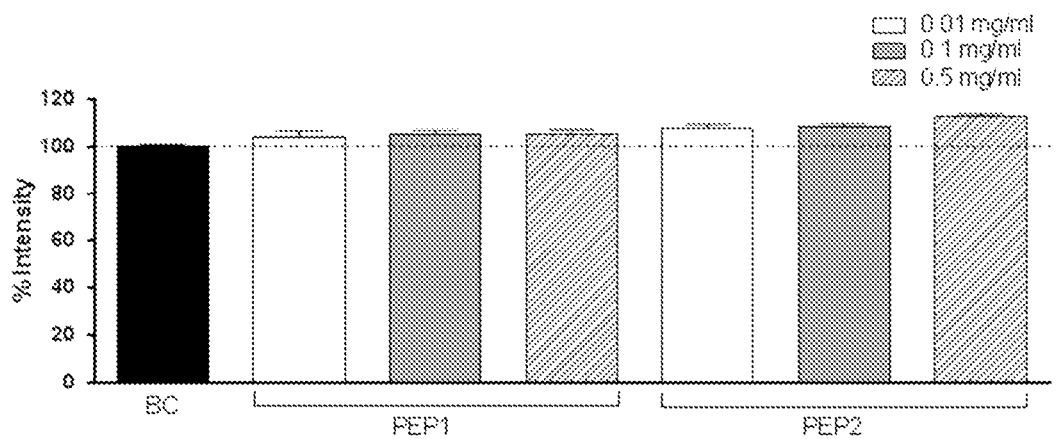
FIG. 2 shows levels of MBNL1 protein present in human dermal fibroblasts measured using an immunofluorescence assay. The measurements are made on samples of human dermal fibroblasts treated with a compound of the invention and for a control sample of human dermal fibroblasts not treated with a compound of the invention (Example 8). Abbreviations: BC, basal control.
Figure 3:
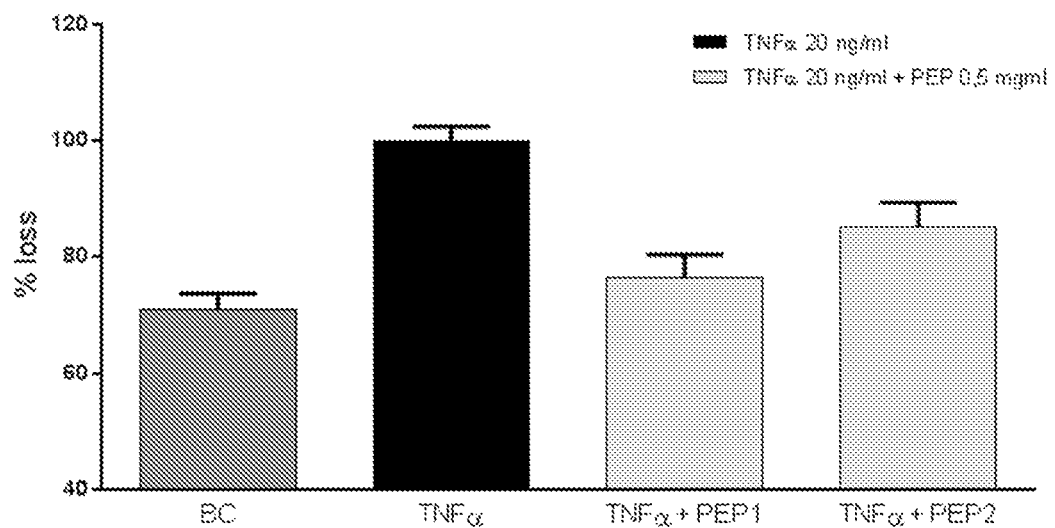
FIG. 3 shows levels of muscle mass loss in human skeletal muscle cells measured using an immunofluorescence assay. The measurements are made on samples of human skeletal muscle cells treated with a compound of the invention and for a control sample of human skeletal muscle cells not treated with a compound of the invention (Example 9). Abbreviations: BC, basal control.

HDF (Cascade) are seeded in 96-well plates at a density of 8×10$^3$ cells/well in Fibroblast Growth Medium (Promocell). After 48 hours incubation, medium is removed and fresh medium with 1, 0.5 and 0.01 mg/ml of test items is added. Treatment is continued for 24 hours and non-treated cells are used as basal control. After 24 hours of treatment, an immunofluorescence is performed. Cells are fixed 15 minutes with 4% Paraformaldehide (Sigma), permeated 15 minutes with 1% Triton X-100 (Sigma) and then blocked with 5% Bovine Serum Albumin (Sigma). Next, primary antibody Anti-MBNL1 Rabbit (Sigma) is added and incubated for 2 hours. After that, secondary antibody Alexa Fluor™ 488 goat anti-rabbit IgG (Life Technologies) is added and incubated for 1 hour. To stain nuclei, Hoechst (Life Technologies) is added and incubated for 10 minutes. Finally, MBNL1 cell nuclei fluorescence intensity and nuclei number are measured by Operetta™ (Perkin Elmer). Fluorescence is normalized by cell nuclei and results are represented respect to basal control. Results are shown in FIG. 2.

The results demonstrate that peptides PEP1 (Ac-Asp-Val-Tyr-Lys-NH$_2$) and PEP2 (H-Ala-Leu-Lys-Pro-Asn-Thr-NH$_2$) of the invention increase MBNL1 levels when compared to the basal control.

Example 9

In Vitro Prevention of Muscle Mass Loss Induced in Human Skeletal Muscle Cells by Immunofluorescence.

Muscle mass loss is related to facial muscle aging. It has been suggested that loss of function of Muscle bind like protein 1 (MBNL1) in muscle cells could be related with muscle mass loss in aging. It has also been described in literature that myotube diameter in muscle cells is an indicator of muscular mass loss when it is under 20 μm.

Myosin heavy chain (MHyC) is used as a morphologic marker of differentiated myotubes allowing the measurement of their diameter, and therefore knowing their degree of mass loss. Tumor necrosis factor α (TNF-α) has been described in the literature as a muscle mass loss inductor.

Figure 4:
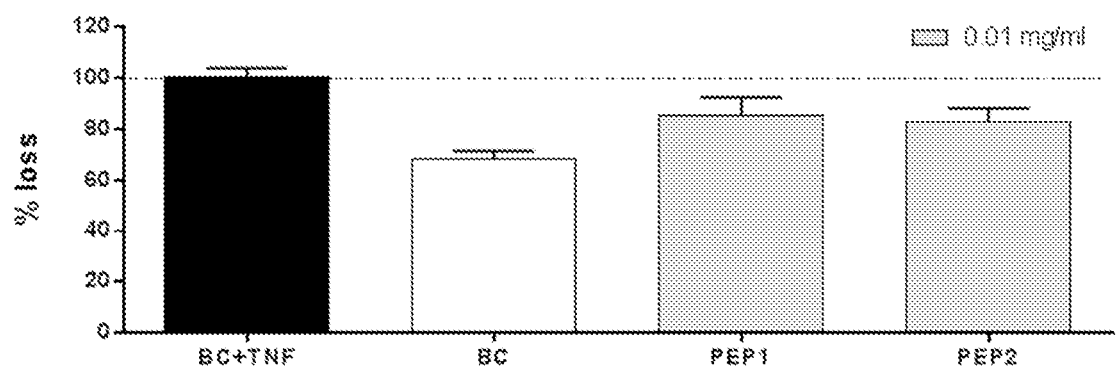
FIG. 4 shows percentage of muscle mass loss in human skeletal muscle cells measured using an immunofluorescence assay. The measurements are made on samples of human skeletal muscle cells treated with tumor necrosis factor alpha (TNFα) and either (i) treated with a compound of the invention or (ii) not treated with a compound of the invention. Results are also compared with human skeletal muscle cells that are neither treated with TNFα nor treated with a compound of the invention (Example 10). Abbreviations: BC+TNF, Basal control with 20 mg/ml of TNFα; BC, Basal control.

Muscle mass loss prevention by the peptides of the invention is evaluated by an immunofluorescence assay. The aim of this study is to investigate the capacity of peptide candidates to prevent muscular mass loss in presence of TNF-α in human muscular skeletal cells (hSKMC).

hSKMC (Tebu-Bio) are seeded in 96-well plates at a density of 1.5×10$^4$ cells/well in Skeletal Muscle Cell Growth Medium (Promocell). After 24 hours incubation, medium is replaced with Skeletal Muscle Cell Differentiation Medium (Promocell) and cells are differentiated for 6 days. After this, fresh differentiation medium with 0.5 mg/ml of test items and 20 ng/ml of TNFα (Sigma) is added. Treatment is continued for 48 hours and non-treated cells are used as basal control and 20 ng/ml TNFα treated cells are used as a muscle mass loss control. After 48 hours of treatment, an immunofluorescence is performed. Cells are fixed 15 minutes with 4% Paraformaldehide (Sigma), permeated 15 minutes with 1% Triton™ X-100 (Sigma) and then blocked with 5% Bovine Serum Albumin (Sigma). Next, primary antibody Anti-MHyC mouse (1:100, Vitro) is added and incubated for 2 hours. After that, secondary antibody Alexa Fluor™ 488 goat anti-mouse IgG (1:250, Life Technologies) is added and incubated for 1 hour. Finally, myotube diameter is determined by imaging MHyC staining by Operetta™ (Perkin Elmer). Percentage of mass loss is automatically calculated with Harmony™ (Perkin Elmer) software by classifying myotubes according to their diameter using an atrophic threshold of 20 μm. Results shown in FIG. 4 and are normalized versus TNF-α.

The results demonstrate that peptides PEP1 and PEP2 of the invention prevent mass loss when compared to TNF-α treatment.

Example 10

In Vitro Alleviation of the Effects of Muscle Mass Loss Induced in Human Skeletal Muscle Cells by Immunofluorescence.

Muscle mass loss correction by the peptides of the invention is evaluated by an immunofluorescence assay. The aim of this study is to investigate the capacity of peptide candidates to correct muscular mass loss after treatment with TNF-α in human muscular skeletal cells (hSKMC). Myosin heavy chain (MHyC) is used as a morphologic marker of differentiated myotubes allowing the measurement of their diameter, and therefore knowing their degree of mass loss. Tumor necrosis factor α (TNF-α) has been described in the literature as a muscle mass loss inductor.

hSKMC (Tebu-Bio) are seeded in 96-well plates at a density of 1.5×10$^4$ cells/well in Skeletal Muscle Cell Growth Medium (Promocell). After 24 hours incubation, medium is replaced with Skeletal Muscle Cell Differentiation Medium (Promocell) and cells are differentiated for 6 days. After this, muscular cells mass loss is induced by adding fresh differentiation medium with 20 ng/ml TNFα (Sigma). Non-TNFα treated cells are used as basal mass loss control (BC). After 24 hours of mass loss induction, the culture medium is replaced with fresh differentiation medium comprising 0.01 mg/ml of the peptides of the invention. TNFα treated cells are used as mass loss control (BCN+TNF) and cells non-treated with neither the peptides of the invention items nor TNFα are used as basal mass loss control (BC). Treatment is renewed 24 hours later. After 24 hours after the second treatment, immunofluorescence is determined. Cells are fixed 15 minutes with 4% Paraformaldehide (Sigma), permeated 15 minutes with 1% Triton™ X-100 (Sigma) and then blocked with 5% Bovine Serum Albumin (Sigma). Next, primary antibody Anti-MHyC mouse (1:100, Vitro) is added and incubated overnight at 4° C. After that, secondary antibody Alexa Fluor™ 488 goat anti-mouse IgG (1:250, Life Technologies) is added and incubated for 1 hour. Finally, myotube diameter is determined by imaging MHyC staining by Operetta™ (Perkin Elmer). Percentage of mass loss is automatically calculated with Harmony™ (Perkin Elmer) software by classifying myotubes according to their diameter using a mass loss threshold of 20 µm. Results show in FIG. 4. are normalized versus mass loss control.

The results demonstrate that peptides PEP1 and PEP2 of the invention correct (i.e., reduces) mass loss when compared to basal control treated with TNF-α.

Example 11

In Vitro Study of Type I Collagen Synthesis on Human Dermal Fibroblasts by AlphaLISA.

Collagen induction by the peptides of the invention is evaluated with an AlphaLISA assay. The aim of this study is to investigate the ability of a product to induce collagen type I synthesis in human dermal fibroblasts isolated from adult skin (HDFa).

Figure 5:
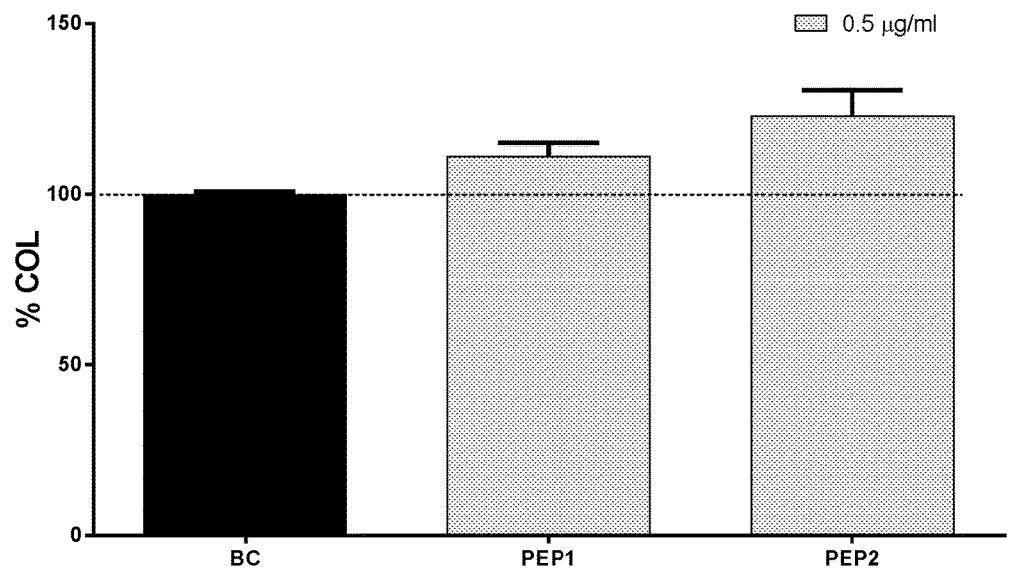
FIG. 5 shows levels of type 1 collagen on human dermal fibroblasts as determined by an alpha-ELISA assay (Example 11). The measurements are made on samples of human dermal fibroblasts treated with a compound of the invention and a basal control that is not treated with a compound of the invention. Abbreviations: % COL, Percentage of Collagen type I; BC, basal control.

HDFa (Promocell) are seeded in 48-well plates at a density of $1\times10^5$ in Fibroblast Growth Medium supplemented with C-39016 (Promocell). After 24-hours incubation, fresh Medium 106 supplemented with Low Serum Growth Supplement (Gibco) with 0.5 µg/ml of the test items is added. Treatment is continued for 48 hours and non-treated cells are used as basal control. After 48 hours treatment, cell supernatants are collected. Protease Inhibitor Cocktail (Sigma) is added to each supernatant and then are kept at −80° C. until they are analysed by AlphaLISA with AlphaLISA COL1A1™ Detection kit (PerkinElmer) following the manufacturer's instructions. Briefly, Donor beads and acceptor beads in the presence of Collagen type I are close enough to produce a luminescent signal directly proportional to the amount of Collagen Type I present in each condition tested. The luminescence produced by this reaction is measured in a microtiter plate reader and type I collagen concentration is determined using a linear regression of the standard curve. Results of collagen synthesis versus non-treated cells are shown in FIG. 5.

The results demonstrate that the peptides of the invention boost type I collagen production respect to basal conditions in HDFa at tested concentration.

Example 12

Inhibition of Noradrenaline Release from Human Neuroblastoma Cells.

The aim of this study is to evaluate the efficacy of the peptides of the invention on the inhibition of neuronal exocytosis by means of measuring the levels of noradrenaline (NA) release in human neuroblastoma cell line (SH-SY5Y cells) by Enzyme-linked Immunosorbent Assay (ELISA).

Figure 6:
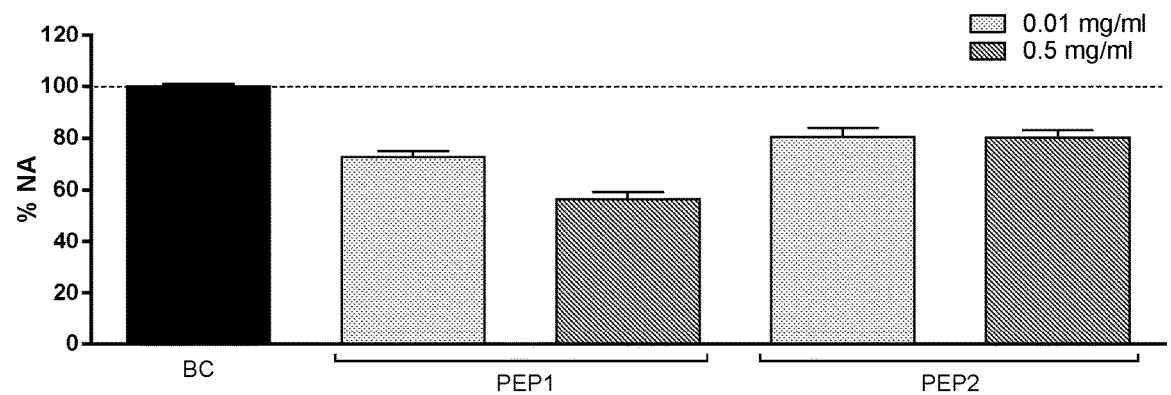
FIG. 6 shows levels of noradrenaline release on human neuroblastoma cell line ss determined using and immunofluorescence assay. The measurements are made on samples of human neuroblastoma cell line treated with a compound of the invention and a basal control that is not treated with a compound of the invention (Example 12). Abbreviations: NA, noradrenaline; BC, basal control.

SH-SY5Y (ECACC) cells are seeded in 12-well plates at a density of $1\times10^6$ cells/well. After a 6-day culture, medium is removed from wells and cells are treated for 60 minutes with the peptides of the invention dissolved in Hank's Balanced Salt Solution (HBSS, Life Technologies) at 0.01 and 0.5 mg/ml. Cells treated with HBSS alone are used as a basal control. To mobilize NA vesicles, supernatants are removed and 100 nM Tetradecanoylphorbol-13-acetate (TPA, Sigma) is dissolved in the presence of test items in HBSS or dissolved in HBSS alone in the case of the basal control. After this, solutions with TPA are removed and NA release is induced by the addition of 10 µM Ionomycin (Epica) with 100 nM TPA dissolved in the presence of test items in HBSS or dissolved in HBSS alone in the case of the basal control. Afterwards, the medium in the wells, containing released NA, is collected and centrifuged. Supernatants obtained are used for quantification of NA by ELISA with noradrenalin ELISA kit (IBL International) following manufacturer's instructions. In brief, direct sandwich ELISA is performed with a plate pre-coated with an anti-NA antibody. The color obtained after substrate addition is directly proportional to the amount of NA present in each condition tested. Absorbance is read in a microplate absorbance reader (Clariostar, BMG) at 405 nm. The percentage of NA release for each condition is calculated respect to basal control. Results of percentage of NA release versus non-treated cells (basal control) are shown in FIG. 6.

The results demonstrate that the peptides of the invention inhibit NA release respect to basal conditions in SH-SY5Y at tested concentration(s). An increase of exocytosis release in neuromuscular junction is related with aging and with an increase of facial wrinkles and expression lines. The peptides of the invention reduce exocytosis levels as they reduce NA release in SH-SY5Y.

Example 13

In Vitro Lipid Accumulation in Human Subcutaneous Pre-Adipocytes.

The aim of this study is to investigate the capacity of peptide candidates to induce lipid accumulation in human subcutaneous adipocytes, and therefore prevent adipocytes senescence. Measurement of lipid accumulation in a coculture of young and old adipose cells indirectly evaluates the inhibition of senescence-associated secretory phenotype (SASP). A pool of old adipose cells has a higher number of senescent cells. When cocultured with young cells, lipid accumulation observed is below the theoretically expected levels due to senescence induction effect of SASP on young adipocytes.

Figure 7:
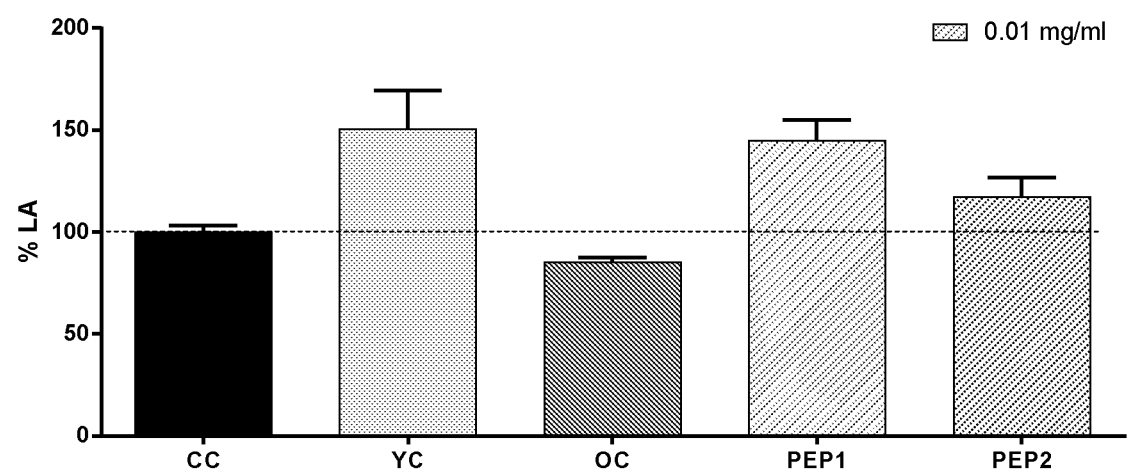
FIG. 7 shows levels of lipid accumulation in human subcutaneous pre-adipocytes as determined by fluorescent staining. The measurements are made on samples of a coculture of young and old pre-adipocytes that have been treated with a compound of the invention or that have not been treated with a compound of the invention. Results are also compared with a culture of old pre-adipocytes. Abbreviations: % LA, Percentage of lipid accumulation; CC, Coculture control; YC, young control; OC, old control.

Induction of lipid accumulation by the peptides of the invention is evaluated by lipid fluorescent staining with Adipored® Assay Reagent. Human subcutaneous pre-adipocytes (26-year-old and 60-year-old donors, Cell applications) cells are cocultured in 96-well plates at a density of $4\times10^3$ cells/well each age in Human Preadipocyte Growth Medium (Sigma). Monoculture of each age are seeded at a density of $8\times10^3$ cells/well as age lipid accumulation controls. After 24 hours incubation, differentiation of pre-adipocytes into adipocytes is induced by changing medium to fresh Human Preadipocyte Differentiation Medium (Promocell). At the same time, cocultured cells are treated with 0.01 mg/ml of test items. Non-treated cocultured cells are used as basal control and monocultured young and old cells as age lipid accumulation controls. After 12 days of treatment and differentiation, cells are stained with Adipored® Assay Reagent (Lonza) following the manufacturer's instructions. In brief, the plate is washed with Phosphate Buffer Saline (Sigma) and then Adipored® reagent and Hoechst 33342 (Life technologies) are added and incubated for 15 minutes at 37° C. Finally, fluorescence intensity and nuclei number are measured by Operetta™ (Perkin Elmer). Fluorescence is normalized by cell nuclei and results are represented respect to cocultured basal control. Results of percentage of lipid content versus non-treated cells (basal control) are showed in FIG. 7.

The results demonstrate that peptides PEP1 and PEP2 of the invention increase lipid accumulation in adipocytes when compared to basal control and old control.

Example 14

Preparation of a Cream Containing Peptide PEP1 (Ac-Asp-Val-Tyr-Lys-NH$_2$) Solution In a suitable vessel, the ingredients of phase A: water [INCI: WATER (AQUA)], Zemea™ [INCI: PROPANEDIOL], Hydrolite® 5 [INCI: PENTYLENE GLYCOL], Phenoxetol™ [INCI: PHENOXYETHANOL] and Dissolvine® NA2 [INCI: DISODIUM EDTA] are dissolved.

Phase A1 ingredient: Carbopol® Ultrez 10 Polymer [INCI: CARBOMER] is added to the previous mixture. Once dispersed, phase A2: Cola® Fax CPE-K [INCI: POTASSIUM CETYL PHOSPHATE] is introduced. Then the mixture is heated up to 70-75° C. In a separate vessel, phase B ingredients: Schercemol™ DIS Ester [INCI: DIISOPROPYL SEBACATE], Phytocream® 2000 [INCI: GLYCERYL STEARATE, CETEARYL ALCOHOL, POTASSIUM PALMITOYL HYDROLYZED WHEAT PROTEIN], Massocare® EC [INCI: ETHYLHEXYL COCOATE], Astro-sil™ 2C 350 [INCI: DIMETHICONE] and Tocopheryl Acetate [INCI: TOCOPHERYL ACETATE] are mixed and the resulting mixture is heated at 70-75° C.

The emulsion is made by adding slowly phase B into phase A under conditions of fast stirring with a turbine.

Once the mixture is cooled to 40° C., the components of phase C: November™ EC-1 polymer [INCI: MINERAL OIL (PARAFFINUM LIQUIDUM); WATER (AQUA); ACRYLATES/ACRYLAMIDE CROSSPOLYMER; POLYSORBATE 85] are added to the previous mixture under stirring and mixed until dispersion.

Phase D: Peptide PEP1 solution [INCI: GLYCERIN; WATER (AQUA); peptide PEP1 is added to the previous mixture.

Phase E: Fragrance [INCI: FRAGANCE (PARFUM)], is added.

pH is adjusted to 6.0-6.5 with phase F ingredient sodium hydroxide 20% w/w [INCI: WATER (AQUA); SODIUM HYDROXIDE]).

TABLE 4

| Phase | INGREDIENT (INCI name) | % weight |
|---|---|---|
| A | WATER | 69.10 |
| A | PROPANEDIOL | 10.00 |
| A | PENTYLENE GLYCOL | 2.00 |
| A | PHENOXYETHANOL | 0.50 |
| A | DISODIUM EDTA | 0.20 |
| A1 | CARBOMER | 0.50 |
| A2 | POTASSIUM CETYL PHOSPHATE | 0.50 |
| B | DIISOPROPYL SEBACATE | 5.00 |
| B | [GLYCERYL STEARATE; CETEARYL ALCOHOL; POTASSIUM PALMITOYL HYDROLYZED WHEAT PROTEIN] | 5.00 |
| B | ETHYLHEXYL COCOATE | 2.50 |
| B | DIMETHICONE | 1.00 |
| B | TOCOPHERYL ACETATE | 0.50 |
| C | [MINERAL OIL (PARAFFINUM LIQUIDUM); WATER (AQUA); ACRYLATES/ACRYLAMIDE CROSSPOLYMER; POLYSORBATE 85] | 1.00 |
| D | [GLYCERIN; WATER (AQUA); PEP1] | 2.00 |
| E | FRAGANCE (PARFUM) | 0.20 |
| F | [WATER (AQUA); SODIUM HYDROXIDE] | q.s. |

Preparation of a Cream Containing Peptide PEP2 (H-Ala-Leu-Lys-Pro-Asn-Thr-NH$_2$) Solution In a suitable vessel, the ingredients of phase A: water [INCI: WATER (AQUA)], Zemea™ [INCI: PROPANEDIOL], Hydrolite® 5 [INCI: PENTYLENE GLYCOL], Phenoxetol™ [INCI: PHENOXYETHANOL] and Dissolvine® NA2 [INCI: DISODIUM EDTA] are dissolved.

Phase A1 ingredient:Carbopol® Ultrez 10 Polymer [INCI: CARBOMER] is added to the previous mixture. Once dispersed, phase A2: Cola®Fax CPE-K [INCI: POTASSIUM CETYL PHOSPHATE] is introduced. Then the mixture is heated up to 70-75° C.

In a separate vessel, phase B ingredients: Schercemol™ DIS Ester [INCI: DI ISOPROPYL SEBACATE], Phytocream® 2000 [INCI: GLYCERYL STEARATE, CETEARYL ALCOHOL, POTASSIUM PALMITOYL HYDROLYZED WHEAT PROTEIN], Massocare® EC [INCI: ETHYLHEXYL COCOATE], Astro-sil™ 2C 350 [INCI: DIMETHICONE] and Tocopheryl Acetate [INCI: TOCOPHERYL ACETATE] are mixed and the resulting mixture is heated at 70-75° C.

The emulsion is made by adding slowly phase B into phase A under conditions of fast stirring with a turbine.

Once the mixture is cooled to 40° C., the components of phase C: Novemer™ EC-1 polymer [INCI: MINERAL OIL (PARAFFINUM LIQUIDUM); WATER (AQUA); ACRYLATES/ACRYLAMIDE CROSSPOLYMER; POLYSORBATE 85] are added to the previous mixture under stirring and mixed until dispersion.

Phase D: Peptide PEP2 solution [INCI: GLYCERIN; WATER (AQUA); peptide PEP2 is added to the previous mixture.

Phase E: Fragrance [INCI: FRAGANCE (PARFUM)], is added.

pH is adjusted to 6.0-6.5 with phase F ingredient sodium hydroxide 20% w/w [INCI: WATER (AQUA); SODIUM HYDROXIDE]).

TABLE 5

| Phase | INGREDIENT (INCI name) | % weight |
|---|---|---|
| A | WATER | 69.10 |
| A | PROPANEDIOL | 10.00 |
| A | PENTYLENE GLYCOL | 2.00 |
| A | PHENOXYETHANOL | 0.50 |
| A | DISODIUM EDTA | 0.20 |
| A1 | CARBOMER | 0.50 |
| A2 | POTASSIUM CETYL PHOSPHATE | 0.50 |
| B | DIISOPROPYL SEBACATE | 5.00 |
| B | [GLYCERYL STEARATE; CETEARYL ALCOHOL; POTASSIUM PALMITOYL HYDROLYZED WHEAT PROTEIN] | 5.00 |
| B | ETHYLHEXYL COCOATE | 2.50 |
| B | DIMETHICONE | 1.00 |
| B | TOCOPHERYL ACETATE | 0.50 |
| C | [MINERAL OIL (PARAFFINUM LIQUIDUM); WATER (AQUA); ACRYLATES/ACRYLAMIDE CROSSPOLYMER; POLYSORBATE 85] | 1.00 |
| D | [GLYCERIN; WATER (AQUA); PEP2] | 2.00 |
| E | FRAGANCE (PARFUM) | 0.20 |
| F | [WATER (AQUA); SODIUM HYDROXIDE] | q.s. |

Example 15

Preparation of a Gel-Cream Comprising Peptide PEP1 (Ac-Asp-Val-Tyr-Lys-NH$_2$).

In a suitable vessel, the ingredients of phase A: water [INCI: WATER (AQUA)], Zemea™ [INCI: PROPANE- DIOL], Phenoxetol® [INCI: PHENOXYETHANOL], Dissolvine® NA2 [INCI: DISODIUM EDTA] and Potassium Sorbate Granular [POTASSIUM SORBATE] are dispersed.

Phase A1 ingredient: Carbopol® Ultrez 21 Polymer [INCI: ACRYLATES/C10/30 ALKYL ACRYLATE CROSSPOLYMER] is added to the previous mixture under stirring. Once dispersed, phase A2: Xanthan Gum [INCI: XANTHAN GUM] is introduced to the previous mixture and stirred until complete dispersion.

In a separate vessel, phase B ingredients: Schercemol™ 1818 Ester [INCI: ISOSTEARYL ISOSTEARATE], is weighed.

The emulsion is made by adding slowly phase B into phase A under conditions of fast stirring with a turbine.

Phase C: Peptide PEP1 solution [INCI: WATER (AQUA); CAPRYLYL GLYCOL; Peptide PEP1 is added to the previous mixture.

pH is adjusted to 6.0-6.5 with phase D ingredient: Sodium Hydroxide 20% w/w [INCI: WATER (AQUA); SODIUM HYDROXIDE]).

TABLE 6

| Phase | INGREDIENT (INCI name) | % weight |
|---|---|---|
| A | WATER | 83.54 |
| A | PROPANEDIOL | 10.00 |
| A | PHENOXYETHANOL | 0.35 |
| A | DISODIUM EDTA | 0.20 |
| A | POTASSIUM SORBATE | 0.10 |
| A1 | ACRYLATES/C10/30 ALKYL ACRYLATE CROSSPOLYMER | 0.65 |
| A2 | XANTHAN GUM | 0.20 |
| B | ISOSTEARYL ISOSTEARATE | 2.00 |
| C | [WATER (AQUA); CAPRYLYL GLYCOL; PEPTIDE PEP1] | 2.00 |
| D | [WATER (AQUA); SODIUM HYDROXIDE] | 0.96 |

A gel-cream comprising peptide PEP2 (H-Ala-Leu-Lys-Pro-Asn-Thr-NH$_2$) can be obtained by substituting PEP2 for PEP1 in this example.

Example 16

Preparation of a Gel Comprising 2% of Peptide PEP1 (Ac-Asp-Val-Tyr-Lys-NH$_2$) Solution In a suitable vessel, the ingredients of phase A: water [INCI: WATER (AQUA)], Zemea™ [INCI: PROPANEDIOL], Glucam™ E-20 Humectant [INCI: METHYL GLUCETH-20], Dissolvine® NA2 [INCI: DISODIUM EDTA], Phenoxetol® [INCI: PHENOXYETHANOL] are dissolved.

Phase A1: Carbopol® ultrez 10 polymer [INCI: CARBOMER] is added to the previous mixture and mixed until complete dispersion.

Phase B: Peptide PEP-1 solution [INCI: WATER (AQUA); CAPRYLYL GLYCOL; PEP-1] is added to previous mixture and mixed.

Phase C: EUMULGIN® CO 40 [INCI: PEG-40 HYDROGENATED CASTOR OIL], Fragrance [INCI: FRAGRANCE (PARFUM)], is added to previous mixture and mixed.

The pH is adjusted to 6.0-6.5 with the ingredient of phase D: Sodium Hydroxide 20% w/w [INCI: WATER (AQUA); SODIUM HYDROXIDE].

TABLE 7

| Phase | INGREDIENT (INCI name) | % weight |
|---|---|---|
| A | WATER | 80.8 |
| A | PROPANEDIOL | 10 |
| A | METHYL GLUCETH-20 | 5 |
| A | PHENOXYETHANOL | 0.5 |
| A | DISODIUM EDTA | 0.2 |
| A1 | CARBOMER | 0.7 |
| B | [WATER (AQUA); CAPRYLYL GLYCOL; Peptide PEP1] | 2 |
| C | PEG-40 HYDROGENATED CASTOR OIL | 0.6 |
| C | FRAGRANCE (PARFUM) | 0.2 |
| D | [WATER (AQUA); SODIUM HYDROXIDE] | q.s. |

A gel comprising peptide PEP2 (H-Ala-Leu-Lys-Pro-Asn-Thr-NH$_2$) can be obtained by substituting PEP2 for PEP1 in this example.

Example 17

Preparation of a Lotion Comprising 2% of Peptide PEP1 (Ac-Asp-Val-Tyr-Lys-NH$_2$) Solution In a suitable vessel, the ingredients of phase A1: water [INCI: WATER (AQUA)], Zemea™ [INCI: PROPANEDIOL], glycerin [INCI: GLYCERIN], potassium sorbate [INCI: POTASSIUM SORBATE] and Dissolvine® NA2 [INCI: DISODIUM EDTA] are dissolved.

Phase A2 ingredient: Carbopol® Ultrez 30 Polymer [INCI: CARBOMER] is added in the previous mixture. Once dispersed, phase A3: xanthan gum [INCI: XANTHAN GUM] is introduced. Then the mixture is heated at 70-75° C.

In a separate vessel, phase B ingredients: Fancor® Meadowfoam seed oil [INCI: LIMNANTHES ALBA (MEADOWFOAM) SEED OIL], Kodasil™ 600 IDD Gel [INCI: ISODODECANE; VINYL DIMETHICONE/LAURYL DIMETHICONE CROSSPOLYMER; DIMETHICONE; LAURYL DIMETHICONE], Astro-sil™ 2C 350 [INCI: DIMETHICONE], Schercemol™ CATC ester [INCI: COCOYL ADIPIC ACID/TRIMETHYLOLPROPANE COPOLYMER; TRIMETHYLOLPROPANE], Schercemol™ DIS ester [INCI: DIISOPROPYL SEBACATE], Tocopheryl Acetate [INCI: TOCOPHERYL ACETATE] and Phenoxetol™ [INCI: PHENOXYETHANOL] are mixed and the resulting mixture is heated at 70-75° C.

The emulsion is made by adding slowly phase B into phase A under conditions of fast stirring with a turbine.

Once the mixture is cooled to 40° C., the components of phase C: Novemer™ EC-2 polymer [INCI: WATER (AQUA); SODIUM ACRYLATES/BEHENETH-25 METHACRYLATE CROSSPOLYMER; HYDROGENATED POLYDECENE, LAURYL GLUCOSIDE], SA-SB-300 (7%) [INCI: SILICA; DIMETHICONE], Fragrance [INCI: FRAGANCE (PARFUM)], and peptide PEP1 solution [INCI: WATER (AQUA); CAPRYLYL GLYCOL; peptide PEP1) are added to the previous mixture.

pH is adjusted to 6.0-6.5 with phase D ingredient sodium hydroxide 20% w/w [INCI: WATER (AQUA); SODIUM HYDROXIDE]).

TABLE 8

| Phase | INGREDIENT (INCI name) | % weight |
|---|---|---|
| A1 | WATER | 63.60 |
| A1 | PROPANEDIOL | 10.00 |
| A1 | GLYCERIN | 5.00 |

TABLE 8-continued

| Phase | INGREDIENT (INCI name) | % weight |
|---|---|---|
| A1 | POTASSIUM SORBATE | 0.10 |
| A1 | DISODIUM EDTA | 0.20 |
| A2 | CARBOMER | 0.30 |
| A3 | XANTHAN GUM | 0.20 |
| B | LIMNANTHES ALBA (MEADOWFOAM) SEED OIL | 5.00 |
| B | [ISODODECANE; VINYL DIMETHICONE/LAURYL DIMETHICONE CROSSPOLYMER; DIMETHICONE; LAURYL DIMETHICONE] | 3.00 |
| B | DIMETHICONE | 3.00 |
| B | [COCOYL ADIPIC ACID/TRIMETHYLOLPROPANE COPOLYMER; TRIMETHYLOLPROPANE] | 2.00 |
| B | DIISOPROPYL SEBACATE | 2.00 |
| B | TOCOPHERYL ACETATE | 0.50 |
| B | PHENOXYETHANOL | 0.50 |
| C | [WATER (AQUA); SODIUM ACRYLATES/BEHENETH-25 METHACRYLATE CROSSPOLYMER; HYDROGENATED POLYDECENE, LAURYL GLUCOSIDE] | 1.50 |
| C | [SILICA; DIMETHICONE] | 1.00 |
| C | [WATER (AQUA); CAPRYLYL GLYCOL; Peptide PEP1] | 2.00 |
| C | FRAGANCE (PARFUM) | 0.10 |
| D | [WATER (AQUA); SODIUM HYDROXIDE] | q.s. |

A lotion comprising peptide PEP2 (H-Ala-Leu-Lys-Pro-Asn-Thr-NH$_2$) can be obtained by substituting PEP2 for PEP1 in this example.

Example 18

Preparation of a Fluid Emulsion Comprising 2% of Peptide PEP1 (Ac-Asp-Val-Tyr-Lys-NH$_2$) Solution In a suitable vessel, the ingredients of phase A1: water [INCI: WATER (AQUA)], Zemea™ [INCI: PROPANEDIOL], glycerin [INCI: GLYCERIN], Genencare™ OSMS BA [INCI: BETAINE], Dissolvine® NA2 [INCI: DISODIUM EDTA], potassium sorbate [INCI: POTASSIUM SORBATE] are dissolved.

Phase A2: Carbopol® Ultrez 10 polymer [INCI: CARBOMER] is added to the previous mixture. Once dispersed, phase A3: Cola® Fax CPE-K [INCI: POTASSIUM CETYL PHOSPHATE] is added. The resulting mixture is heated at 70-75° C.

In another vessel, the components of phase B: Massocare® HD [INCI: ISOHEXADECANE], Lincol™ BAS [INCI: C12-15 ALKYL BENZOATE], Gandak™ C [INCI: CETYL ALCOHOL], Sorbital™ T 20 P [INCI: POLYSORBATE 20], 2-phenoxyethanol [INCI: PHENOXYETHANOL], Vegetable stearic acid 50/50 [INCI: STEARIC ACID; PALMITIC ACID] are mixed and heated at 70-75° C. Phase B is slowly introduced over phase A under conditions of intense stirring with a turbine.

The mixture is cooled at 40° C., and phase C: BRB™ CM 56-S [INCI: CYCLOMETHICONE], peptide PEP1 solution [INCI: WATER (AQUA); CAPRYLYL GLYCOL; peptide PEP1], Fragrance [INCI: FRAGRANCE (PARFUM)] is added. The pH is adjusted to 6.0-6.5 with the ingredient of phase D: Sodium Hydroxide 20% w/w [INCI: WATER (AQUA); SODIUM HYDROXIDE].

TABLE 9

| Phase | INGREDIENT (INCI name) | % weight |
|---|---|---|
| A1 | WATER | 71.2 |
| A1 | PROPANEDIOL | 10 |
| A1 | GLYCERIN | 3 |

TABLE 9-continued

| Phase | INGREDIENT (INCI name) | % weight |
|---|---|---|
| A1 | BETAINE | 3 |
| A1 | DISODIUM EDTA | 0.2 |
| A1 | POTASSIUM SORBATE | 0.1 |
| A2 | CARBOMER | 0.4 |
| A3 | POTASSIUM CETYL PHOSPHATE | 0.4 |
| B | ISOHEXADECANE | 2 |
| B | C12-15 ALKYL BENZOATE | 2 |
| B | CETYL ALCOHOL | 1.8 |
| B | POLYSORBATE 20 | 0.8 |
| B | PHENOXYETHANOL | 0.5 |
| B | [STEARIC ACID; PALMITIC ACID] | 0.5 |
| C | CYCLOMETHICONE | 2 |
| C | [WATER (AQUA); CAPRYLYL GLYCOL; PEP1] | 2 |
| C | FRAGRANCE (PARFUM) | 0.1 |
| D | [WATER (AQUA); SODIUM HYDROXIDE] | q.s. |

A fluid emulsion comprising peptide PEP2 (H-Ala-Leu-Lys-Pro-Asn-Thr-NH$_2$) can be obtained by substituting PEP2 for PEP1 in this example.

Example 19

In Vitro Quantification of Muscle Bind Like Protein 1 (MBNL1) in Human Skeletal Muscle Cells by Time Resolved Fluorescence Resonance Energy Transfer.

Different peptides of the invention are tested as disclosed in Example 7 at 0.5 mg/mL. Results are shown in Table 10 and demonstrate that all the peptides increase MBNL1 levels when compared to the basal control.

TABLE 10

| Identifier | Compound | % MBNL1 |
|---|---|---|
| PEP3 | Palm-Asp-Val-Tyr-Lys-NH$_2$ | 127.7 |
| PEP4 | Ac-Asp-Val-Tyr-Lys-OH | 378.5 |
| PEP5 | H-Asp-Val-Tyr-Lys-NH$_2$ | 261.4 |
| PEP7 | Ac-Glu-Val-Tyr-Lys-NH$_2$ | 141.5 |
| PEP8 | Ac-Asp-Ile-Tyr-Lys-NH$_2$ | 190.4 |
| PEP9 | Ac-Asp-Val-Phe-Lys-NH$_2$ | 134.2 |
| PEP10 | Ac-Asp-Val-Tyr-Arg-NH$_2$ | 158.3 |
| PEP11 | Ac-Asn-Val-Tyr-Lys-NH$_2$ | 145.2 |
| PEP12 | Ac-Asp-Leu-Tyr-Lys-NH$_2$ | 154.4 |
| PEP13 | Palm-Glu-Val-Tyr-Lys-NH$_2$ | 147.2 |
| PEP14 | Ac-Ala-Asp-Val-Tyr-Lys-NH$_2$ | 145.0 |
| PEP15 | Ac-Asp-Val-Tyr-Lys-Ala-NH$_2$ | 145.2 |
| PEP20 | Ac-Glu-Ile-Tyr-Lys-NH$_2$ | 214.2 |
| PEP23 | Ac-Glu-Ile-Tyr-Arg-NH$_2$ | 181.4 |
| PEP24 | Ac-Glu-Ile-Phe-Arg-NH$_2$ | 117.5 |

Example 20

In Vitro Quantification of Muscle Bind Like Protein 1 (MBNL1) in Human Skeletal Muscle Cells by Time Resolved Fluorescence Resonance Energy Transfer.

The assay is performed as disclosed in Example 7 except that hSkMc from TEBU-BIO (Barcelona, Spain) are used. Different peptides of the invention are tested at a concentration of 0.5 mg/ml.

Results are shown in Table 11 and demonstrate that all the peptides increase MBNL1 levels when compared to the basal control.

TABLE 11

| Identifier | Compound | % MBNL1 |
| --- | --- | --- |
| PEP27 | Ac-Ala-Leu-Lys-Pro-Asn-Thr-OH | 126.1 |
| PEP30 | H-Ala-Leu-Arg-Pro-Asn-Thr-$NH_2$ | 181.3 |
| PEP31 | H-Ala-Leu-Lys-Val-Asn-Thr-$NH_2$ | 120.0 |
| PEP40 | H-Leu-Lys-Pro-Asn-Thr-$NH_2$ | 117.3 |
| PEP41 | H-Ala-Leu-Lys-Pro-Asn-$NH_2$ | 138.4 |
| PEP42 | H-Gly-Ile-Lys-Pro-Asn-Thr-$NH_2$ | 114.2 |
| PEP44 | H-Ala-Ile-Arg-Pro-Asn-Thr-$NH_2$ | 240.6 |
| PEP46 | H-Gly-Val-Arg-Pro-Asn-Thr-$NH_2$ | 182.1 |
| PEP50 | H-Ala-Leu-Lys-Pro-Gln-Thr-$NH_2$ | 119.4 |

Example 21

In Vivo Study with a Composition Comprising PEP1, for the Assessment of Antiwrinkle and Smoothing Efficacy of Long-Term Application in Caucasian Skin Type Female Volunteers.

The study is carried out for 28 days. Forty-two (42) Caucasian female volunteers, aged between 35 and 58 years-old showing skin wrinkledness on the crow's feet area are included. Subjects apply a cream comprising PEP1 (ACTIVE cream) on one side of the face (left or right) and a placebo cream having the same composition except PEP1 (PLACEBO cream). Both creams are applied for 28 days twice a day (morning and evening). The subjects serve as their own reference and results obtained at time 28 days are compared with those obtained at initial time and between treatments (ACTIVE vs PLACEBO).

The antiwrinkle efficacy of the creams in crow's feet area is assessed by the determination of the maximum depth of biggest wrinkle: Images of volunteer's crow's feet area are measured with a 3D microtopography imaging system. Volunteers are instructed to remain in smiling expression and the maximum depth of the biggest wrinkle is taken at initial time and after 28 days of product application. Results of wrinkle reduction after treatment are shown in Table 12.

TABLE 12

| | % of reduction at 28 days |
| --- | --- |
| Active Cream | 4.8 |
| Placebo Cream | 1.6 |

Results show that after 28 days of application of the creams there is a reduction of the maximum depth of the biggest wrinkle compared to initial time. Said reduction is much higher for ACTIVE cream than PLACEBO cream.

The smoothing efficacy of the creams is assessed by determining the arithmetic roughness (Sa): Images of volunteer's cheek are taken with a 3D microtopography imaging system. Arithmetic roughness (Sa) measurements are taken at initial time and after 28 days of cream application. Results of roughness reduction after treatment are shown in Table 13.

TABLE 13

| | % of reduction at 28 days |
| --- | --- |
| Active Cream | 3.3 |
| Placebo Cream | 0.3 |

Results show that there is a reduction of arithmetic roughness (Sa) after treatment with ACTIVE cream whereas this effect is negligible with PLACEBO cream. Roughness reduction implies that the skin is smoother.

The invention claimed is:

1. A compound selected from the group consisting of:

$R_1$-Asp-Val-Tyr-Lys-$R_2$; ($R_1$-[SEQ ID NO. 1]-$R_2$)

$R_1$-Ala-Leu-Lys-Pro-Asn-Thr-$R_2$; ($R_1$-[SEQ ID NO. 2]-$R_2$)

$R_1$-Glu-Val-Tyr-Lys-$R_2$; ($R_1$-[SEQ ID NO. 3]-$R_2$)

$R_1$-Asp-Ile-Tyr-Lys-$R_2$; ($R_1$-[SEQ ID NO. 4]-$R_2$)

$R_1$-Asp-Val-Phe-Lys-$R_2$; ($R_1$-[SEQ ID NO. 5]-$R_2$)

$R_1$-Asp-Val-Tyr-Arg-$R_2$; ($R_1$-[SEQ ID NO. 6]-$R_2$)

$R_1$-Asn-Val-Tyr-Lys-$R_2$; ($R_1$-[SEQ ID NO. 7]-$R_2$)

$R_1$-Asp-Leu-Tyr-Lys-$R_2$; ($R_1$-[SEQ ID NO. 8]-$R_2$)

$R_1$-Ala-Asp-Val-Tyr-Lys-$R_2$; ($R_1$-[SEQ ID NO. 9]-$R_2$)

$R_1$-Asp-Val-Tyr-Lys-Ala-$R_2$; ($R_1$-[SEQ ID NO. 10]-$R_2$)

$R_1$-Glu-Ile-Tyr-Lys-$R_2$; ($R_1$-[SEQ ID NO. 15]-$R_2$)

$R_1$-Glu-Ile-Tyr-Arg-$R_2$; ($R_1$-[SEQ ID NO. 18]-$R_2$)

$R_1$-Glu-Ile-Phe-Arg-$R_2$; ($R_1$-[SEQ ID NO. 19]-$R_2$)

$R_1$-Ala-Leu-Arg-Pro-Asn-Thr-$R_2$; ($R_1$-[SEQ ID NO. 22]-$R_2$)

$R_1$-Ala-Leu-Lys-Val-Asn-Thr-$R_2$; ($R_1$-[SEQ ID NO. 23]-$R_2$)

$R_1$-Leu-Lys-Pro-Asn-Thr-$R_2$; ($R_1$-[SEQ ID NO. 30]-$R_2$)

$R_1$-Ala-Leu-Lys-Pro-Asn-$R_2$; ($R_1$-[SEQ ID NO. 31]-$R_2$)

$R_1$-Gly-Ile-Lys-Pro-Asn-Thr-$R_2$; ($R_1$-[SEQ ID NO. 32]-$R_2$)

$R_1$-Ala-Ile-Arg-Pro-Asn-Thr-$R_2$; ($R_1$-[SEQ ID NO. 34]-$R_2$)

$R_1$-Gly-Val-Arg-Pro-Asn-Thr-$R_2$; ($R_1$-[SEQ ID NO. 34]-$R_2$)

R1-Ala-Leu-Lys-Pro-Gln-Thr-$R_2$; ($R_1$-[SEQ ID NO. 40]-$R_2$)

and combinations thereof;

wherein $R_1$ is selected from the group consisting of H, a polymer derived from polyethylene glycol, a non-cyclic aliphatic group, alicyclyl, heterocyclyl, heteroarylalkyl, aryl, aralkyl and $R_5$—CO—, wherein $R_5$ is selected from the group consisting of H, a non-cyclic aliphatic group, alicyclyl, aryl, aralkyl, heterocyclyl and heteroarylalkyl;

$R_2$ is selected from the group consisting of —$NR_3R_4$, —$OR_3$, —$SR_3$, wherein $R_3$ and $R_4$ are independently selected from a group consisting of H, a polymer derived from polyethylene glycol, a non-cyclic aliphatic group, alicyclyl, heterocyclyl, heteroarylalkyl, aryl and aralkyl; and $R_1$ and $R_2$ are not amino acids.

2. A compound according to claim 1, wherein $R_1$ is selected from the group consisting of H and $R_5$—CO—, wherein $R_5$ is selected from the group consisting of $C_1$-$C_{18}$ alkyl, $C_2$-$C_{24}$ alkenyl, $C_3$-$C_{24}$ cycloalkyl; and $R_2$ is —$NR_3R_4$ or —$OR_3$ wherein $R_3$ and $R_4$ are independently selected from the group consisting of H and $C_1$-$C_{16}$ alkyl.

3. A compound according to claim 1, wherein the compound is selected from the group consisting of:

Ac-Asp-Val-Tyr-Lys-$NH_2$; (PEP1, Ac-[SEQ ID NO. 1]-$NH_2$)

H-Ala-Leu-Lys-Pro-Asn-Thr-$NH_2$; (PEP2, H-[SEQ ID NO. 2]-$NH_2$)

and combinations thereof.

4. A composition comprising a cosmetically effective quantity of a compound of claim 1, and at least one cosmetically acceptable excipient or adjuvant.

5. A combination of a compound according to claim 1 and at least one of Botulinum toxin and the peptide of sequence Ac-Glu-Glu-Met-Gln-Arg-Arg-$NH_2$ (Ac-[SEQ ID NO. 41]-$NH_2$.

6. A compound selected from the group consisting of:

Palm-Asp-Val-Tyr-Lys-$NH_2$; (PEP3, Palm-[SEQ ID NO. 1]-$NH_2$)

Ac-Asp-Val-Tyr-Lys-OH; (PEP4, Ac-[SEQ ID NO. 2]-OH)

H-Asp-Val-Tyr-Lys-$NH_2$; (PEP5, H-[SEQ ID NO. 2]-$NH_2$)

Ac-Glu-Val-Tyr-Lys-$NH_2$; (PEP7, Ac-[SEQ ID NO. 3]-$NH_2$)

Ac-Asp-Ile-Tyr-Lys-$NH_2$; (PEP8, Ac-[SEQ ID NO. 4]-$NH_2$)

Ac-Asp-Val-Phe-Lys-$NH_2$; (PEP9, Ac-[SEQ ID NO. 5]-$NH_2$)

```
        (PEP10, Ac-[SEQ ID NO. 6]-NH2)
Ac-Asp-Val-Tyr-Arg-NH2;

(PEP11, Ac-[SEQ ID NO. 7]-NH2)
Ac-Asn-Val-Tyr-Lys-NH2;

(PEP12, Ac-[SEQ ID NO. 8]-NH2)
Ac-Asp-Leu-Tyr-Lys-NH2;

(PEP13, Palm-[SEQ ID NO. 3]-NH2)
Palm-Glu-Val-Tyr-Lys-NH2;

(PEP14, Ac-[SEQ ID NO. 9]-NH2)
Ac-Ala-Asp-Val-Tyr-Lys-NH2;

(PEP15, Ac-[SEQ ID NO. 10]-NH2)
Ac-Asp-Val-Tyr-Lys-Ala-NH2;

(PEP20, Ac-[SEQ ID NO. 15]-NH2)
Ac-Glu-Ile-Tyr-Lys-NH2;

(PEP23, Ac-[SEQ ID NO. 18]-NH2)
Ac-Glu-Ile-Tyr-Arg-NH2;

(PEP24, Ac-[SEQ ID NO. 19]-NH2)
Ac-Glu-Ile-Phe-Arg-NH2;

(PEP27, Ac-[SEQ ID NO. 2]-OH)
Ac-Ala-Leu-Lys-Pro-Asn-Thr-OH;

(PEP30, H-[SEQ ID NO. 22]-NH2)
H-Ala-Leu-Arg-Pro-Asn-Thr-NH2;

(PEP31, H-[SEQ ID NO. 23]-NH2)
H-Ala-Leu-Lys-Val-Asn-Thr-NH2;

(PEP40, H-[SEQ ID NO. 30]-NH2)
H-Leu-Lys-Pro-Asn-Thr-NH2;

(PEP41, H-[SEQ ID NO. 31]-NH2)
H-Ala-Leu-Lys-Pro-Asn-NH2;

(PEP42, H-[SEQ ID NO. 32]-NH2)
H-Gly-Ile-Lys-Pro-Asn-Thr-NH2;

(PEP44, H-[SEQ ID NO. 34]-NH2)
H-Ala-Ile-Arg-Pro-Asn-Thr-NH2;

(PEP46, H-[SEQ ID NO. 36]-NH2)
H-Gly-Val-Arg-Pro-Asn-Thr-NH2;

(PEP50, H-[SEQ ID NO. 40]-NH2)
H-Ala-Leu-Lys-Pro-Gln-Thr-NH2-);
``` and combinations thereof.

7. A composition comprising a cosmetically effective quantity of a compound of claim 6, and at least one cosmetically acceptable excipient or adjuvant.

8. A method of treatment and/or care of the skin, of a subject comprising administering a compound according to claim 6 to the skin, of the subject, wherein the treatment and/or care comprises at least one of:

reduction of skin wrinkles; a stimulation of collagen synthesis; a reduction of collagen loss;

an improvement or maintenance of skin firmness; an increase of the volume of adipose tissue;

an alleviation of adipose tissue loss; a reduction of skin roughness; and an improvement in skin smoothness.

\* \* \* \* \*

SEQUENCE LISTING

```
<160> NUMBER OF SEQ ID NOS: 50

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Asp Val Tyr Lys
1

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2

Ala Leu Lys Pro Asn Thr
1               5

<210> SEQ ID NO 3
<211> LENGTH: 4
<212> TYPE: PRT
<213> ORGANISM: Artificial Sequence
<220> FEATURE:
```

```
<223> OTHER INFORMATION: Synthetic Peptide

<400> SEQUENCE: 3

Glu Val Tyr Lys
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 4

Asp Ile Tyr Lys
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 5

Asp Val Phe Lys
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 6

Asp Val Tyr Arg
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 7

Asn Val Tyr Lys
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 8

Asp Leu Tyr Lys
1

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide
```

<400> SEQUENCE: 9

Ala Asp Val Tyr Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 10

Asp Val Tyr Lys Ala
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 11

Ala Glu Val Tyr Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 12

Ala Asp Val Tyr Lys Ala
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 13

Ala Ala Asp Val Tyr Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 14

Ala Glu Val Tyr Lys Ala
1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic Peptide

```
<400> SEQUENCE: 15

Glu Ile Tyr Lys
1

<210> SEQ ID NO 16
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 16

Ala Glu Ile Tyr Lys Ala
1               5

<210> SEQ ID NO 17
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 17

Glu Ile Phe Lys
1

<210> SEQ ID NO 18
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 18

Glu Ile Tyr Arg
1

<210> SEQ ID NO 19
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 19

Glu Ile Phe Arg
1

<210> SEQ ID NO 20
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 20

Gly Leu Lys Pro Asn Thr
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 21
```

Ala Ile Lys Pro Asn Thr
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 22

Ala Leu Arg Pro Asn Thr
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 23

Ala Leu Lys Val Asn Thr
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 24

Ala Leu Lys Pro Asp Thr
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 25

Ala Leu Lys Pro Asn Ala
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 26

Ala Leu Lys Pro Asn Ser
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 27

Ala Ala Leu Lys Pro Asn Thr
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 28

Ala Leu Lys Pro Asn Thr Ala
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 29

Ala Ala Leu Lys Pro Asn Thr Ala
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 30

Leu Lys Pro Asn Thr
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 31

Ala Leu Lys Pro Asn
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 32

Gly Ile Lys Pro Asn Thr
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 33

Gly Val Lys Pro Asn Thr

```
1               5
```

<210> SEQ ID NO 34
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 34

```
Ala Ile Arg Pro Asn Thr
1               5
```

<210> SEQ ID NO 35
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 35

```
Ala Ile Lys Pro Asp Thr
1               5
```

<210> SEQ ID NO 36
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 36

```
Gly Val Arg Pro Asn Thr
1               5
```

<210> SEQ ID NO 37
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 37

```
Ala Ile Arg Pro Asp Thr
1               5
```

<210> SEQ ID NO 38
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 38

```
Gly Val Arg Pro Asp Thr
1               5
```

<210> SEQ ID NO 39
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 39

```
Gly Leu Lys Pro Asn Thr Ala
1               5
```

```
<210> SEQ ID NO 40
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 40

Ala Leu Lys Pro Gln Thr
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: The amino acid at position 1 is modified with
      an acetyl group
<220> FEATURE:
<221> NAME/KEY: MISC_FEATURE
<222> LOCATION: (6)..(6)
<223> OTHER INFORMATION: The amino acid at position 6 is modified with
      an amino group

<400> SEQUENCE: 41

Glu Glu Met Gln Arg Arg
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: The amino acid at position 1 is modified with a
      proton
<220> FEATURE:
<221> NAME/KEY: Xaa
<222> LOCATION: (2)..(2)
<223> OTHER INFORMATION: Xaa is D-Ala
<220> FEATURE:
<221> NAME/KEY: MISC_FEATURE
<222> LOCATION: (5)..(5)
<223> OTHER INFORMATION: The amino acid at position 5 is modified with a
      hydroxy group

<400> SEQUENCE: 42

Tyr Xaa Gly Phe Leu
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 43

Pro Leu Asp Val Tyr Lys
1               5

<210> SEQ ID NO 44
```

```
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 44

Tyr Lys Asp Val Tyr Lys
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 45

Arg Lys Asp Val Tyr Lys
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 46

Arg Asn Asp Val Tyr Lys
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 47

Arg Asp Val Tyr Lys Gln Asn
1               5

<210> SEQ ID NO 48
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 48

Asp Ala Tyr Lys
1

<210> SEQ ID NO 49
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 49

Asp Leu Lys Lys
1

<210> SEQ ID NO 50
<211> LENGTH: 6
```

```
<212> TYPE: PRT
<213> ORGANISM: Artificial Sequence
<220> FEATURE:
<223> OTHER INFORMATION: Synthetic Peptide

<400> SEQUENCE: 50

His Asp Leu Lys Lys Tyr
1               5
```